US006444660B1

(12) United States Patent
Unger et al.

(10) Patent No.: US 6,444,660 B1
(45) Date of Patent: Sep. 3, 2002

(54) LIPID SOLUBLE STEROID PRODRUGS

(75) Inventors: Evan C. Unger; DeKang Shen, both of Tucson, AZ (US)

(73) Assignee: Imarx Therapeutics, Inc., Tucson, AZ (US)

(*) Notice: Subject to any disclaimer, the term of this patent is extended or adjusted under 35 U.S.C. 154(b) by 0 days.

(21) Appl. No.: 09/496,761

(22) Filed: Feb. 3, 2000

Related U.S. Application Data

(62) Division of application No. 08/851,780, filed on May 6, 1997, now Pat. No. 6,090,800.

(51) Int. Cl.[7] .............................................. A61K 31/56
(52) U.S. Cl. ...................................................... 514/180
(58) Field of Search .......................... 552/574; 514/180

(56) References Cited

U.S. PATENT DOCUMENTS

| | | | |
|---|---|---|---|
| 3,015,128 A | 1/1962 | Sommerville et al. | 18/2.6 |
| 3,291,843 A | 12/1966 | Fritz et al. | 260/614 |
| 3,293,114 A | 12/1966 | Kenaga et al. | 162/168 |
| 3,401,475 A | 9/1968 | Morehouse et al. | 40/306 |
| 3,479,811 A | 11/1969 | Walters | 57/153 |
| 3,488,714 A | 1/1970 | Walters et al. | 161/161 |
| 3,532,500 A | 10/1970 | Priest et al. | 96/91 |
| 3,557,294 A | 1/1971 | Dear et al. | 424/342 |
| 3,594,326 A | 7/1971 | Himmel et al. | 252/316 |
| 3,615,972 A | 10/1971 | Morehouse et al. | 156/79 |
| 3,647,784 A | 3/1972 | Stein et al. | 260/239.55 R |
| 3,649,620 A | 3/1972 | Ercoli et al. | 260/239.55 |
| 3,650,831 A | 3/1972 | Jungermann et al. | 134/27 |
| 3,732,172 A | 5/1973 | Herbig et al. | 252/316 |
| 3,873,564 A | 3/1975 | Schneider et al. | 270/309.6 |
| 3,945,956 A | 3/1976 | Garner | 270/2.5 B |
| 3,960,583 A | 6/1976 | Netting et al. | 106/122 |
| 3,968,203 A | 7/1976 | Spitzer et al. | 424/47 |
| 4,027,007 A | 5/1977 | Messina | 424/46 |
| 4,089,801 A | 5/1978 | Schneider | 252/316 |
| 4,108,806 A | 8/1978 | Cohrs et al. | 521/54 |
| 4,138,383 A | 2/1979 | Rembaum et al. | 270/29.7 H |
| 4,162,282 A | 7/1979 | Fulwyler et al. | 274/9 |
| 4,179,546 A | 12/1979 | Garner et al. | 521/56 |

(List continued on next page.)

FOREIGN PATENT DOCUMENTS

| | | |
|---|---|---|
| AU | 641363 | 3/1990 |
| AU | B-30351/89 | 3/1993 |
| DE | 25 21 003 | 8/1976 |
| DE | 3803972 | 8/1989 |
| EP | 0 052 575 | 5/1982 |
| EP | 0 107 559 | 5/1984 |
| EP | 0 077 752 B1 | 3/1986 |
| EP | 0 224 934 | 6/1987 |
| EP | 0 231 091 | 8/1987 |
| EP | 0 243 947 | 11/1987 |
| EP | 0 272 091 | 6/1988 |
| EP | 0 320 433 A2 | 12/1988 |
| EP | 0 324 938 | 1/1989 |
| EP | 0 338 971 | 10/1989 |
| EP | 357163 A1 | 3/1990 |
| EP | 0 359 246 | 3/1990 |
| EP | 0 361 894 | 4/1990 |
| EP | 0 216 730 | 1/1991 |
| EP | 441468 A2 | 8/1991 |
| EP | 0 357 164 B1 | 10/1991 |
| EP | 0 458 745 A1 | 11/1991 |
| EP | 467 031 A2 | 1/1992 |
| EP | 0 314 764 B1 | 9/1992 |
| EP | 0 554 213 A1 | 8/1993 |

(List continued on next page.)

OTHER PUBLICATIONS

Kuhl et al., "A new class of long–acting hormonal steroid preparation: Synthesis of oligomeric estradiol derivatives", *Steroids*, 22(1), 1973, pp. 73–87.*

Hautanen, A., et al., "Effects of modifications of the RGD sequence and its context on recognition by the fibronectin receptor," *J. Biol. Chem.*, 1989, 264(3), 1437–1442.

Takeuchi, M., et al., "Enhanced visualization of intravascular thrombus with the use of a thrombus targeting ultrasound contrast agent (MRX408): Evidence from in vivo experimental echocardiographic studies," *J. Am. College of Cardiology*, 1998, 81(12), 1 page, Abstract XP–000952675.

Unger, E.C., et al., "In vitrostudies of a new thrombus–specific ultrasound contrast agent," *J. of Cardiology*, 1998, 81(12), 58G–61G, Abstract XP–002087505.

Wu, Y., et al., "Binding and lysing of blood clots using MRX–408," *Investigate Radiology*, 1998, 33(12), 880–885.

Fitzpatrick et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, 1974, 13(3), 568–574.

Thanassi, "Aminomalonic Acid: Spontaneous Decarboxylation and Reaction with 5–Deoxypyridoxal", *Biochemistry*, 1970, 9(3), 525–532.

Stel'mashok et al., "Photolysis of Frozen Solutions of Malonate Complexes", *Koordinatsionnaya Khimiya*, 1977, 3(4), 524–527 (Russian and English language versions).

Mayhew et al., "High–Pressure Continuous–Flow System for Drug Entrapment in Liposomes", *Methods in Enzymology*, 1987, 149, 64–77.

Mayhew et al., "Characterization of Liposomes Prepared Using a Microemulsifier", *Biochim. et Biophys. Acta*, 1984, 775, 169–174.

Hope et al., "Production of Large Unilamellar Vesicles by a Rapid Extrusion Procedure: Characterization of Size Distribution, Trapped Volume, and Ability to Maintain a Membrane Potential", *Biochim. et Biophys. Acta*, 1985, 812, 55–65.

(List continued on next page.)

*Primary Examiner*—Barbara P. Badio
(74) *Attorney, Agent, or Firm*—Woodcock Washburn LLP

(57) ABSTRACT

The present invention is directed to novel lipid soluble steroid prodrugs, compositions comprising steroid prodrugs, and uses of the same.

13 Claims, No Drawings

U.S. PATENT DOCUMENTS

| | | |
|---|---|---|
| 4,192,859 A | 3/1980 | Mackaness et al. ............. 424/5 |
| 4,224,179 A | 9/1980 | Schneider ................... 252/316 |
| 4,229,360 A | 10/1980 | Schneider et al. .......... 270/403 |
| 4,265,251 A | 5/1981 | Tickner ....................... 128/660 |
| 4,276,885 A | 7/1981 | Tickner et al. .............. 128/660 |
| 4,310,505 A | 1/1982 | Baldeschwieler et al. ....... 424/1 |
| 4,310,506 A | 1/1982 | Baldeschwieler et al. ....... 424/1 |
| 4,315,514 A | 2/1982 | Drewes et al. ............. 128/653 |
| 4,331,654 A | 5/1982 | Morris ........................ 424/38 |
| 4,342,826 A | 8/1982 | Cole ............................ 435/7 |
| 4,344,929 A | 8/1982 | Bonsen et al. ................ 424/15 |
| 4,420,442 A | 12/1983 | Sands .......................... 274/13 |
| 4,421,562 A | 12/1983 | Sands et al. ................. 106/75 |
| 4,426,330 A | 1/1984 | Sears ........................ 270/403 |
| 4,427,649 A | 1/1984 | Dingle et al. ................ 424/38 |
| 4,428,924 A | 1/1984 | Millington ..................... 424/4 |
| 4,442,843 A | 4/1984 | Rasor et al. ................ 128/660 |
| 4,466,442 A | 8/1984 | Hilmann et al. ............ 128/653 |
| 4,485,193 A | 11/1984 | Rubens et al. ................ 521/58 |
| 4,530,360 A | 7/1985 | Duarte ................... 128/419 F |
| 4,533,254 A | 8/1985 | Cook et al. ................. 366/176 |
| 4,534,899 A | 8/1985 | Sears ........................ 270/403 |
| 4,540,629 A | 9/1985 | Sands et al. ................ 428/402 |
| 4,544,545 A | 10/1985 | Ryan et al. .................. 424/1.1 |
| 4,549,892 A | 10/1985 | Baker et al. ................. 65/21.4 |
| 4,569,836 A | 2/1986 | Gordon |
| 4,572,203 A | 2/1986 | Feinstein .................... 128/661 |
| 4,586,512 A | 5/1986 | Do-huu et al. ............ 128/660 |
| 4,603,044 A | 7/1986 | Geho et al. .................... 424/9 |
| 4,615,879 A | 10/1986 | Runge et al. .................. 424/9 |
| 4,620,546 A | 11/1986 | Aida et al. ................. 128/660 |
| 4,646,756 A | 3/1987 | Watmough et al. ......... 128/804 |
| 4,657,756 A | 4/1987 | Rasor et al. ................... 424/9 |
| 4,658,828 A | 4/1987 | Dory ......................... 128/660 |
| 4,663,161 A | 5/1987 | Mannino et al. .............. 424/89 |
| 4,675,310 A | 6/1987 | Chapman et al. .............. 514/6 |
| 4,681,119 A | 7/1987 | Rasor et al. ................ 128/660 |
| 4,684,479 A | 8/1987 | D'Arrigo .................... 252/307 |
| 4,689,986 A | 9/1987 | Carson et al. .................. 73/19 |
| 4,693,999 A * | 9/1987 | Axelsson et al. ........... 514/174 |
| 4,718,433 A | 1/1988 | Feinstein .................... 128/660 |
| 4,728,575 A | 3/1988 | Gamble et al. ........... 428/402.2 |
| 4,728,578 A | 3/1988 | Higgins et al. .............. 428/462 |
| 4,731,239 A | 3/1988 | Gordon ........................ 424/9 |
| 4,737,323 A | 4/1988 | Martin et al. ................ 274/4.3 |
| 4,774,958 A | 10/1988 | Feinstein ............... 128/660.01 |
| 4,775,522 A | 10/1988 | Clark, Jr. ........................ 424/9 |
| 4,776,991 A | 10/1988 | Farmer et al. ............... 274/4.3 |
| 4,781,871 A | 11/1988 | West, III et al. ............. 274/4.3 |
| 4,789,501 A | 12/1988 | Day et al. ................... 252/645 |
| 4,790,891 A | 12/1988 | Halliday et al. ............... 149/2 |
| 4,822,534 A | 4/1989 | Lencki et al. ............... 274/4.3 |
| 4,830,858 A | 5/1989 | Payne et al. ................ 424/450 |
| 4,834,964 A | 5/1989 | Rosen ........................... 424/9 |
| 4,844,882 A | 7/1989 | Widder et al. .................. 424/9 |
| 4,863,717 A | 9/1989 | Keana ........................... 424/9 |
| 4,863,965 A | 9/1989 | Jansen et al. ................ 514/576 |
| 4,865,836 A | 9/1989 | Long, Jr. ....................... 424/5 |
| 4,877,561 A | 10/1989 | Iga et al. .................... 274/4.3 |
| 4,893,624 A | 1/1990 | Lele ........................... 128/399 |
| 4,895,719 A | 1/1990 | Radhakrishnan ............. 424/45 |
| 4,898,734 A | 2/1990 | Mathiowitz et al. ........ 424/427 |
| 4,900,540 A | 2/1990 | Ryan et al. ..................... 424/9 |
| 4,913,852 A | 4/1990 | Milioni et al. ............... 514/179 |
| 4,918,065 A | 4/1990 | Stindl et al. ................. 514/179 |
| 4,919,895 A | 4/1990 | Heldebrant et al. ......... 422/129 |
| 4,921,706 A | 5/1990 | Roberts et al. ............. 424/450 |
| 4,927,623 A | 5/1990 | Long, Jr. ....................... 424/5 |
| 4,933,121 A | 6/1990 | Law et al. ................... 264/4.3 |
| 4,938,947 A | 7/1990 | Nicolau et al. .............. 424/1.1 |
| 4,957,656 A | 9/1990 | Cerny et al. ................. 252/311 |
| 4,972,002 A | 11/1990 | Volkert ....................... 521/120 |
| 4,981,692 A | 1/1991 | Popescu et al. ............. 424/422 |
| 4,984,573 A | 1/1991 | Leunbach ................... 128/653 |
| 4,985,550 A | 1/1991 | Charpiot et al. ............ 536/18.4 |
| 4,987,154 A | 1/1991 | Long, Jr. ..................... 514/772 |
| 4,993,415 A | 2/1991 | Long ..................... 128/653 A |
| 4,996,041 A | 2/1991 | Arai et al. ..................... 424/9 |
| 5,000,960 A | 3/1991 | Wallach ...................... 424/450 |
| 5,004,611 A | 4/1991 | Leigh ......................... 424/450 |
| 5,008,050 A | 4/1991 | Cullis et al. .................. 274/4.3 |
| 5,008,109 A | 4/1991 | Tin .............................. 424/422 |
| 5,013,556 A | 5/1991 | Woodle et al. .............. 424/450 |
| 5,015,746 A | 5/1991 | Mizushima et al. ......... 552/569 |
| 5,019,370 A | 5/1991 | Jay et al. ....................... 424/4 |
| 5,045,304 A | 9/1991 | Schneider et al. ............. 424/9 |
| 5,049,388 A | 9/1991 | Knight et al. ............... 424/450 |
| B14,229,360 A | 11/1991 | Schneider et al. .......... 270/403 |
| 5,078,994 A | 1/1992 | Nair et al. ................... 424/501 |
| 5,088,499 A | 2/1992 | Unger ..................... 128/662.2 |
| 5,107,842 A | 4/1992 | Levene et al. ......... 128/662.02 |
| 5,114,703 A | 5/1992 | Wolf et al. ..................... 424/5 |
| 5,118,494 A * | 6/1992 | Schultz et al. ................. 424/45 |
| 5,123,414 A | 6/1992 | Unger ........................ 128/654 |
| 5,135,000 A | 8/1992 | Akselrod et al. ....... 128/662.02 |
| 5,137,928 A | 8/1992 | Erbel et al. ................... 521/56 |
| 5,141,738 A | 8/1992 | Rasor et al. ..................... 424/2 |
| 5,147,631 A | 9/1992 | Glajch et al. ................... 424/9 |
| 5,149,319 A | 9/1992 | Unger ........................ 604/22 |
| 5,171,755 A | 12/1992 | Kaufman ..................... 514/759 |
| 5,173,298 A * | 12/1992 | Meadows ................... 424/427 |
| 5,186,922 A | 2/1993 | Shell et al. ................. 128/654 |
| 5,190,766 A | 3/1993 | Ishihara ...................... 424/489 |
| 5,190,982 A | 3/1993 | Erbel et al. ................... 521/56 |
| 5,192,549 A | 3/1993 | Barenolz et al. ............. 424/450 |
| 5,194,266 A | 3/1993 | Abra et al. ................... 424/450 |
| 5,195,520 A | 3/1993 | Schlief et al. ......... 128/660.02 |
| 5,196,183 A | 3/1993 | Yudelson et al. ............... 424/9 |
| 5,196,348 A | 3/1993 | Schweighardt et al. ...... 436/173 |
| 5,198,225 A | 3/1993 | Meybeck et al. ........... 424/450 |
| 5,205,287 A | 4/1993 | Erbel et al. ................. 128/632 |
| 5,205,290 A | 4/1993 | Unger ..................... 128/653.4 |
| 5,209,720 A | 5/1993 | Unger ........................ 604/22 |
| 5,213,804 A | 5/1993 | Martin et al. ............... 424/450 |
| 5,215,680 A | 6/1993 | D'Arrigo .................... 252/307 |
| 5,219,538 A | 6/1993 | Henderson et al. ....... 428/402.2 |
| 5,228,446 A | 7/1993 | Unger et al. ........... 128/662.02 |
| 5,230,882 A | 7/1993 | Unger .......................... 424/9 |
| 5,234,680 A | 8/1993 | Rogers, Jr. et al. ............. 424/9 |
| 5,247,935 A | 9/1993 | Cline et al. ............... 128/653.2 |
| 5,271,928 A | 12/1993 | Schneider et al. ............. 424/9 |
| 5,281,408 A | 1/1994 | Unger ........................... 424/4 |
| 5,305,757 A | 4/1994 | Unger et al. ........... 128/662.02 |
| 5,310,540 A | 5/1994 | Giddey et al. .................. 424/9 |
| 5,312,617 A | 5/1994 | Unger et al. .................... 424/9 |
| 5,315,997 A | 5/1994 | Widder et al. ........... 128/653.3 |
| 5,315,998 A | 5/1994 | Tachibana et al. ...... 128/660.01 |
| 5,316,771 A | 5/1994 | Barenholz et al. ........... 424/450 |
| 5,334,381 A | 8/1994 | Unger .......................... 424/9 |
| 5,339,814 A | 8/1994 | Lasker ..................... 128/653.4 |
| 5,344,930 A | 9/1994 | Riess et al. ..................... 544/84 |
| 5,350,571 A | 9/1994 | Kaufman et al. ............... 424/9 |
| 5,352,435 A | 10/1994 | Unger ........................... 424/9 |
| 5,354,549 A | 10/1994 | Klaveness et al. .............. 424/3 |
| 5,358,702 A | 10/1994 | Unger ........................... 424/9 |
| 5,362,477 A | 11/1994 | Moore et al. ................... 424/9 |
| 5,362,478 A | 11/1994 | Desai et al. .................... 424/9 |
| 5,371,077 A | 12/1994 | Schroepfer, Jr. et al. ..... 514/179 |
| 5,380,519 A | 1/1995 | Schneider et al. .............. 424/9 |
| 5,393,524 A | 2/1995 | Quay ............................ 424/9 |
| 5,409,688 A | 4/1995 | Quay ............................ 424/9 |

| | | | | | | |
|---|---|---|---|---|---|---|
| 5,410,516 A | 4/1995 | Uhlendorf et al. ............. 367/7 | | 5,686,060 A | 11/1997 | Schneider et al. ......... 424/9.52 |
| 5,413,774 A | 5/1995 | Schneider et al. ......... 424/9.51 | | 5,686,102 A | 11/1997 | Gross et al. ................. 424/450 |
| 5,425,366 A | 6/1995 | Reinhardt et al. ..... 128/662.02 | | 5,695,460 A | 12/1997 | Siegel et al. .................... 604/21 |
| 5,433,204 A | 7/1995 | Olson .................... 128/661.08 | | 5,701,899 A | 12/1997 | Porter .................... 428/662.02 |
| 5,445,813 A | 8/1995 | Schneider et al. ......... 424/9.51 | | 5,707,352 A | 1/1998 | Sekins et al. ................. 604/56 |
| 5,456,900 A | 10/1995 | Unger ........................ 424/9.4 | | 5,707,606 A | 1/1998 | Quay ........................ 424/9.52 |
| 5,460,800 A | 10/1995 | Walters ...................... 424/9.6 | | 5,707,607 A | 1/1998 | Quay ........................ 424/9.52 |
| 5,466,467 A | 11/1995 | Singh ......................... 424/450 | | 5,711,933 A | 1/1998 | Bichon et al. ............. 424/9.52 |
| 5,469,854 A | 11/1995 | Unger et al. .......... 128/662.02 | | 5,716,597 A | 2/1998 | Lohrmann et al. ........... 424/9.5 |
| 5,470,582 A | 11/1995 | Supersaxo et al. .......... 424/489 | | 5,732,707 A | 3/1998 | Widder et al. ......... 128/661.08 |
| 5,485,839 A | 1/1996 | Aida et al. ............... 128/653.1 | | 5,733,527 A | 3/1998 | Schutt ...................... 424/9.52 |
| 5,487,390 A | 1/1996 | Cohen et al. .......... 128/662.02 | | 5,736,121 A | 4/1998 | Unger ........................ 424/9.4 |
| 5,496,535 A | 3/1996 | Kirkland .................... 424/9.37 | | 5,740,807 A | 4/1998 | Porter .................... 128/662.02 |
| 5,498,421 A | 3/1996 | Grinstaff et al. ............. 424/450 | | 5,770,222 A | 6/1998 | Unger et al. ................. 424/450 |
| 5,501,863 A | 3/1996 | Rösling et al. .............. 424/489 | | 5,804,162 A | 9/1998 | Kabalnov et al. .......... 424/9.51 |
| 5,502,094 A | 3/1996 | Moore et al. ................. 524/145 | | 5,830,430 A | 11/1998 | Unger et al. ................ 424/1.21 |
| 5,505,932 A | 4/1996 | Grinstaff et al. ............. 424/9.3 | | 5,840,023 A | 11/1998 | Oraevsky et al. ........... 600/407 |
| 5,508,021 A | 4/1996 | Grinstaff et al. ......... 424/9.322 | | 5,846,517 A | 12/1998 | Unger ....................... 424/9.52 |
| 5,512,268 A | 4/1996 | Grinstaff et al. ............. 424/322 | | 5,849,727 A | 12/1998 | Porter et al. ................ 514/156 |
| 5,527,521 A | 6/1996 | Unger ........................ 424/93 | | 5,855,865 A | 1/1999 | Lambert et al. ........... 424/9.52 |
| 5,529,766 A | 6/1996 | Klaveness et al. ......... 424/9.52 | | 5,858,399 A | 1/1999 | Lanza et al. ................. 424/450 |
| 5,531,980 A | 7/1996 | Schneider et al. ......... 424/9.52 | | 5,874,062 A | 2/1999 | Unger ........................ 424/9.4 |
| 5,536,489 A | 7/1996 | Lohrmann et al. .......... 424/9.52 | | 5,897,851 A | 4/1999 | Quay et al. ................. 424/9.52 |
| 5,536,490 A | 7/1996 | Klaveness et al. ......... 424/9.52 | | 5,976,501 A | 11/1999 | Jablonski .................... 424/9.52 |
| 5,540,909 A | 7/1996 | Schutt ...................... 424/9.52 | | 5,997,898 A | 12/1999 | Unger ....................... 424/450 |
| 5,542,935 A | 8/1996 | Unger et al. ................. 604/190 | | 6,056,938 A | 5/2000 | Unger et al. ................ 424/1.21 |
| 5,545,396 A | 8/1996 | Albert et al. .................. 424/93 | | | | |
| 5,547,656 A | 8/1996 | Unger ........................ 424/9.4 | | FOREIGN PATENT DOCUMENTS | | |
| 5,552,133 A | 9/1996 | Lambert et al. ............. 424/9.52 | | | | |
| 5,552,155 A | 9/1996 | Bailey et al. ................ 424/450 | | EP | 0 586 875 | 3/1994 |
| 5,556,372 A | 9/1996 | Talish et al. .................... 601/2 | | EP | 0 614 656 A1 | 9/1994 |
| 5,556,610 A | 9/1996 | Yan et al. ................... 424/9.52 | | EP | 0 633 030 A1 | 1/1995 |
| 5,558,092 A | 9/1996 | Unger et al. ........... 128/660.03 | | EP | 0 727 225 A2 | 8/1996 |
| 5,558,094 A | 9/1996 | Quay .................... 128/662.02 | | EP | 0 901 793 A1 | 3/1999 |
| 5,558,853 A | 9/1996 | Quay ........................ 424/9.5 | | FR | 2 700 952 | 8/1994 |
| 5,558,854 A | 9/1996 | Quay ........................ 424/9.52 | | GB | 1044680 | 10/1966 |
| 5,558,855 A | 9/1996 | Quay ........................ 424/9.5 | | GB | 2193095 A | 2/1988 |
| 5,558,856 A | 9/1996 | Klaveness et al. ......... 424/9.37 | | JP | 62 286534 | 12/1987 |
| 5,560,364 A | 10/1996 | Porter .................... 128/662.02 | | JP | SHO 60-60943 | 3/1988 |
| 5,562,608 A | 10/1996 | Sekins et al. ................. 604/20 | | WO | WO 01/15742 | 3/1901 |
| 5,562,893 A | 10/1996 | Lohrmann .................. 424/9.52 | | WO | WO 80/02365 | 11/1980 |
| 5,565,215 A | 10/1996 | Gref et al. .................... 424/501 | | WO | WO 82/01642 | 5/1982 |
| 5,567,413 A | 10/1996 | Klaveness et al. ......... 424/9.51 | | WO | WO 84/02909 | 8/1984 |
| 5,567,414 A | 10/1996 | Schneider et al. ......... 424/9.52 | | WO | WO 85/01161 | 3/1985 |
| 5,567,415 A | 10/1996 | Porter ....................... 424/9.52 | | WO | WO 85/02772 | 7/1985 |
| 5,567,765 A | 10/1996 | Moore et al. ................. 524/801 | | WO | WO 86/00238 | 1/1986 |
| 5,569,448 A | 10/1996 | Wong et al. ................. 424/9.45 | | WO | WO 86/01103 | 2/1986 |
| 5,569,449 A | 10/1996 | Klaveness et al. ......... 424/9.51 | | WO | WO 89/05040 | 6/1989 |
| 5,571,797 A | 11/1996 | Ohno et al. .................... 514/44 | | WO | WO 90/01952 | 3/1990 |
| 5,573,751 A | 11/1996 | Quay ........................ 424/9.52 | | WO | WO 90/04384 | 5/1990 |
| 5,578,292 A | 11/1996 | Schneider et al. ......... 424/9.51 | | WO | WO 90/04943 | 5/1990 |
| 5,580,575 A | 12/1996 | Unger et al. ................. 424/450 | | WO | WO 91/00086 | 1/1991 |
| 5,585,112 A | 12/1996 | Unger et al. ................. 424/450 | | WO | WO 91/03267 | 3/1991 |
| 5,593,680 A | 1/1997 | Bara et al. ................... 424/401 | | WO | WO 91/09629 | 7/1991 |
| 5,595,723 A | 1/1997 | Quay ........................ 424/9.5 | | WO | WO 91/12823 | 9/1991 |
| 5,605,673 A | 2/1997 | Schutt et al. .............. 424/9.51 | | WO | WO 91/15244 | 10/1991 |
| 5,606,973 A | 3/1997 | Lambert et al. ........ 128/662.02 | | WO | WO 92/05806 | 4/1992 |
| 5,612,057 A | 3/1997 | Lanza et al. ................. 424/450 | | WO | WO 92/10166 | 6/1992 |
| 5,612,318 A | 3/1997 | Weichselbaum et al. ...... 514/44 | | WO | WO 92/11873 | 7/1992 |
| 5,614,169 A | 3/1997 | Klaveness et al. ......... 424/9.52 | | WO | WO 92/15284 | 9/1992 |
| 5,620,689 A | 4/1997 | Allen et al. ................ 424/178.1 | | WO | WO 92/17212 | 10/1992 |
| 5,626,833 A | 5/1997 | Schutt et al. ............... 424/9.52 | | WO | WO 92/17213 | 10/1992 |
| 5,639,443 A | 6/1997 | Schutt et al. ............... 424/9.52 | | WO | WO 92/17436 | 10/1992 |
| 5,639,473 A | 6/1997 | Grinstaff et al. ............. 424/450 | | WO | WO 92/17514 | 10/1992 |
| 5,641,765 A | 6/1997 | Holt et al. .................... 514/169 | | WO | WO 92/21382 | 12/1992 |
| 5,643,553 A | 7/1997 | Schneider et al. ......... 424/9.52 | | WO | WO 92/22247 | 12/1992 |
| 5,648,095 A | 7/1997 | Illum et al. ................. 424/489 | | WO | WO 92/22249 | 12/1992 |
| 5,648,098 A | 7/1997 | Porter ........................ 424/490 | | WO | WO 92/22298 | 12/1992 |
| 5,672,585 A | 9/1997 | Pierschbacher et al. ....... 514/11 | | WO | WO 93/00933 | 1/1993 |
| 5,676,928 A | 10/1997 | Klaveness et al. ......... 424/9.32 | | WO | WO 93/05819 | 1/1993 |
| 5,679,459 A | 10/1997 | Riess et al. .............. 428/402.2 | | WO | WO 93/06869 | 4/1993 |
| | | | | WO | WO 93/13809 | 7/1993 |

| WO | WO 93/17718 | 9/1993 |
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 96/04018 | 2/1996 |
| WO | WO 96/09793 | 4/1996 |
| WO | WO 96/36286 | 11/1996 |
| WO | WO 96/40281 | 12/1996 |
| WO | WO 96/40285 | 12/1996 |
| WO | WO 98/00172 | 1/1998 |
| WO | WO 99/13919 | 3/1999 |
| WO | WO 99/39738 | 8/1999 |

OTHER PUBLICATIONS

Mayer et al., "Vesicles of Variable Size Produced by a Rapid Extrusion Procedure", *Biochim. et Biophys. Acta*, 1986, 858, 161–168.

Cheng et al., "The Production and Evaluation of Contrast–Carrying Liposomes Made with an Automatic High Pressure System", *Invest. Radiol.*, 1987, 22, 47–55.

Jain et al., "Facilitated Transport", *Introduction to Biological Membranes*, John Wiley and Sons, N.Y., 1980, Ch. 9, 192–231.

Sigel, H., (ed.), *Metal Ions in Biological Sytems: Antibiotics and Their Complexes*, Marcel Dekker, N.Y., 1985, 19, 1–387.

Nayar et al., "Generation of Large Unilamellar Vesicles From Long–chain Saturated Phosphatidylcholines by Extrusion Technique", *Biochim. et Biophys. Acta*, 1989, 986, 200–206.

Hope et al., "Generation of Multilamellar and Unilamellar Phospholipid Vesicles", *Chem. Phys. Lipids*, 1986, 40, 89–107.

Mattrey et al., "Perflurochemicals as US Contrast Agents for Tumor–Imaging and Hepatosplenography: Preliminary Clinical Results", *Radiology*, 1987, 163, 339–343.

Mattrey et al., "Perfluorocytylbromide: A Liver/Spleen–Specific and Tumor Imaging Ultrasound Contrast Material", *Radiology*, 1982, 145, 759–762.

Keller et al., "Successful Left Ventricular Opacification Following Peripheral Venous Injection of Sonicated Contrast Agent: An Experimental Evaluation", *LV Contrast Echocardiography*, 1987, 114(3), 570–575.

Feinstein et al., "Two–Dimensional Contrast Echocardiography, I: In Vitro Development and Quantitative Analysis of Echo Contrast Agents", *JACC*, 1984, 3(1), 14–20.

Ten Cate et al., "Two–Dimensional Contrast Echocardiography, II: Transpulmonary Studies", *JACC*, 1984, 3(1), 21–27.

Unger et al., "Hepatic Metastases: Liposomal Gd–DTPA–enhanced MR Imaging", *Radiology*, 1989, 171, 81–85.

Deamer et al., "Permeability of Lipid Bilayers to Water and Ionic Solutes", *Chem. Phys. Lipids*, 1986, 40, 167–188.

Gutknecht et al., "Diffusion of Carbon Dioxide Through Lipid Bilayer Membranes: Effect of Carbonic Anhydrase, Bicarbonate, and Unstirred Layers", *Chemical Abstracts*, 1977, 87, 34772q.

Scarpa et al., "Cation Permeability of Liposomes as a Function of the Chemical Composition of the Lipid Bilayers", *Biochimica et Biophysica Acta*, 1971, 241, 789–797.

MacNaughton et al., "Effects of Gaseous Anesthetics and Inert Gases on the Phase Transition in Smectic Mesophases of Dipalmitoyl Phosphatidylcholine", *Biochim. et Biophys. Acta*, 1980, 597, 193–198.

Tilcock et al., "Liposomal Gd–DTPA: Preparation and Characterization of Relaxivity", *Radiology*, 1989, 171, 77–80.

Mann et al., "Formation of Iron Oxides in Unilamellar Vesicles", *J. Colloid Interface Sci.*, 1988, 122(2), 326–335.

Anderson et al., "Manganese (III) Complexes in Oxidative Decarboxylation of Acids", *J. Am. Chem. Soc.*, 1970, 92(8), 2450–2460.

Muhlradt et al., "Vitamin B6 Analogs: An Improved Synthesis of 5–Deoxypyridoxal", *New Compounds*, 1967, 10, 129–130.

Chapman D., "Physicochemical Properties of Phospholipids and Lipid Water Systems", *Liposome Technology*, Gregoriadis, G., (ed.), CRC Press, Boca Raton, FL, 1984, 1, 1–18.

Violante et al., "Particulate Suspensions as Ultrasonic Contrast Agents for Liver and Spleen", *Inv. Rad.*, 1988, 23, S294–S297.

Fritzsch et al., "Preclinical and Clinical Results with an Ultrasonic Contrast Agent", *Inv. Rad.*, 1988, 23, S302–S305.

Brochure, *Experience*, Sonicator™, Heat Systems–Ultrasonics, Inc., 1987, 3 pages.

Ostro, M. (ed.), "Liposomes", Marcel Dekker, Inc., New York, 1983, 102–103.

Fukuda et al., "Polymer–Encased Vesicles Derived from Diotadecyldimethylammonium Methacrylate", *J. Am. Chem. Soc.*, 1986, 108, 2321–2327.

Regen, "Polymerized Vesicles", *J. Am. Chem. Soc.*, 1980, 102, 6638–6640.

Rose, A. et al., (eds.), "The Condensed Chemical Dictionary", Seventh Edition, Reinhold Publishing Corporation, New York, 1966, 728 and 743.

Belkyh, A.G., "Effect of Radiographic Contrast Agents on the Structure and Function of Hepatocyte Plasma Membranes", *Farmakol Toksikol. (MOSC)*, 1981, 44(33), 322–326 (abstract).

Vion–Dury, J. et al., "Liposome–Mediated Delivery of Gadolinium Diethylenetriaminepentaacetic Acid to Hepatic Cells a Phosphorus–31 NMR Study", *J. Pharmacol. Exper. Ther.*, 1989, 250(3), 1113–1118 (abstract).

Zalutsky, M.R. et al., "Characterization of Liposomes Containing Iodine–125–Labeled Radiographic Contrast Agents", *Invest. Radiol.*, 1987, 22(2), 141–147 (abstract).

Crowe et al., "Preservation of Freeze–Dried Liposomes by Trehalose", *Archives Biochem. Biophys.*, 1985, 242(1), 240–247.

Crowe et al., "Preservation of Structural and Functional Activity in Lyophilized Sarcoplasmic Reticulum", *Archives Biochem. Biophys.*, 1983, 220(2) 477–484.

Dorland's Illustrated Medical Dictionary, 27th Edition, W.B. Saunders Company, Philadelphia, 1988, 946.

Gregoriadis, G., (Ed.), "Preparation of Liposomes", *Liposome Technology*, vol. I, CRC Press, Inc., Boca Raton, FL, 1984, 1–18, 30–35, 51–65 and 79–107.

Madden et al., "The accumulation of drugs within large unilamellar vesicles exhibiting a proton gradient: a survey", *Chem. Phys. Lipids*, 1990, 53, 37–46.

Sinkula et al., "Rationale for Design of Biologically Reversible Drug Derivatives: Prodrugs", *J. Pharm. Sci.*, 1985, 64 181–210.

Shiina et al., "Hyperthermiably Low–frequency Synthesized Ultrasound", *IEEE Engineering*, 1988, 2, 879–880 (abstract).

McAvoy et al., "Ultrasonics Symposium Proceedings", *IEEE Engineering*, 1989, 2, 677–1248 (abstract).

Chapman et al., "Biomembrane Phase Transitions", *J. Biol. Chem.*, 1974, 249(8), 2512–2521.

Hug et al., "Liposomes for the Transformation of Eukaryotic Cells", *Biochim. et Biophys. Acta*, 1991, 1097, 1–17.

Marsh, *CRC Handbook of Lipid Bilayers*, CRC Press, Boca Raton, FL, 1990, 139–141.

Szoka et al., "Procedure of preparation of liposomes with large internal aqueous space and high capture by reverse–phase evaporation", *Proc. Natl. Acad. Sci. USA*, 1978, 75(9), 4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamallae of Swollen Phospholipids", *J. Mol. Biol.*, 1965, 13, 238–252.

Carson et al., "Ultrasonic Power and Intensities Produced by Diagnostic Ultrasound Equipment", *Ultrasound Med. & Biol.*, 1978, 341–350.

Kost et al., "Ultrasonic Modulated Drug Delivery Systems", *Polymers in Medicine II: Biomedical and Pharmaceutical Applications*, Chiellini et al. (Eds.), Plenum Press, New York and London, 1985, 387–396.

deGier et al., "Relations Between Liposomes and Biomembranes", *Annals New York Acad. Sci.*, 1978, 308, 85–99.

Felgner et al., "Lipofection: A highly efficient, lipid–mediated DNA–transfection procedure", *Proc. Natl. Acad. Sci. USA*, 1987, 84, 7413–7417.

Gabizon et al., "Liposome formulations with prolonged circulation time in blood and enhanced uptake by tumors", *Proc. Natl. Acad. Sci. USA*, 1988, 85, 6949–6953.

Garelli et al., "Incorporation of new amphiphilic perfluorarlkylated biprydine platinum and palladium complexes into liposomes: stability and structure–incorporation relationships", *Biochim. et Biophys. Acta*, 1992, 1127, 41–48.

Kawai et al., "New Procedure for DNA Transfection with Polycation and Dimethyl Sulfoxide", *Mol. Cell. Biol.*, 1984, 4(6), 1172–1174.

Kuo et al., "Metallocene Antitumor Agents. Solution and Solid–State Molybdenocene Coordination Chemistry of DNA Constituents", *J. Am. Chem. Soc.*, 1991, 113, 9027–9045.

MacDonald, "Genetic engineering of animal cells", *Mammalian Cell Biotechnology: A Practical Approach*, M. Butler (Ed.), Oxford University Press, New York, 1991, 57–70.

Mathiowitz et al., "Photochemical Rupture of Microcapsules: A Model System", *J. Applied Poly. Sci.*, 1981, 26, 809–822.

May et al., "Cationic Liposomes Enable Bovine Herpesvirus Type 2 DNA to Infect Cells", *Acta virol.*, 1991, 35, 107.

Poznanzky et al., "Biologial Approaches to the Controlled Delivery of Drugs: A Critical Review", *Pharmacol. Rev.*, 1984, 36(4), 277–336.

Sato et al., "Recent Aspects in the Use of Liposomes in Biotechnology and Medicine", *Prog. Lipid Res.*, 1992, 31(4), 345–372.

Simons et al., "Antisense c–myb oligonucleotides inhibit intimal arterial smooth muscle cell accumulation in vivo", *Nature*, 1992, 359, 67–70.

Thompson, L., "At Age 2, Gene Therapy Enters a Growth Phase", *Science*, 1992, 258, 744–746.

Trubetskoy et al., "Cationic liposomes enhance targeted delivery and expression of exogenous DNA medidated by N–terminal modified poly(L–lysine)–antibody conjugate in mouse lung endothelial cells", Biochim. et Biophys. Acta, 1992, 1131, 311–313.

Umemura et al., "Studies on Sonodynamic Cancer Therapy", *IEEE*, 1992, 354–355.

Williams, "Human Gene Therapy: Searching for Better Vectors", *ASM News*, 1992, 58(2), 67–69.

Woodle et al., "Versatility in lipid compositions showing a prolonged circulation with sterically stabilized liposomes", *Biochim. et Biophys. Acta*, 1992, 1105, 193–200.

Zhou et al., "Targeted delivery of DNA by liposomes and polymers", *J. Control. Release*, 1992, 19, 269–274.

Mathiowitz et al., "Polyanhydride Microspheres as Drug Carriers", *J. Appl. Poly. Sci.*, 1988, 35, 755–774.

Sankaram et al., "Cholesterol–Induced Fluid–Phase Immiscibility in Membranes", *Proc. Natl. Acad. Sci. USA*, 1991, 88, 8686–8690.

*Scientific Apparatus Catalog 92/93*, VWR Scientific, "Syringes", 1511–1513; "Filtration, Syringe Filters", 766–768; "Filtration, Membranes", 750–753; "Filtration, Filter Holders", 744, 1991.

Gramiak et al., "Detection of Intracardiac Blood Flow by Pulsed Echo–Ranging", *Radiology*, 1971, 415–418.

Feigenbaum et al., "Identification of Ultrasound Echoes from the Left Ventricle by Use of Intracardiac Injections of Indocyanine Green", *Circulation*, 1970, vol. XL1, 615–621.

Santaella et al., "Extended In Vivo Blood Circulation Time of Fluorinated Liposomes", *FEBS 13463*, 1993, 336(3), 481–484.

Brown et al., "Transdermal Delivery of Drugs", *Ann. Rev. Med.*, 1988, 39, 221–229.

Moseley, et al., "Microbubbles: A Novel MR Susceptibility Contrast Agent", Napa, California Meeting of the Society for Magnetic Resonance in Medicine, 1991, 1020, Abstract.

Ter–Pogossian et al., "Physical Principles and Instrumentation", *Computed Body Tomography*, Lee et al. (Eds.), Raven Press, New York, 1988, Ch. 1, 1–7.

Aronberg, "Techniques", *Computed Body Tomography*, Lee et al., (Eds.), Raven Press, New York, 1988, Ch. 2, 9–36.

Miller, "Ultrasonic detection of resonant cavitation bubbles in a flow tube by their second–harmonic emissions," *Ultrasonics*, 1981, 217–224.

Dittrich, "Cardiac Muscle Ischemia and Infarction", *The Second Annual International Symposium on Contrast Agents in Diagnostic Ultrasound*, Atlantic City, NJ, May 7, 1996, 3 pages, abstract.

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ, May 7, 1996, 6 pages, abstract.

Schutt et al., "Osmotically Stabilized Microbubble Sonographic Contrast Agents", *Acad. Radiol.*, 1996, 3(Suppl. 2), S188–S190.

Frézard et al., "Permeability and stability in buffer and in human serum of fluorinated phospholipid–based liposomes", *Biochim. et Biophys. Acta*, 1994, 1192, pp. 61–70.

Frézard, et al., "Fluorinated Phosphlipid–Based Vesicles as Potential Drug Carriers: Encapsulation/Sustaining of Drugs and Stability in Human Serum", *Art, Cells, Blood Subs., and Immob. Biotech.*, 1994, 22(4), 1403–1408.

Chang et al., "Semipermeable Aqueous Microcapsules", *Canadian J. Phys. Pharm.*, 1966, 44, 115–128.

Chang, et al., "Semipermeable Microcapsules", *Science*, 1964, 146, 524–525.

Deasy, *Microencapsulation and Related Drug Processes*, Marcel Dekker, Inc., NY, 1983, vol. 20, Chs. 9 and 10, 195–240.

Yeung et al., "Preparation of Microencapsulated Liposomes", *J. Microencapsulation*, 1988, 5(4), 331–337.

Mattrey et al., "Gas Emulsions as Ultrasound Contrast Agents; Preliminary Results in Rabbits and Dogs", *Invest. Radiol.*, 1994, 29(Suppl. 2), S139–S141.

Meltzer et al., "Transmission of Ultrasonic Contrast Through the Lungs", *Ultrasound Med. Biol.*, 1981, 7(4), 377–384.

PR Newswire, Apr. 1, 1986, 1 page.

Swanson et al., "Enhancement Agents for Ultrasound: Fundamentals", *Pharmaceuticals In Medical Imaging*, 1990, Ch. 22, 682–687.

Ophir et al., "Contrast Agents in Diagnostic Ultrasound", *Ultrasound Med. Biol.*, 1989, 15(4), 319–333.

Jacobs, "Intraocular gas measurement using A–scan ultrasound", *Current Eye Research*, 1986, 5(8), 575–578.

Lincoff et al., "Intravitreal Expansion of Perfluorocarbon Bubbles", *Arch. Ophthalmol.*, 1980, 98, 1646.

Lincoff et al., "Intravitreal Longevity of Three Perfluorocarbon Gases", *Arch. Ophthalmol.*, 1980, 98, 1610–1611.

Lincoff et al., "The Perfluorocarbon Gases in the Treatment of Retinal Detachment", *Ophthalmology*, 1983, 90(5), 546–551.

Gardner et al., "A Survey of Intraocular Gas Use in North America", *Arch. Ophthalmol.*, 1988, 106, 1188–1189.

Unger et al., "Liposomal MR Contrast Agents", *J. Liposome Research*, 1994, (4(2), 811–834.

Feinstein, S., "Myocardial Perfusion Imaging: Contrast Echocardiography Today and Tomorrow," *JACC*, 1986, 8(1), 251–253.

Keller et al., "The Behavior of Sonicated Albumin Microbubbles Within the Microcirculation: A Basis for Their Use During Myocardial Contrast Echocardiography", *Circul. Res.*, 1989, 65(2), 458–465.

Lincoff et al., "Perfluoro–n–butane: A Gas for Maximum Duration Retinal Tamponade," *Arch Opthalmology*, 1983, 101, 460–462.

*Remington's Pharmaceutical Sciences*, Hoover (Ed.), Mack Publishing Company, Easton, PA, 1975, pp. 295–298; 736; 1242–1244.

*Handbook of Pharmaceutical Excipients*, "Methylecllulose", American Pharmaceutical Association, Washington, D.C. and The Pharmaceutical Society of Great Britain, London, England, 1986, 181–183.

Barnhart et al., "Characteristics of Albunex™: Air–Filled Microspheres for Echocardiography Contrast Enhancement," *Invest. Radiol.*, 1990, 25, S162–164.

Levene et al., "Characterization of Ablunex™," *J. Acoust. Soc. Am.*, 1990, 87(Suppl. 1), 569–570.

Miller et al., "Physiochemical Approaches to the Mode of Action of General Anesthetics," *J. Amer. Soc. Anesthesiol.*, 1972, 36(4), 339–351.

"Properties and Applications of the 'Freon' Fluorocarbons" in DuPont Freon Technical Bulletin B–2, E.I. DuPont de Nemours and Company, Wilmington, DE, 1964, 1–11.

"'Freon' Fluorocarbons: Properties and Applications" in DuPont Technical Bulletin G–1, E.I. DuPont de Nemours and Company, Wilmington, DE, 1987, 1–10.

"Encyclopedia of Polymer Science and Engineering," John Wiley & Sons, New York, 1985, 1, 164–169.

Kroschwitz, J. (Ed.),*Concise Encyclopedia of Polymer Science and Engineering*, John Wiley & Sons, New York, 1990, 12–13.

Wheatley et al., "Contrast Agents for Diagnostic Ultrasound: Development and Evaluation of Polymer–Coated Microbubbles," *Biomaterials*, 1990, 11, 713–717.

Villanueva et al., "Characterization of Spatial Patters of Flow Within the Reperfused Myocardium by Myocardial Contrast Echocardiography", *Circulation*, 1993, 88(6), 2596–2606.

Desir et al., "Assessment of regional myocardial perfusion with myocardial contrast echocardiography in a canine model of varying degress of coronary stenosis", *Am. Heart J.*, 1994, 127(1), 56–63.

Sekins et al., "Lung Cancer Hyperthermia via Ultrasound and PFC Liquids", *Published in Proceedings of 5th International Symposium on Hyperthermic Oncology*, Kyoto, Japan, Aug. 29–Sep. 3, 1998, 2 pages.

Pietersen, "A New Warning System for Fires of Electrical Origin", *CERN European Organization for Nuclear Research, Health and Safety Division*, Mar. 1977, 1–5.

Nomura et al., "US Contrast Enhancement of Hepatic Tumor with Helium Gas Microbubbles: A Preliminary Report", *Jpn. J. Med. Ultrasonics*, 1991, 18(5), 28–35 (Japanese with English language abstract).

Lindner et al., "Myocardial Perfusion Characteristics and Hemodynamic Profile of MRX–115, a Venous Echcocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology*, 1994, 29(10), 897–903.

Abraham et al., "Function and Regulation of the Murine Lymphocyte CD2 Receptor", *J. Leukocyte Biol.*, 1991, 49, 329–341.

Al–Muhammad et al., "Studies on the formulation and in vivo release of ophthalmic liposomes containing dexamethasone sodium phosphate", *J. Microencapsulation*, 1996, 13(2), 123–130.

Allcock, H.R., "Covalent Linkage of Proteins to Surface–Modified Poly(organophosphazenes): Immobilization of Glucose–6–Phosphate Dehydrogenase and Trypsin", *Macromolecules*, 1986, 19, 1502–1508.

Allcock, H.R., "Schiff Base Coupling of Cyclic and High–Polymeric Phosphazenes to Aldehydes and Amines: Chemotherapeutic Models", *Macromolecules*, 1981, 14, 1616–1622.

Bloemberger, N., "Proton Relaxation Times in Paramagnetic Solutions", *J. Chem. Phys.*, 1957, 27(2), 572–573 and 595–596.

Canfield et al., "Incorporation of β–Carotene into Mixed Micelles", *Methods in Enzymology*, 1990, 189, 418–422.

Cesano et al., "Treatment of experimental glioblastoma with a human major histocompatibility complex nonrestricted cytotoxic T cell line", *Cancer Res.*, 1995, 55(1), 96–101 (Abstract Only).

Cullen et al., "Sequence Requirements for Ligand Binding and Cell Surface Expression of the TAC Antigen a Human Interleukin Receptor", *J. Biol. Chem.*, 1988, 263(10), 4900–4906 (Abstract Only).

De Jager, R. et al., "Current Status of Cancer Immunodetection with Radiolabeled Human Monoclonal Antibodies", *Seminars in Nuclear Med.*, 1993, 23(2), 165–179.

Elgorab et al., "Solubilization of β–Carotene and Retinol into Aqueous Solutions of Mixed Micelles", *Biochem. Biophys. Acta.*, 1973, 306, 58–66.

Falconi et al., "Oral Long–Lasting Estrogenic Activity of Estradiol 3–Benzoate 17–Cyclooctenyl Ether", *Steroids*, 1972, 20(5), 627–638.

Farsh et al., "In–vivo studies in the treatment of oral ulcers with liposomal dexamethasone sodium phosphate", *J. Microencapsulation*, 1996, 13(5), 537–544.

Fedorak et al., "A novel colon–specific steroid prodrug enhances sodium chloride absorption in rat colitis", *Am. J. Physiol.*, 1995, 269, G210–218.

Fremont et al., "Biophysical studies of T–cell receptors and their ligands", *Curr. Opin. Immunol.*, 1996, 8, 93–100.

Gaffen et al., "Signaling through the interleukin 2 receptor beta chain activates a STAT–5–like DNA–binding activity", *Proc. Natl. Acad. Sci. USA*, 1995, 92(16), 7192–7196 (Abstract Only).

Gioanni, J. et al., "Characterization of a New Surface Epitope Specific for Human Epithelial Cells Defined by a Monoclonal Antibody and Application to Tumor Diagnosis", *Cancer Res.*, 1987, 47, 4417–4424.

Goundalkar et al., "Chemical Modification of Triamcinolone Acetonide to Improve Liposomal Encapsulation", *J. Pharm. Sciences*, 1984, 73(6), 834–835.

Hemar et al., "Endocytosis of Interleukin 2 Receptors in Human T Lymphocytes: Distinct Intracellular Localization and Fate of the Receptor α, β, and γ Chains", *J. Cell Biol.*, 1995, 129, 55–64.

Hochhaus et al., "A Selective HPLC/RIA for Dexamethasone and its Prodrug Dexamethasone–21–sulphobenzoate Sodium in Biological Fluids", *Biomed. Chrom.*, 1992, 6, 283–286.

Hori et al., "Characteristics of the IL–2 Recpetor Expressed on Large Granular Lymphocytes from Patients wtih Abnormally Expanded Large Granular Lymphocytes Implication of a Non–Tac IL–2 Binding Peptide", *J. Immunol.*, 1988, 140(12), 4199–4203 (Abstract Only).

Kawabata, K. et al., "Effect of second–harmonic superimposition on efficient induction of sonochemical effect", *Ultrasonics Sonochemistry*, 1966, 3, 1–5.

Kersh et al., "Structural Basis for T Cell Recognition of Altered Peptide Ligands: A Single T Cell Receptor Can Productively Recognize a Large Continuum of Related Ligands", *J. Exp. Med.*, 1996, 184, 1259–1268.

Kuo et al., "Structure–Function Relationships for the Interleukin 2–Receptor System I. Localization of a Receptor Binding Site on Interleukin 2", *J. Immunol.*, 1986, 137(5), 1538–1543 (Abstract Only).

Ledin cer and Mitscher (eds.), *Organic Chemistry of Drug Synthesis*, vol. 1, Chapter 10.

Legrue et al., "The Role of Receptor–Ligand Endocytosis and Degradation in Interleukin–2 Signaling and T–Lymphocyte Proliferation", *Lymphokine Cytokine Res.*, 1991, 10(6), 431–436.

Lopez–Garcia et al., "Intra–articular therapy of experimental arthritis with a derivative of triamcinolone acetonide incorporated in liposomes", *J. Pharm. Pharmacol.*, 1993, 45, 576–578.

Lubinski et al., "Increased Binding of IL–2 and Increased IL–2 Receptor Messenger RNA Synthesis are Expressed by an NK–Like Cell Line in Response to IL–1", *J. Immunol.*, 1988, 140(6), 1903–1909 (Abstract Only).

Lundblad, R.L., "The Chemical Cross–Linking of Peptide Chains", *Techniques in Protein Modification*, CRC Press, Chapter 15, 249–267.

McLeod et al., "A Glucocorticoid Prodrug Facilitates Normal Mucosal Function in Rat Colitis Without Adrenal Suppression", *Gastroenterol.*, 1994, 106, 405–413.

Merimsky, O. et al., "Antigens and Antibodies in Malignant Melanoma", *Tumor Biol.*, 1994, 15, 188–202.

Miedel et al., "Structural Analysis of Recombinant Soluble Human Interleukin", *Biochem. Biophys. Res. Commun.*, 1988, 154(1), 372–379 (Abstract Only).

Miescher et al., "CCLXXVII. The Activation of the Male Sex Hormones. II.", *Activation of Male Sex Hormones*, 1936, 1977–1990.

Moreau et al., "Characterization of a monoclonal antibody directed against the NH2 terminal area of interleukin–2 (IL–2) and inhibiting specifically the binding of IL–2 to IL–2 receptor beta chain (IL–2R–beta)", *Mol. Immunol.*, 1995, 32, 14–15 (Abstract Only).

Nicol, L. et al., "Immunoscintigraphie Does Mélanomes Malins", *Pathologie Biologie*, 1990, 38(8), 866–869 (Summary of article in English).

O'Connor et al., "Growth Factor Requirements of Childhood Acute T–Lymphoblastic Leukemia: Correlation Between Presence of Chromosomal Abnormalities and Ability to Grow Permanently In Vitro", *Blood*, 1991, 77(7), 1534–1545.

Reexamination of U.S. Patent No. 5,527,521, Reexam Control No. 90/004,719.

Reexamination of U.S. Patent No. 5,547,656, Reexam Control No. 90/004,720.

Shahinian, S. et al., "A novel strategy affords high–yield coupling of antibody Fab' fragments to liposomes", *Biochimica et Biophysica Acta*, 1995, 1239, 157–167.

Solomon, I., "Relaxation Processes in a System of Two Spins", *Phys. Rev.*, 1955, 99(2), 559–565.

Sutherland et al., "Color Doppler Myocardial Imaging: A New Technique for the Assessment of Myocardial Function", *J. Am. Soc of Echocardiogr*, 1994, 7(5), 441–458.

Tagliaferri, P. et al., "Pharmacological modulation of peptide growth factor receptor expression on tumor cells as a basis for cancer therapy", *Anti–Cancer Drugs*, 1994, 5, 379–393.

Thorpe, P.E. et al., "Antibody–directed targeting of the vasculature of solid tumors", *Breast Cancer Res. and Treatment*, 1995, 36, 237–251.

Tsudo et al., "Contribution of a P75 Interleukin 2 Binding Peptide to a High–Affinity Interleukin 2 Receptor Complex", *Proc. Natl. Acad. Sci. USA*, 1987, 84(12), 4215–4218 (Abstract Only).

Tsuji, Y. et al., "Identification of Two Different Surface Epitopes of Human Ovarian Epithelial Carcinomas by Monoclonal Antibodies", *Cancer Res.*, 1985, 45, 2358–2362.

Ulendorf, "Physics of Ultrasound Contrast Imaging: Scattering in the Linear Range", *IEEE Transactions on Ultrasonics, Ferroelectrics, and Frequency Control*, 1994, 41(1), 70–79.

Van Dongen et al., "Progress in radioimmunotherapy of head and neck cancer", *Oncology Reports*, 1994, 1, 259–264.

Wallner et al., "Primary Structure of Lymphocyte Function–Associated Antigen 3 (LFA–3): The Ligand of the T Lymphocyte CD2 Glycoprotein", *J. Experimental Med.*, 1987, 166, 923–932.

Weiss et al., "Cell Surface Molecules and Early Events Involved in Human T Lymphocyte Activation", *Adv. Immunol.*, 1987, 41, 1–38.

Wiegent et al., "The HTLV–III Envelope Protein Contains a Hexapeptide Homologous to a Region of Interleukin–2 That Binds to the Interleukin–2 Receptor", *Biochem. Biophys. Res. Commun.*, 1986, 139(1), 367–374.

Wu, T.Z., "Immunology of the human papilloma virus in relation to cancer", *Curr. Opin. In Immunol.*, 1994, 6, 746–754.

Xueyong, Z. et al., "Use of MG Series Monoclonal Antibodies in the Diagnosis and Experimental Targeting Therapy of Gastric Cancer", *Chin. Med. Sci. J.*, 1991, 6(1), 56–59.

U.S. patent application Ser. No. 08/887,215 filed Jul. 2, 1997.

Lejbkowicz et al., "The response of normal and malignant cells to ultrasound in vitro", Database *BIOSIS*, No. 1993:95122245 (abstract only).

Jackson et al., "Effect of ultrasound therapy on repair of Achilles tendon injuries in rats", *Med. Sci. Sports Exercise*, 1991, 23(2), 171–176.

Maxwell, "Therapeutic Ultrasound: Its Effects on the Cellular and Molecular Mechanisms of Inflammation and Repair", *Physiotherapy*, 1992, 78(6), 421–426.

Tuncay et al., "Expression of Genes Associated with Tissue Remodeling Upon Ultrasound Perturbation in the Gingival Fibroblast", *J. Dental Res.*, 1996, 75, 143, (abstract only).

Wang et al., "Low Intensity Ultrasound Treatment Increases Strength in a Rat Femoral Fracture Model", *J. Orthopaedic Res.*, 1994, 12(1), 40–47.

Yang et al., "Exposure to Low–Intensity Ultrasound Increases Aggrecan Gene Expression in a Ret Femur Facture Model", *J. Orthopaedic Res.*, 1996, 14(5), 802–809.

Young et al., "Effect of therapeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

Chortkoff, B.S. et al., "Pharmacokinetics Do Not Explain the Absense of an Anesthetic Effect of Perfluoroproprane or Perfluoropentane," *Anesth. Analg.*, 1994, 79, 234–237.

Sharma, S.K. et al., "Emulsification Methods For Perfluorochemicals," *Drug Develop. Indust. Pharm.*, 1988, 14(15–17), 2371–2376.

Tilcock, C. et al., "PEG–coated Lipid Vesicles with Encapsulated Technetium–99m as Blood Pool Agents for Nuclear Medicine," *Nucl. Med. Biol.*, 1994, 21(2), 165–170.

Tilcock, C. et al., "$^{99m}$Tc–labeling of Lipid Vesicles Containing the Lipophilic Chelator PE–DTTA: Effect of Tin–to–chelate Ratio, Chelate Content and Surface Polymer on Labeling Efficiency and Biodistribution Behavior," *Nucl. Med. Biol.*, 1994, 21(1), 89–96.

Zarif, L. et al., "Synergistic Stabilization of Perfluorocarbon–Pluronic F–68 Emulsion by Perfluoralkylated Polyhydroxylated Surfactants," *JAOCS*, 1989, 66(10), 1515–1523.

Kinsler, L. E., et al., *Fundamentals of Acoustics*, $3^{rd}$ Ed., 1982, 228–331.

Ring, J., et al., "Humanalbuminunverträglichkeit: klinische und immunologische untersuchungen," *Clinical Weekly*, 1974, 52, 595–598, Abstract only.

Robinson, et al., F.J. Fry (ed.), "Ultrasound: its applications in medicine and biology," *Elsevier Scientific Publishing Company*, 1978, vol. 3, Chap. XI, 593–596.

Wells, P.N.T., "Pulse–echo methods," *Biomedical Ultrasonics*, Academic Press, 1977, 209–220.

Porter, T.R., et al., "Multifold sonicated dilutions of albumin with fifty percent dextrose improve left ventricular contrast videointensity after intravenous injuction in human beings," *J. Am. Soc. Echocardiogr*, XP 000590864, Sep./Oct. 1994, 7(5), 465–471.

Porter, T.R., et al., "Noninvasive identification of acute myocardial ischemia and reperfusion with contrast ultrasound using intravenous perfluoropropane–exposed sonicated dextrose albumin," *Am. College of Cardiology*, XP 000590865, Jul. 1995, 26(1), 33–40.

Porter, T.R., et al., "Visually discernible myocardial echocardiographic contrast after intravenous injection of sonicated dextrose albumin microbubbles containing high molecular weight, less soluble gases," *Am. College of Cardiology*, Feb. 1995, 25(2), 509–515.

Srinivasan, S.K., et al., "Characterization of binding sites, extent of binding, and drug interactions of oligonucleotides with albumin," *Antisense Res. And Develop.*, 1995, 5, 131–139.

Xie, F., et al., "Acute myocardial ischemia and reperfusion can be visually identified non–invasively with intravenous perfluoropropane–enhanced sonicated dextrose albumin ultrasound contrast," *Circulation*, Oct. 1994, 90(4), Part 2, Abstract 2989, 1 page.

Frezard, F. et al., "Fluorinated phosphatidylcholine–based liposomes: $H^+/Na^+$ permeability, active doxorubicin encapsulation and stability in human serum", *Biochim. Biophys. Acta*, 1994, vol. 1194, No. 1, pp. 61–68.

Gross, U. et al., "Phospholipid vesiculated fluorocarbons–promising trend in blood susbstitutes", *Biomat., Art. Cell & Immob. Biotech.*, 1992, vol. 20, No. 2–4, pp. 831–833.

Riess, J.G. et al., "Fluorine in our arteries", *New J. Chem.*, 1995, vol. 19, No. 8–9, pp. 891–909 (English abstract only).

Riess, J.G. et al., "Introducing a new element—Fluorine— into the liposomal membrane", *Journal of Liposome Research, US, Marcel Dekker, New York*, Aug. 1995, vol. 5, No. 3, pp. 413–430.

Santaella, C. et al., "Extended in vivo blood circulation time of fluorinated liposomes", *FEBS Letters*, 1993, vol. 336, No. 3, pp. 481–484.

Trevino, L. et al., "Incorporation of a perfluoroalkylalkane ($R_F R_H$) into the phospholipid bilayer of DMPC liposomes results in greater encapsulation stability", *Journal of Liposome Research, US, Marcel Dekker, New York*, Jul. 1994, vol. 4, No. 2, pp. 1017–1028.

Zarif, L. et al., "Biodistribution and excretion of a mixed fluorocarbon–hydrocarbon "dowel" emulsion as determined by $19-_F$ NMR", *Art. Cells, Blood Subs., And Immob. Biotech.*, 1994, vol. 22, No. 4, pp. 1193–1198.

Porter, T. R., et al., "Thrombolytic Enhancement with Perfluorocarbon–exposed Sonicated Dextrose Albumin Microbubbles", *American Heart Journal*, Nov. 1996, vol. 132, No. 5, pp. 964–968.

* cited by examiner

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Leu Ser Pro Phe Pro Phe Asp Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Leu Ser Pro Phe Ala Phe Asp Leu
1               5

<210> SEQ ID NO 3
```

-continued

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Leu Ser Ala Phe Pro Phe Asp Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Leu Ser Pro Phe Pro Phe Asp Ala
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Ser Pro Phe Pro Phe Asp Leu Leu Leu
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Leu Ser Pro Phe Pro Phe Asp Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Gln Leu Ser Pro Ser Pro Asp Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Ser Ile Ile Asn Phe Glu Lys Leu
1               5

<210> SEQ ID NO 9
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 9

Leu Ser Pro Tyr Pro Phe Asp Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Ala Ser Pro Phe Pro Phe Asp Leu
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Ser Ser Phe Gly Ala Phe Gly Ile Phe Pro Lys
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic Construct

<400> SEQUENCE: 12

Ala Asn Glu Arg Ala Asp Leu Ile Ala Tyr Leu Lys Gln Ala Thr Lys
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Ala Asn Glu Arg Ala Asp Leu Ile Ala Tyr Leu Lys Gln Ala Thr Ala
1               5                   10                  15

Lys

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct

<400> SEQUENCE: 14

Ala Asn Glu Arg Ala Asp Leu Ile Ala Tyr Leu Lys Gln Ala Ser Lys
1               5                   10                  15

<210> SEQ ID NO 15
```

-continued

```
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa is azetidine

<400> SEQUENCE: 15

Trp Tyr Gln Xaa Tyr
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa is azetidine

<400> SEQUENCE: 16

Trp Pro Gly Trp Tyr Gln Xaa Tyr Ala Leu Pro Leu
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa is acetyl
<220> FEATURE:
<221> NAME/KEY: misc_feature
<222> LOCATION: (10)..(10)
<223> OTHER INFORMATION: Xaa is azetidine

<400> SEQUENCE: 17

Xaa Phe Glu Trp Pro Gly Trp Tyr Gln Xaa Tyr Ala Leu Pro Leu
1               5                   10                  15
```

LIPID SOLUBLE STEROID PRODRUGS

CROSS-REFERENCE TO RELATED APPLICATION

This application is a divisional of U.S. application Ser. No. 08/851,780, filed May 6, 1997, now U.S. Pat. No. 6,090,800.

FIELD OF THE INVENTION

The present invention is directed, inter alia, to novel lipid soluble steroid prodrugs, and to uses for the same.

BACKGROUND OF THE INVENTION

Prodrugs comprise inactive forms of active drugs where a chemical group is present on the prodrug which renders it inactive and/or confers solubility or some other property to the drug. Prodrugs are generally inactive, but once the chemical group has been cleaved from the prodrug, by heat, cavitation, pressure, and/or enzymes in the surrounding environment, the active drug is generated. Prodrugs may be designed as reversible drug derivatives and utilized as modifiers to enhance drug transport to site-specific tissues. Prodrugs are described in the art, for example, in Sinkula et al., *J. Pharm. Sci.*, (1975) 64:181–210, the disclosure of which is hereby incorporated herein by reference in its entirety.

Steroids encompass a variety of compounds having the general cyclopentanoperhydrophenanthrene ring system set forth below.

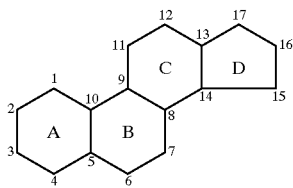

Steroids cause a variety of therapeutic effects, including enhanced anabolism, e.g., aldosterone, and anti-inflammatory effects, e.g., corticosteroids. Steroids such as cortisone and dexamethasone are potent immune suppressants and are used to treat conditions such as autoimmune diseases, organ transplant rejection, arthritis, skin, mucosal membrane and ophthalmic inflammation, as well as neoplastic conditions such as lymphoma. There are a variety of deleterious side effects associated with prolonged or high doses of steroids, such as fatigue, muscle wasting, bone loss resulting in pathologic fractures, salt and fluid retention, hypertension and heart disease, immunosuppression and infection, and avascular necrosis of the weight bearing articular surfaces of bones, such as the hips.

It is often difficult to deliver appropriate concentrations of steroids to target tissues. For example, in ophthalmic therapy, eye drops may be employed to deliver steroid hormones to the eye. However, the duration of action is short, and less than 3% of the steroid typically penetrates the cornea. As a partial solution to this problem, intraocular injections have been employed to increase the dosage.

The design of steroid prodrugs to date has been to increase the effective water solubility of the steroid. For example, Fedorak, et al., *Am. J. Physiol*, 269: G210–218 (1995), describe dexamethasone-β-D-glucuronide; McLoed, et al., *Gastroenterol.*, 106:405–413 (1994), describe dexamethasone-succinate-dextrans; and Hochhaus, et al, *Biomed Chrom.*, 6:283–286 (1992), describe dexamethasone-21-sulphobenzoate sodium and dexamethasone-21-isonicotinate.

A new way of delivering higher concentrations of steroids to the target tissue is needed to improve the efficacy of steroids as well as to lessen the side-effects associated with steroid use. The present invention is directed to these, as well as other, ends.

SUMMARY OF THE INVENTION

The present invention is directed to a compound comprising a steroid covalently bonded to a lipid moiety via a linking group.

In another embodiment, the compound comprising a steroid covalently bonded to a lipid moiety via a linking group may be of formula (I):

$$D\text{—}X\text{—}L \qquad (I)$$

wherein:
D is a steroid;
X is a linking group comprising an ester group, a carbamate group, a carbonyl group, a thioester group, a disulfide group, an ether group, an anhydride group, or an amide group; and
L is a lipid moiety comprising an acyl, alkyl, alkylaryl, fluoroacyl, fluoroalkyl or fluoroalkylaryl group having from about 4 to about 40 carbon atoms.

In another embodiment, the compound comprising a steroid covalently bonded to a lipid moiety via a linking group may be a compound of the formula (II), which is within the scope of formula (I):

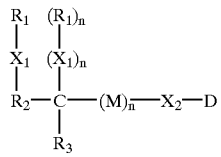

wherein:
each $X_1$ is independently a direct bond, —O—, —S—, —SO—, —SO$_2$—, —NR$_4$—, —X$_3$—C(=X$_4$)—, —C(=X$_4$)—X$_3$— or —C(=X$_4$)—;
$X_2$ is a direct bond, —C(=X$_4$)—, —R$_5$—X$_3$—C(=X$_4$)—, —R$_5$—C(=X$_4$)—X$_3$—, —X$_3$—C(=X$_4$)—R$_5$—, —C(=X$_4$)—X$_3$—R$_5$—, —X$_3$—R$_5$—C(=X$_4$)—X$_3$—, —C(=X$_4$)—R$_5$—C(=X$_4$)—, —C(=X$_4$)—R$_5$—C(=X$_4$)—X$_3$—, —R$_5$—X$_3$—C(=X$_4$)—R$_5$—C(=X$_4$)—X$_3$—, or —R$_5$—C(=X$_4$)—X$_3$—R$_5$—C(=X$_4$)—;
each $X_3$ is independently —O—, —NR$_4$— or —S—;
each $X_4$ is independently O or S;
M is —R$_5$—X$_3$—, —R$_5$—X$_3$—C(=X$_4$)—, —R$_5$—C(=X$_4$)—X$_3$—, —R$_5$—X$_3$—(YX$_4$)P(=X$_4$)—X$_3$— or —X$_3$—(YX$_4$)P(=X$_4$)—X$_3$—R$_5$—;
Y is a hydrogen atom or a pharmaceutically acceptable counter ion;
D is a steroid;
each n is independently an integer of 0 or 1;
each $R_1$ is independently an alkyl group of 1 to about 50 carbon atoms that is optionally substituted with one or more halogen atoms;
each $R_2$ is independently an alkylene group of 1 to about 30 carbon atoms that is optionally substituted with one or more halogen atoms;

each of $R_3$ and $R_4$ is independently =O, a hydrogen atom or an alkyl group of 1 to about 10 carbon atoms; and each $R_5$ is independently a direct bond or an alkylene group of 1 to about 30 carbon atoms.

Another embodiment of the invention is directed to a composition comprising, in an aqueous carrier, a steroid covalently bonded to a lipid moiety via a linking group.

Another embodiment of the invention provides a method of delivering a steroid to a patient comprising administering to the patient a composition comprising a steroid covalently bonded to a lipid moiety via a linking group. If desired, the method may further comprise the step of imaging the patient with diagnostic ultrasound to monitor the location of the composition in the patient. Also, if desired, the method may comprise the step of applying therapeutic ultrasound to the patient to facilitate localization of the steroid in a desired region of the patient.

The steroid covalently bonded to the lipid moiety via the linking group may be, for example, a compound of formula (I) or formula (II) above. The lipid moiety that is covalently bonded to the steroid via a linking group may form a vesicle or may be non-vesicular, as desired. The compositions of the invention may also comprise a wide variety of components, including, for example, one or more of gases, gaseous precursors, liquids, stabilizing materials, targeting ligands and other bioactive agents. The stabilizing materials may comprise, for example, lipids, proteins, polymers, surfactants, and the like. The stabilizing materials may be in the form of a vesicle or may be non-vesicular, forming, for example, an emulsion, suspension, dispersion or the like.

These and other aspects of the invention will become more apparent from the following detailed description.

DETAILED DESCRIPTION OF THE INVENTION

Definitions

As employed above and throughout the disclosure, the following terms, unless otherwise indicated, shall be understood to have the following meanings.

"Steroid" refers to steroids, steroid hormones, sterols, steroid analogs, and compounds with particular affinity to steroid or steroid-like receptors. Exemplary steroids include, for example, those having a cyclopentanoperhydrophenanthrene ring structure, diethylstilbestrol and analogs thereof, metyrapone and analogs thereof, and steroid analogs that maintain eutrogenic, androgenic, glucocorticoid, adrenocortoid, anabolic or birth control activity.

"Lipid" refers to a naturally-occurring, synthetic or semi-synthetic (i.e., modified natural) compound which is generally amphipathic. The lipids typically comprise a hydrophilic component and a hydrophobic component. Exemplary lipids include, for example, fatty acids, neutral fats, phosphatides, oils, glycolipids, surface-active agents (surfactants), aliphatic alcohols, waxes, terpenes and steroids. The phrase semi-synthetic (or modified natural) denotes a natural compound that has been chemically modified in some fashion.

"Vesicle" refers to an entity which is generally characterized by the presence of one or more walls or membranes which form one or more internal voids. Vesicles may be formulated, for example, from a stabilizing material such as a lipid, including the various lipids described herein, a proteinaceous material, including the various proteins described herein, and a polymeric material, including the various polymeric materials described herein. As discussed herein, vesicles may also be formulated from carbohydrates, surfactants, and other stabilizing materials, as desired. The lipids, proteins, polymers, surfactants and/or other vesicle forming stabilizing materials may be natural, synthetic or semi-synthetic. Preferred vesicles are those which comprise walls or membranes formulated from lipids. The walls or membranes may be concentric or otherwise. The stabilizing compounds may be in the form of one or more monolayers or bilayers. In the case of more than one monolayer or bilayer, the monolayers or bilayers may be concentric. Stabilizing compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of vesicles may be substantially solid (uniform), or they may be porous or semi-porous. The vesicles described herein include such entities commonly referred to as, for example, liposomes, micelles, bubbles, microbubbles, microspheres, lipid-coated bubbles, polymer-coated bubbles and/or protein-coated bubbles, microbubbles and/or microspheres, nanospheres, microballoons, microcapsules, aerogels, clathrate bound vesicles, hexagonal H II phase structures, and the like. The internal void of the vesicles may be filled with a wide variety of materials including, for example, water, oil, gases, gaseous precursors, liquids, fluorinated liquids, liquid perfluorocarbons, liquid perfluoroethers, and bioactive agents, if desired, and/or other materials. The vesicles may also comprise a targeting ligand, if desired.

"Liposome" refers to a generally spherical or spheroidal cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes formulated from non-ionic lipids may be referred to as niosomes.

"Micelle" refers to colloidal entities formulated from lipids. In certain preferred embodiments, the micelles comprise a monolayer, bilayer, or hexagonal H II phase structure.

"Aerogel" refers to generally spherical or spheroidal entities which are characterized by a plurality of small internal voids. The aerogels may be formulated from synthetic materials (for example, a foam prepared from baking resorcinol and formaldehyde), as well as natural materials, such as carbohydrates (polysaccharides) or proteins.

"Clathrate" refers to a solid, semi-porous or porous particle which may be associated with vesicles. In a preferred form, the clathrates may form a cage-like structure containing cavities which comprise one or more vesicles bound to the clathrate, if desired. A stabilizing material may, if desired, be associated with the clathrate to promote the association of the vesicle with the clathrate. Clathrates may be formulated from, for example, porous apatites, such as calcium hydroxyapatite, and precipitates of polymers and metal ions, such as alginic acid precipitated with calcium salts.

"Gas filled vesicle" refers to a vesicle having a gas encapsulated therein. "Gaseous precursor filled vesicle" refers to a vesicle having a gaseous precursor encapsulated therein. The vesicles may be minimally, partially, substantially, or completely filled with the gas and/or gaseous precursor. The term "substantially" as used in reference to the gas and/or gaseous precursor filled vesicles means that greater than about 30% of the internal void of the substantially filled vesicles comprises a gas and/or gaseous precursor. In certain embodiments, greater than about 40% of the internal void of the substantially filled vesicles comprises a gas and/or gaseous precursor, with greater than about 50% being more preferred. More preferably, greater than about 60% of the internal void of the substantially filled vesicles comprises a gas and/or gaseous precursor, with greater than about 70% or 75% being more preferred. Even more preferably, greater than about 80% of the internal void of the substantially filled vesicles comprises a gas and/or gaseous precursor, with greater than about 85% or 90% being still more preferred. In particularly preferred embodiments, greater than about 95% of the internal void of the vesicles comprises a gas and/or gaseous precursor, with about 100% being especially preferred. Alternatively, the vesicles may contain no or substantially no gas or gaseous precursor.

"Emulsion" refers to a mixture of two or more generally immiscible liquids, and is generally in the form of a colloid. The mixture may be of lipids, for example, which may be homogeneously or heterogeneously dispersed throughout the emulsion. Alternatively, the lipids may be aggregated in the form of, for example, clusters or layers, including monolayers or bilayers.

"Suspension" or "dispersion" refers to a mixture, preferably finely divided, of two or more phases (solid, liquid or gas), such as, for example, liquid in liquid, solid in solid, gas in liquid, and the like which preferably can remain stable for extended periods of time.

"Hexagonal H II phase structure" refers to a generally tubular aggregation of lipids in liquid media, for example, aqueous media, in which the hydrophilic portion(s) of the lipids generally face inwardly in association with an aqueous liquid environment inside the tube. The hydrophobic portion(s) of the lipids generally radiate outwardly and the complex assumes the shape of a hexagonal tube. A plurality of tubes is generally packed together in the hexagonal phase structure.

"Patient" refers to animals, including mammals, preferably humans.

"Region of a patient" refers to a particular area or portion of the patient and in some instances to regions throughout the entire patient. Exemplary of such regions are the gastrointestinal region, the cardiovascular region (including myocardial tissue), the renal region as well as other bodily regions, tissues, lymphocytes, receptors, organs and the like, including the vasculature and circulatory system, and as well as diseased tissue, including cancerous tissue. "Region of a patient" includes, for example, regions to be imaged with diagnostic imaging, regions to be treated with a bioactive agent, regions to be targeted for the delivery of a bioactive agent, and regions of elevated temperature. The "region of a patient" is preferably internal, although, if desired, it may be external. The phrase "vasculature" denotes blood vessels (including arteries, veins and the like). The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta.

"Region to be targeted" or "targeted region" refer to a region of a patient where delivery of a steroid prodrug and/or bioactive agent is desired. "Region to be imaged" or "imaging region" denotes a region of a patient where diagnostic imaging is desired.

"Bioactive agent" refers to a substance which may be used in connection with an application that is therapeutic or diagnostic, such as, for example, in methods for diagnosing the presence or absence of a disease in a patient and/or methods for the treatment of a disease in a patient. "Bioactive agent" also refers to substances which are capable of exerting a biological effect in vitro and/or in vivo. The bioactive agents may be neutral, positively or negatively charged. Exemplary bioactive agents include, for example, prodrugs, targeting ligands, diagnostic agents, pharmaceutical agents, drugs, synthetic organic molecules, proteins, peptides, vitamins, steroids, steroid analogs and genetic material, including nucleosides, nucleotides and polynucleotides.

"Diagnostic agent" refers to any agent which may be used in connection with methods for imaging an internal region of a patient and/or diagnosing the presence or absence of a disease in a patient. Exemplary diagnostic agents include, for example, contrast agents for use in connection with ultrasound imaging, magnetic resonance imaging or computed tomography imaging of a patient. Diagnostic agents may also include any other agents useful in facilitating diagnosis of a disease or other condition in a patient, whether or not imaging methodology is employed.

"Delivery vehicle" or "vehicle" refers to a composition, substance or material that is capable of transporting or carrying in vivo or in vitro a bioactive agent, including a steroid prodrug, a targeting ligand and/or a diagnostic agent. Exemplary delivery vehicles include, for example, stabilizing materials, vesicles, liposomes, micelles, aerogels, clathrates, gas filled vesicles, gaseous precursor filled vesicles, gas and gaseous precursor filled vesicles, gas and liquid filled vesicles, gaseous precursor and liquid filled vesicles, gas, gaseous precursor and liquid filled vesicles, emulsions, suspensions, dispersions and hexagonal H II phase structures.

"Polymer" or "polymeric" refers to molecules formed from the chemical union of two or more repeating units. Accordingly, included within the term "polymer" may be, for example, dimers, trimers and oligomers. The polymer may be synthetic, naturally-occurring or semisynthetic. In a preferred form, "polymer" refers to molecules which comprise 10 or more repeating units.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination thereof The DNA and RNA may optionally comprise unnatural nucleotides and may be single or double stranded. "Genetic material" also refers to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug.

"Detergent" refers to a surface-active agent (surfactant) which, when added to a suspending medium of colloidal particles, including, for example, certain of the lipid, polymer, protein, and/or vesicle compositions described herein, may promote uniform separation of particles. "Detergent" also refers to a surface-active agent (surfactant) which lowers the surface tension of water.

"Stabilizing material" or "stabilizing compound" refers to any material which is capable of improving the stability of compositions containing the gases, gaseous precursors, steroid prodrugs, targeting ligands and/or other bioactive agents described herein, including, for example, mixtures, suspensions, emulsions, dispersions, vesicles, or the like. Encompassed in the definition of "stabilizing material" are certain of the present bioactive agents. The improved stability involves, for example, the maintenance of a relatively balanced condition, and may be exemplified, for example, by increased resistance of the composition against destruction, decomposition, degradation, and the like. In the case of preferred embodiments involving vesicles filled with gases, gaseous precursors, liquids, steroid prodrugs and/or bioactive agents, the stabilizing compounds may serve to either form the vesicles or stabilize the vesicles, in either way serving to minimize or substantially (including completely) prevent the escape of gases, gaseous precursors, steroid prodrugs and/or bioactive agents from the vesicles until said release is desired. The term "substantially," as used in the present context of preventing escape of gases, gaseous precursors, steroid prodrugs and/or bioactive agents from the vesicles, means greater than about 50% is maintained entrapped in the vesicles until release is desired, and preferably greater than about 60%, more preferably greater than about 70%, even more preferably greater than about 80%, still even more preferably greater than about 90%, is maintained entrapped in the vesicles until release is desired. In particularly preferred embodiments, greater than about 95% of the gases, gaseous precursors, steroid prodrugs and/or bioactive agents are maintained entrapped until release is desired. The gases, gaseous precursors, liquids, steroid prodrugs and/or bioactive agents may also be completely maintained entrapped (i.e., about 100% is maintained entrapped), until release is desired. Exemplary stabilizing materials include, for example, lipids, proteins, polymers, carbohydrates and surfactants. The resulting mixture, suspension, emulsion or the like may comprise walls (i.e., films, membranes and the like) around the steroid prodrug, bioactive agent, gases and/or gaseous precursors, or may be substantially devoid of walls or membranes, if desired. The stabilizing may, if desired, form droplets. The stabilizing material may also comprise salts and/or sugars. In certain embodiments, the stabilizing materials may be substantially (including completely) cross-linked. The stabilizing material may be neutral, positively or negatively charged.

"Droplet" refers to a spherical or spheroidal entity which may be substantially liquid or which may comprise liquid and solid, solid and gas, liquid and gas, or liquid, solid and gas. Solid materials within a droplet may be, for example, particles, polymers, lipids, proteins, or surfactants.

"Cross-link," "cross-linked" and "cross-linking" generally refer to the linking of two or more stabilizing materials, including lipid, protein, polymer, carbohydrate, surfactant stabilizing materials and/or bioactive agents, by one ore more bridges. The bridges may be composed of one or more elements, groups, or compounds, and generally serve to join an atom from a first stabilizing material molecule to an atom of a second stabilizing material molecule. The cross-link bridges may involve covalent and/or non-covalent associations. Any of a variety of elements, groups, and/or compounds may form the bridges in the cross-links, and the stabilizing materials may be cross-linked naturally or through synthetic means. For example, cross-linking may occur in nature in material formulated from peptide chains which are joined by disulfide bonds of cystine residues, as in keratins, insulins and other proteins. Alternatively, cross-linking may be effected by suitable chemical modification, such as, for example, by combining a compound, such as a stabilizing material, and a chemical substance that may serve as a cross-linking agent, which may cause to react by, for example, exposure to heat, high-energy radiation, ultrasonic radiation and the like. Examples include cross-linking by sulfur to form disulfide linkages, cross-linking using organic peroxides, cross-linking of unsaturated materials by means of high-energy radiation, cross-linking with dimethylol carbamate, and the like. If desired, the stabilizing compounds and/or bioactive agents may be substantially cross-linked. The term "substantially" means that greater than about 50% of the stabilizing compounds contain cross-linking bridges. If desired, greater than about 60%, 70%, 80%, 90%, 95% or even 100% of the stabilizing compounds contain such cross-linking bridges. Alternatively, the stabilizing materials may be non-cross-linked, i.e., such that greater than about 50% of the stabilizing compounds are devoid of cross-linking bridges, and if desired, greater than about 60%, 70%, 80%, 90%, 95% or even 100% of the stabilizing compounds are devoid of cross-linking bridges.

"Vesicle stability" refers to the ability of vesicles to retain the gas, gaseous precursor and/or other bioactive agents entrapped therein after being exposed, for about one minute, to a pressure of about 100 millimeters (mm) of mercury (Hg). Vesicle stability is measured in percent (%), this being the fraction of the amount of gas which is originally entrapped in the vesicle and which is retained after release of the pressure. Vesicle stability also includes "vesicle resilience" which is the ability of a vesicle to return to its original size after release of the pressure.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, and the charge (positive or negative), if any, of the involved molecules. Non-covalent associations are selected from ionic interactions, dipole-dipole interactions, van der Waal's forces, and combinations thereof.

"Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged stabilizing material, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the uncharged, partial positive end of a first polar molecule, commonly designated as $\delta^-$, to the uncharged, partial negative end of a second polar molecule, commonly designated as $\delta^-$. Dipole-dipole interactions are exemplified by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bond" refers to an attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

"Hydrophilic interaction" refers to molecules or portions of molecules which may substantially bind with, absorb and/or dissolve in water. This may result in swelling and/or the formation of reversible gels.

"Hydrophobic interaction" refers to molecules or portions of molecules which do not substantially bind with, absorb and/or dissolve in water.

"Biocompatible" refers to materials which are generally not injurious to biological functions and which will not result in any degree of unacceptable toxicity, including allergenic responses and disease states.

"In combination with" refers to the incorporation of bioactive agents, steroid prodrugs, and/or targeting ligands, in a stabilizing composition of the present invention, including emulsions, suspensions and vesicles. The steroid prodrug, bioactive agent and/or targeting ligand can be combined with the stabilizing compositions in any of a variety of ways. For example, the steroid prodrug, bioactive agent and/or targeting ligand may be associated covalently and/or non-covalently with the compounds or stabilizing materials. In the case of vesicles, the steroid prodrug, bioactive agent and/or targeting ligand may be entrapped within the internal void of the vesicle. The steroid prodrug, bioactive agent and/or targeting ligand may also be integrated within the layer(s) or wall(s) of the vesicle, for example, by being interspersed among stabilizing materials which form or are contained within the vesicle layer(s) or wall(s). In addition, it is contemplated that the steroid prodrug, bioactive agent and/or targeting ligand may be located on the surface of a vesicle or non-vesicular stabilizing material. The steroid prodrug, bioactive agent and/or targeting ligand may be concurrently entrapped within the internal void of the vesicle and/or integrated within the layer(s) or wall(s) of the vesicles and/or located on the surface of a vesicle or non-vesicular stabilizing material. In any case, the steroid prodrug, bioactive agent and/or targeting ligand may interact chemically with the walls of the vesicles, including, for example, the inner and/or outer surfaces of the vesicle and may remain substantially adhered thereto. Such interaction may take the form of, for example, non-covalent association or bonding, ionic interactions, electrostatic interactions, dipole-dipole interactions, hydrogen bonding, van der Waal's forces, covalent association or bonding, cross-linking or any other interaction, as will be readily apparent to one skilled in the art, in view of the present disclosure. In certain embodiments, the interaction may result in the stabilization of the vesicle. The bioactive agent may also interact with the inner or outer surface of the vesicle or the non-vesicular stabilizing material in a limited manner. Such limited interaction would permit migration of the bioactive agent, for example, from the surface of a first vesicle to the surface of a second vesicle, or from the surface of a first non-vesicular stabilizing material to a second non-vesicular stabilizing material. Alternatively, such limited interaction may permit migration of the bioactive agent, for example, from within the walls of a vesicle and/or non-vesicular stabilizing material to the surface of a vesicle and/or non-vesicular stabilizing material, and vice versa, or from inside a vesicle or non-vesicular stabilizing material to within the walls of a vesicle or non-vesicular stabilizing material and vice versa.

"Targeting ligand" refers to any material or substance which may promote targeting of tissues and/or receptors in vivo or in vitro with the compositions of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, bioactive agents, and genetic material, including nucleosides, nucleotides, nucleotide acid constructs and polynucleotides.

A "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and $\alpha$-iodo acetyl groups.

"Protein" refers to molecules comprising, and preferably consisting essentially of, $\alpha$-amino acids in peptide linkages. Included within the term "protein" are globular proteins such as albumins, globulins and histones, and fibrous proteins such as collagens, elastins and keratins. Also included within the term "protein" are "compound proteins," wherein a protein molecule is united with a nonprotein molecule, such as nucleoproteins, mucoproteins, lipoproteins and metalloproteins. The proteins may be naturally-occurring, synthetic or semi-synthetic.

"Tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells. Exemplary tissues include myocardial tissue, including myocardial cells and cardiomyocites, membranous tissues, including endothelium and epithelium, laminae, connective tissue, including interstitial tissue, and tumors.

"Receptor" refers to a molecular structure within a cell or on the surface of a cell which is generally characterized by the selective binding of a specific substance. Exemplary receptors include cell-surface receptors for peptide hormones, neurotransmitters, antigens, complement fragments, immunoglobulins and cytoplasmic receptors for steroid hormones.

"Intracellular" or "intracellularly" refers to the area within the plasma membrane of a cell, including the protoplasm, cytoplasm and/or nucleoplasm. "Intracellular delivery" refers to the delivery of a bioactive agent, such as a targeting ligand and/or steroid prodrug, into the area within the plasma membrane of a cell.

"Cell" refers to any one of the minute protoplasmic masses which make up organized tissue, comprising a mass of protoplasm surrounded by a membrane, including nucleated and unnucleated cells and organelles.

"Alkyl" refers to linear, branched or cyclic hydrocarbon groups. Preferably, the alkyl is a linear or branched hydrocarbon group, more preferably a linear hydrocarbon group. Exemplary linear and branched alkyl groups include, for example, methyl, ethyl, n-propyl, i-propyl, n-butyl, t-butyl, n-pentyl, hexyl, heptyl, octyl, nonyl, and decyl groups. Exemplary cyclic hydrocarbon groups (cycloalkyl groups) include, for example, cyclopentyl, cyclohexyl and cycloheptyl groups. "Fluoroalkyl" refers to an alkyl group which is substituted with one or more fluorine atoms, including, for example, fluoroalkyl groups of the formula $CF_3(CF_2)_n(CH_2)_m$—, wherein each of m and n is independently an integer from 0 to about 22. Exemplary fluoroalkyl groups include perfluoromethyl, perfluoroethyl, perfluoropropyl, perfluorobutyl, perfluorocyclobutyl, perfluoropentyl, perfluorohexyl, perfluoroheptyl, perfluorooctyl, perfluorononyl, perfluorodecyl, perfluoroundecyl and perfluorododecyl.

"Acyl" refers to an alkyl-CO— group wherein alkyl is as previously described. Preferred acyl groups comprise alkyl of 1 to about 30 carbon atoms. Exemplary acyl groups include acetyl, propanoyl, 2-methylpropanoyl, butanoyl and palmitoyl. "Fluoroacyl" refers to an acyl group that is substituted with one or more fluorine atoms, up to and including perfluorinated acyl groups.

"Aryl" refers to an aromatic carbocyclic radical containing about 6 to about 10 carbon atoms. The aryl group may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Alkylaryl" refers to alkyl-aryl- groups (e.g., $CH_3$—$(C_6H_4)$—) and aryl-alkyl-groups (e.g., $(C_6H_5)$—$CH_2$—) where aryl and alkyl are as previously described. Exemplary alkylaryl groups include benzyl, phenylethyl and naphthylmethyl. "Fluoroalkylaryl" refers to an alkylaryl group that is substituted with one or more fluorine atoms, up to and including perfluorinated alkylaryl groups.

"Alkylene" refers to a straight or branched bivalent aliphatic hydrocarbon group having from 1 to about 30 carbon atoms. The alkylene group may be straight, branched or cyclic. The alkylene group may be also optionally unsaturated and/or substituted with one or more "alkyl group substituents," including halogen atoms, such as fluorine atoms. There may be optionally inserted along the alkylene group one or more oxygen, sulphur or substituted or unsubstituted nitrogen atoms, wherein the nitrogen substituent is alkyl as previously described. Exemplary alkylene groups include methylene (—$CH_2$—), ethylene (—$CH_2CH_2$—), propylene (—$(CH_2)_3$—), cyclohexylene (—$C_6H_{10}$—), —CH=CH—CH=CH—, —CH=CH—$CH_2$—, —$(CF_2)_n(CH_2)_m$—, wherein n is an integer from about 1 to about 22 and m is an integer from 0 to about 22, —$(CH_2)_n$—N(R)—$(CH_2)_m$—, wherein each of m and n is independently an integer from 0 to about 30 and R is hydrogen or alkyl, methylenedioxy (—O—$CH_2$—O—) and ethylenedioxy (—O—$(CH_2)_2$—O—). It is preferred that the alkylene group has about 2 to about 3 carbon atoms.

"Halo," "halide" or "halogen" refers to chlorine, fluorine, bromine or iodine atoms.

Steroid Prodrugs

The present invention is directed to derivatives of steroidal compounds. In one embodiment, the steroid derivatives improve the lipophilicity of the steroids and provide chemical compatibility with lipid compositions and other drug delivery vehicles. To facilitate the stable insertion of the steroid derivatives into stabilizing materials, lipid moieties capable of fusion or intercalation with the stabilizing compounds are covalently bound to the steroids via a linking group. The bond between the attached lipid moieties and the parent steroid may be sufficiently labile to be hydrolyzed by native enzymes within the targeted cell or tissue or, alternatively, may be hydrolyzed by ultrasound or other applications of external energy. In other embodiments, the steroid prodrug may retain its bioactive properties without further chemical modification, but the lipid moiety and other targeting facilitators will enhance the efficiency of intracellular delivery.

The novel lipid soluble steroid prodrugs may be used for site specific delivery and targeting to tissues and receptors to improve efficacy and decrease toxicity. The lipid soluble steroid prodrugs may be used where membrane traversal or fusion facilitates delivery. In the case of topical applications of anti-inflammatories, the water insolubility of the novel lipid soluble steroid prodrugs promotes skin penetration and the lifetime of the medicament at the targeted site.

As one skilled in the art would recognize, a chemical group that is used to modify a particular steroid may be selected to influence the partitioning of the steroid onto the surface of the stabilizing materials, within the walls or layers of the stabilizing materials, within the internal space of the stabilizing materials and/or any combination thereof. The bond linking the chemical group to the steroid may be selected to have the desired rate of metabolism, e.g., hydrolysis in the case of ester bonds in the presence of serum esterases, after release from the stabilizing compositions and/or vesicles. Additionally, a chemical group may be selected to influence the biodistribution of the drug employed in the stabilizing material. The steroid prodrugs of the present invention may be encapsulated within the stabilizing materials and may contain reversible derivatives which modify the duration of activity to provide, prolong or depot action effects of the steroid in vivo or in vitro, as would be readily apparent to one skilled in the art in view of the present disclosure.

The present invention is directed, in part, to compounds comprising a steroid covalently bonded to a lipid moiety via a linking group. In one embodiment of the invention, the compound may be of the formula (I):

$$D—X—L \qquad (I)$$

wherein:

D is a steroid;

X is a linking group comprising an ester group, a carbamate group, a carbonyl group, a thioester group, a disulfide group, an ether group, an anhydride group, or an amide group; and L is a lipid moiety comprising an acyl, alkyl, alkylaryl, fluoracyl, fluoroalkyl or fluoroalkylaryl group having from about 4 to about 40 carbon atoms.

Preferably, D is a steroid which may be a compound of the formula (III) or any of the steroids described herein. Most preferably, D is dexamethasone.

Preferably, X is a linking group that is sufficiently stable for storage but which is also biodegradable, such as, for example, an ester group. Most preferably, X is succinate.

Preferably, L is a lipid moiety comprising an acyl, alkyl, alkylaryl, fluoroacyl, fluoroalkyl or fluoroalkylaryl moiety having from about 4 to about 40 carbon atoms and more preferably from about 6 to about 40 carbon atoms. The acyl or alkyl group may consist of one, two or three chains or an alkylaryl group. In a preferred embodiment, L may be a diacylated moiety in which two acyl chains are linked to glycerol. More preferably, L may be dipalmitoylglyceryl, dimyristoylglyceryl, distearoylglyceryl, or dioleoylglyceryl. Alternatively, L may be cholesterol. Thus, X—L is preferably dipalmitoylglycerylsuccinate, dimyristoylglycerylsuccinate, distearoylglycerylsuccinate, dioleoylglycerylsuccinate or cholesterol succinate.

In another embodiment, L may be a lipid moiety comprising a fluoroacyl, fluoroalkyl or fluoroalkylaryl group. The acyl, alkyl or alkylaryl group may comprise one or more fluorine atoms, preferably from about 3 to about 23 fluorine atoms, more preferably from about 5 to about 18 fluorine atoms. When the acyl, alkyl or alkylaryl group is part of a linear chain, the terminal carbon atoms are preferably fluorinated. Alternatively, the acyl, alkyl or alkylaryl group may be a perfluorinated group. Perfluorinated means that all the hydrogen atoms, except those whose replacement would affect the nature of the characteristic groups present, are replaced by fluorine atoms. For example, bipyridine moieties may be perfluoroalkylated as described in Garelli and Vierling, *Biochim. Biophys. Acta* (1992) 1127:41–48, the disclosure of which is hereby incorporated by reference herein in its entirety. Other fluorinated amphiphilic molecules which serve in this capacity are fluorosurfactants and the compounds disclosed in U.S. Pat. No. 5,562,893 and U.S. application Ser. No. 08/465,868, filed Jun. 6, 1995, the disclosures of which are hereby incorporated herein by reference in their entirety.

The present invention may also be directed to a compound of the formula (II), which is encompassed within the scope of the compound of the formula (I):
wherein:

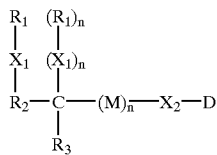
(II)

each $X_1$ is independently a direct bond, —O—, —S—, —SO—, —SO$_2$—, —NR$_4$—, —X$_3$—C(=X$_4$)—, —C(=X$_4$)—X$_3$— or —C(=X$_4$)—;

each n is independently an integer of 0 or 1;

$X_2$ is a direct bond, —C(=X$_4$)—, —R$_5$—X$_3$—C(=X$_4$)—, —R$_5$—C(=X$_4$)—X$_3$, —X$_3$—C(=X$_4$)—R$_5$—, —C(=X$_4$)—X$_3$—R$_5$—, —X$_3$—R$_5$—C(=X$_4$)—X$_3$—, C(=X$_4$)—R$_5$—C(=X$_4$)—, —R$_5$—X$_3$C(=X$_4$)—R$_5$—C(=X$_4$)—X$_3$—, —C(=X$_4$)R$_5$—C(=X$_4$)—X$_3$— or —R$_5$—C(=X$_4$)—X$_3$—(YX$_4$)P(=X$_4$)—;

each $X_3$ is independently —O—, —NR$_4$— or —S—;

each $X_4$ is independently O or S;

M is —R$_5$—X$_3$—, —R$_5$—X$_3$—C(=X$_4$)—, —R$_5$—C(=X$_4$)—X$_3$—, —R$_5$—X$_3$—(YX$_4$)P(=X$_4$)—X$_3$— or —X$_3$—(YX$_4$)P(=X$_4$)—X$_3$—R$_5$—;

Y is hydrogen or a pharmaceutically acceptable counter ion;

D is a steroid;

each $R_1$ is independently an alkyl group of 1 to about 50 carbon atoms that is optionally substituted with one or more halogen atoms;

each $R_2$ is independently an alkylene group of 1 to about 30 carbon atoms that is optionally substituted with one or more halogen atoms;

each of $R_3$ and $R_4$ is independently =O, a hydrogen atom or an alkyl group of 1 to about 10 carbon atoms; and each $R_5$ is independently a direct bond or an alkylene group of 1 to about 30 carbon atoms.

In the above formula, it is intended that when any symbol appears more than once in a particular formula or substituent, its meaning in each instance is independent of the other. Also, it is intended that when each of two or more adjacent symbols is defined as being a "direct bond" to provide multiple, adjacent direct bonds, the multiple and adjacent direct bonds devolve into a single direct bond.

In preferred embodiments of formula (II), each $X_1$ is independently —X$_3$—C(=X$_4$)—, —C(=X$_4$)—X$_3$— or —C(=X$_4$)—. More preferably, each $X_1$ is independently —X$_3$—C(=X$_4$)— or —C(=X$_4$)—X$_3$—. Even more preferably, $X_1$ is —C(=X$_4$)—X$_3$—, for example, —C(=O)—O—.

In preferred embodiments of formula (II), $X_2$ is a direct bond, —C(=X$_4$)—, —C(=X$_4$)—R$_5$—C(=X$_4$)—, —C(=X$_4$)—R$_5$—C(=X$_4$)—X$_3$—, —R$_5$—X$_3$—C(=X$_4$)—, —R$_5$—C(=X$_4$)—X$_3$—, —X$_3$—C(=X$_4$)—R$_5$—, —C(=X$_4$)—X$_3$—R$_5$—, —X$_3$—R$_5$—C(=X$_4$)—X$_3$— or —R$_5$—X$_3$—C(=X$_4$)—X$_3$—. More preferably, $X_2$ is a direct bond, —C(=O)—CH$_2$CH$_2$—C(=O)—, —CH$_2$CH$_2$—C(=O)—NH—, or —CH$_2$CH$_2$NH—C(=O)—CH$_2$CH$_2$—C(=O)—NH—; most preferably —C(=O)—CH$_2$CH$_2$—C(=O)—.

In preferred embodiments, each $X_3$ is independently —O— or —NR$_4$—, most preferably —O—.

Preferably, $X_4$ is O.

In certain preferred embodiments, M is —R$_5$—X$_3$—(YX$_4$)P(=X$_4$)—X$_3$—, —R$_5$—X$_3$— or —R$_5$—X$_3$—C(=X$_4$)—, with M more preferably being —CH$_2$O—(HO)P(=O)—O—, —CH$_2$O—C(=O)— or —CH$_2$—O—. In certain other preferred embodiments, M is —R$_5$—X$_3$—C(=X$_4$)— or —R$_5$—C(=X$_4$)—X$_3$—.

In yet other preferred embodiments, M is —R$_5$—X$_3$—(YX$_4$)P(=X$_4$)—X$_3$— or —X$_3$—(YX$_4$)P(=X$_4$)—X$_3$—R$_5$— wherein at least one of $X_3$ or $X_4$ is S.

In the above formula, D is a steroid. Preferably, the steroid may be a compound of the formula (III) or any of the steroids described herein. Most preferably, the steroid is dexamethasone.

In the above formula, each $R_1$ is independently an alkyl group which ranges from 1 to about 50 carbon atoms, and all combinations and subcombinations of ranges therein, or an alkenyl group of from about 2 to about 50 carbon atoms, and all combinations and subcombinations of ranges therein. Optionally, the alkyl group and/or alkenyl group can comprise one or more halogen atoms, including perhalogenated alkyl groups and/or alkenyl groups. The halogen atom may be chlorine, fluorine, bromine or iodine, with fluorine being preferred. Preferably, each $R_1$ is independently an alkyl group of greater than 1 to about 40 carbon atoms. More preferably, each R1 is independently an alkyl group of about 5 to about 30 carbon atoms. Even more preferably, each $R_1$ is independently an alkyl group of about 10 to about 20 carbon atoms, with an alkyl group of about 13 to about 17 carbon atoms being more preferred, and with about 15 carbons being still more preferred. In certain preferred embodiments, $R_1$ is a shorter chain alkyl group of from 1 to about 20 carbon atoms. In certain other preferred embodiments, $R_1$ is a longer chain alkyl group of from about 20 to about 50 carbon atoms, or about 30 to about 50 carbon atoms.

In the above formula, each $R_2$ is independently an alkylene group which ranges from 1 to about 30 carbon atoms, and all combinations and subcombinations of ranges therein. Optionally, the alkylene group can comprise one or more halogen atoms, including perhalogenated alkylene groups. The halogen atom may be chlorine, fluorine, bromine or iodine, with fluorine being preferred. Preferably, each $R_2$ is independently an alkylene group of 1 to about 20 carbon atoms. More preferably, each $R_2$ is independently an alkylene group of 1 to about 10 carbon atoms. Even more preferably, each $R_2$ is independently an alkylene group of 1 to about 5 carbon atoms, more preferably about 1 or about 2 carbon atoms, with 2 carbon atoms being most preferred.

In the above formula, each of $R_3$ and $R_4$ is independently =O, a hydrogen atom or an alkyl group which ranges from 1 to about 10 carbon atoms, and all combinations and subcombinations of ranges therein. Preferably, each of $R_3$ and $R_4$ is =O, a hydrogen atom or alkyl of 1 to about 5 carbon atoms. More preferably, each of $R_3$ and $R_4$ is a hydrogen atom.

In the above formula, each $R_5$ is independently a direct bond or an alkylene group which ranges from 1 to about 30 carbon atoms, and all combinations and subcombinations of ranges therein. Preferably, each $R_5$ is independently a direct bond or an alkylene group of 1 to about 20 carbon atoms. More preferably, each $R_5$ is independently a direct bond or an alkylene group of 1 to about 10 carbon atoms. Even more preferably, each $R_5$ is independently a direct bond or an alkylene group of 1 to about 5 carbon atoms. Still more preferably, each $R_5$ is a direct bond or $-(CH_2)_x-$, where $x$ is 1 or 2.

In other preferred embodiments for the compound of formula (II), $X_1$ is a direct bond; $X_2$ is a direct bond; n is 0; $R_3$ is =O; $R_2$ is an unsubstituted alkylene group having from 1 to about 20 carbon atoms, preferably from about 1 to about 12 carbon atoms, more preferably from about 2 to about 6 carbon atoms, even more preferably about 4 carbon atoms (e.g., $-(CH_2)_4-$); $R_1$ is a substituted alkyl group having from about 1 to about 30 carbon atoms; more preferably a fluorine substituted alkyl group having from about 1 to about 20 carbon atoms; more preferably a fluorine substituted alkyl group having from about 2 to about 18 carbon atoms; even more preferably a perfluorinated alkyl group having from about 4 to about 15 carbon atoms; still more preferably a perfluorinated alkyl group having from about 6 to about 12 carbon atoms; most preferably a perfluorinated alkyl group having about 9 carbon atoms (e.g., $-(CF_2)_8-CF_3$).

As discussed above, the steroid in the present invention, and D in the compound of the formula (I) and formula (II) may be any steroid, steroid hormone, steroid analog, sterol or compound having affinity to steroid or steroid-like receptors. In a preferred embodiment, the steroid of the present invention, represented by D in formula (I) and (II) above, may be of the formula (III):

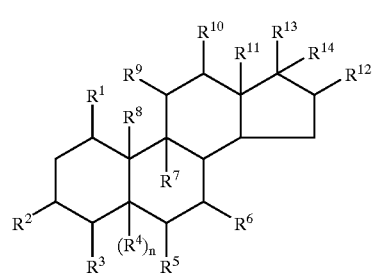

(III)

wherein:
$R^1$ is a saturated or unsaturated double bond;
$R^2$ is R', =O, OR', R'—N—(R')$_2$, SR', C(=O)R', C(=O)OR', C(=S)OR', C(=O)SR', OC(=O)R', OOC(C$_6$H$_5$);
R' is a hydrogen atom or a $C_1$ to $C_{60}$ saturated or unsaturated linear or branched hydrocarbon chain, optionally interrupted with O, S, P or N, and optionally substituted with halogen atoms;
$R^3$ is a saturated or unsaturated double bond;
$R^4$ is a halogen atom or R';
n is an integer of 0 or 1;
$R^5$ is R' or a halogen atom;
$R^6$ is R' or an unsaturated double bond;
$R^7$ is R' or a halogen atom;
$R^8$ is R' or an unsaturated double bond;
$R^9$ is =O, OH, R' or a halogen atom;
$R^{10}$ is R', a halogen atom or OH;
$R^{11}$ is R' or C(=O)H;
$R^{12}$ is R', OH, OCOR' or =CH$_2$;
$R^{13}$ is R', =O, OH, OC(=O)R', C(=O)CH$_2$OR', C(=O)CH$_3$; C(=O)OR', CCH, or an alkyl halide group; and
$R^{14}$ is R', OH, CCH, CCCH3, or OC(=O)R'.

The steroid may have an or β stereochemistry. The halogen atoms in the compound of the formula (III) may be chlorine, bromine, fluorine or iodine; preferably fluorine or chlorine. R' is preferably a hydrogen atom, a methyl group, an ethyl group, a propyl group, a butyl group, a pentyl group, a hexyl group, $-COCH_2OC(=O)C(CH_3)$, $-C(=O)CH_2CH_2CO_2$ or $-COCH_3$; more preferably R' is a hydrogen atom or a methyl group.

In addition to the steroids of formula (III) above, other steroids, known to those skilled in the art, may be used in the present invention. Exemplary steroids that may be used in the present invention include, for example, dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fludrocortisone, fludrocortisone acetate, dichlorisone acetate, fluorohydrocortisone, fluoromethorone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel. Most preferably, the steroid is dexamethasone.

Additionally, steroids that are useful in the present invention include steroid hormones, sterols, steroid analogs or compounds with particular affinity to steroid or steroid-like receptors, such as diethylstilbestrol and analogs thereof; metyrapone and analogs thereof, and steroid analogs that maintain eutrogenic, androgenic, glucocorticoid, adrenocortoid, anabolic or birth control activity.

Preferably the steroid is particularly active, such that a low dose is required for a therapeutic effect. The amount of steroid to be administered depends on the particular steroid that is being administered, the method of administration of the steroid, and the age, sex, weight and physical condition of the patient. Generally, treatment is initiated with small dosages, which can then be increased by small increments until the optimum effect under the circumstances is reached. For example, the amount of steroid to be administered may variable range from about 0.1 mg to about 50 mg, preferably about 0.1 mg to about 25 mg, more preferably about 0.5 mg to about 5 mg.

Methods for synthesizing steroids are well-known to the skilled artisan and are set forth, for example, in *Organic Chemistry of Drug Synthesis*, Volume 1, Chapter 10 "Steroids" by Ledincer and Mitscher, the disclosure of which is hereby incorporated herein by reference in its entirety. The steroids of the present invention are also available from a wide variety of commercial suppliers, including, for example, Sigma Chemical Company, St. Louis, Mo.

In view of the present disclosure, and with knowledge of synthetic organic chemistry, one skilled in the art would readily recognize the locations on any particular steroid, linking group and lipid moiety where attachments may be made to covalently attach the steroid to the linking group and the linking group to the lipid moiety. For example, —OH, —COOH, —NH or —SH groups which are present on a steroid, a linking group or a lipid moiety are obvious points at which the steroid, linking group and lipid moiety may be attached to each other. Steroids generally have —OH, —COOH, —NH or —SH terminal groups at one or more locations, any of which may serve as the point of attachment to the linking group. If the steroid, linking group or lipid moiety does not have a —OH, —COOH, —NH or —SH terminal group, basic synthetic addition chemistry, which is well known to those skilled in the art, can be utilized to introduce an —OH group into the molecule, which would then be suitable as a point of attachment.

The novel lipid soluble steroid prodrugs of the present invention may be administered to a patient without a delivery vehicle. Preferably the steroid prodrugs are administered in combination with a delivery vehicle, such as stabilizing materials, which accomplishes several things for the steroid prodrugs. For example, the delivery vehicle may help to solubilize or stabilize the steroid prodrugs, since the steroid prodrugs are generally less soluble in an aqueous media than the parent compounds. The stabilizing materials may be lipids, proteins, polymers, carbohydrates and/or surfactants, preferably lipids or surfactants, more preferably lipids.

As can be seen from the compounds of formula (I) and formula (II) above, the steroid may be derivatized with a hydrophobic group, which increases the lipophilicity of the steroid and may increase its octanol/water partition coefficient. The steroid prodrugs are readily incorporated into stabilizing materials, emulsions, suspensions, dispersions, vesicles, liposomes, micelles, and lipid and oil emulsions. In a preferred embodiment, the steroid prodrugs are incorporated into the stabilizing materials surrounding gas bubbles, gaseous precursors, foams and foam precursors.

Delivery Vehicles

A wide variety of lipids may be used as stabilizing materials and vesicles, for example, micelles and/or liposomes, and any of the materials or combinations thereof which are known to those skilled in the art are suitable for their preparation. The lipids may be of either natural, synthetic or semi-synthetic origin, including for example, fatty acids, neutral fats, phosphatides, oils, glycolipids, surface-active agents (surfactants), aliphatic alcohols, waxes, terpenes and steroids.

Exemplary lipids which may be used to prepare the stabilizing materials of the present invention include, for example, fatty acids, lysolipids, fluorolipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine; dipentadecanoyl-phosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoyl-phosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoyl-phosphatidic acid (DSPA); palmitic acid; stearic acid; arachidonic acid; oleic acid; lipids bearing polymers, such as chitin, hyaluronic acid, polyvinyl-pyrrolidone or polyethylene glycol (PEG), also referred to herein as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides;

cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene sorbitan fatty acid esters (such as, for example, the class of compounds referred to as TWEEN™, including TWEEN 20, TWEEN 40 and TWEEN 80, commercially available from ICI Americas, Inc., Wilmington, Del.), including polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)-hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylamino-coumarin-3-yl)-carbonyl)-methylamino)-octadecanoic acid; N-[12-(((7'-diethylamino-coumarin-3-yl)-carbonyl)-methylamino)-octadecanoyl]-2-aminopalmitic acid; cholesteryl(4'-trimethyl-ammonio)-butanoate; N-succinyldioleoylphosphatidylethanol-amine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycero-phosphoethanolamine and palmitoylhomocysteine, and/or any combinations thereof.

Examples of polymerized lipids include unsaturated lipophilic chains such as alkenyl or alkynyl, containing up to about 50 carbon atoms. Further examples are phospholipids such as phosphoglycerides and sphingolipids carrying polymerizable groups, and saturated and unsaturated fatty acid derivatives with hydroxyl groups, such as for example triglycerides of d-12-hydroxyoleic acid, including castor oil and ergot oil. Polymerization may be designed to include hydrophilic substituents such as carboxyl or hydroxyl groups, to enhance dispersability so that the backbone residue resulting from biodegradation is water soluble. Exemplary polymerizable lipid compounds which may be utilized in the compositions of the present invention are illustrated below.

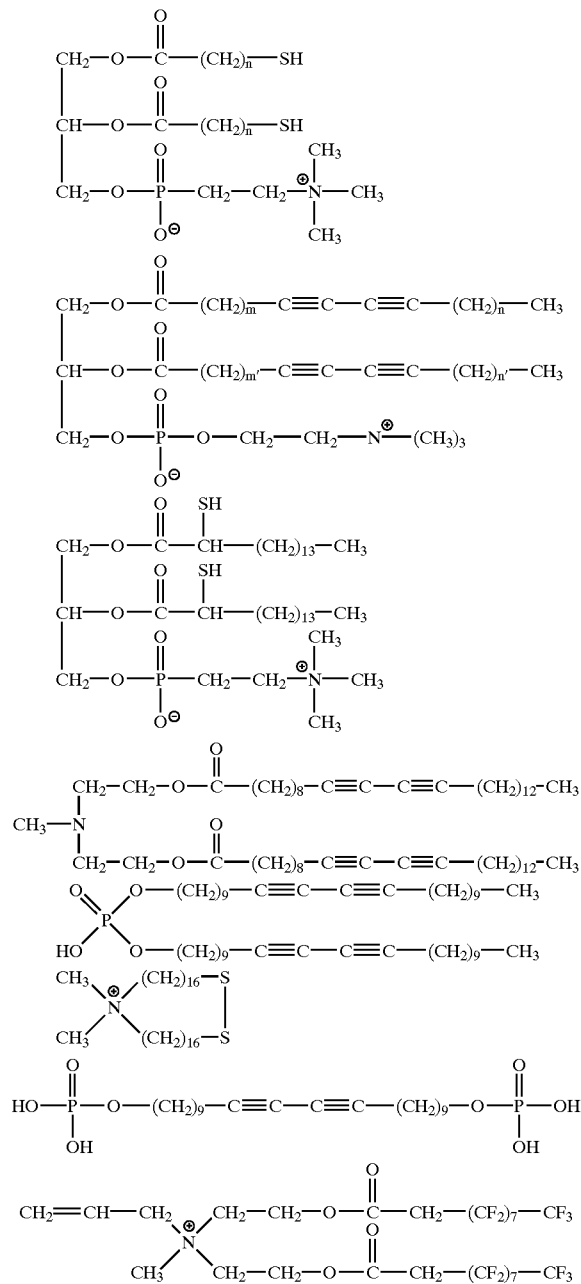

Suitable polymerizable lipids are also described, for example, in Klaveness et al, U.S. Pat. No. 5,536,490, the disclosure of which is hereby incorporated by reference herein in its entirety.

In preferred embodiments, the stabilizing materials comprise phospholipids, including one or more of DPPC, DPPE, DPPA, DSPC, DSPE, DSPG, and DAPC (20 carbon atoms).

If desired, the stabilizing material may comprise a cationic lipid, such as, for example, N-[1-(2,3-dioleoyloxy) propyl]-N,N,N-trimethylammonium chloride (DOTMA), 1,2-dioleoyloxy-3-(trimethylammonio)propane (DOTAP); and 1,2-dioleoyl-3-(4'-trimethylammonio)-butanoyl-sn-glycerol (DOTB). If a cationic lipid is employed in the stabilizing materials, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

If desired, aggregates may be constructed of one or more charged lipids in association with one or more polymer bearing lipids, optionally in association with one or more neutral lipids. The charged lipids may either be anionic or cationic. Typically, the lipids are aggregated in the presence of a multivalent species, such as a counter ion, opposite in charge to the charged lipid. For delivery of prodrugs and/or bioactive agents to selective sites in vivo, aggregates of preferably under 2 microns, more preferably under 0.5 microns, and even more preferably under 200 nm are desired. Most preferably the lipid aggregates are under 200 nm in size and may be as small as 5–10 nm in size.

Exemplary anionic lipids include phosphatidic acid and phosphatidyl glycerol and fatty acid esters thereof, amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, sulfolipids, and sulfatides, free fatty acids, both saturated and unsaturated, and negatively charged derivatives thereof. Phosphatidic acid and phosphatidyl glycerol and fatty acid esters thereof are preferred anionic lipids.

When the charged lipid is anionic, a multivalent (divalent, trivalent, etc.) cationic material may be used to form aggregates. Useful cations include, for example, cations derived from alkaline earth metals, such as beryllium ($Be^{+2}$), magnesium ($Mg^{+2}$), calcium ($Ca^{+2}$), strontium ($Sr^{+2}$), and barium ($Ba^{+2}$); amphoteric ions such as aluminum ($Al^{+3}$), gallium ($Ga^{+3}$), germanium ($Ge^{+3}$), tin ($Sn^{+4}$), and lead ($Pb^{+2}$ and $Pb^{+4}$); transition metals such as titanium ($Ti^{+3}$ and $Ti^{+4}$), vanadium ($V+2$ and $V^{+3}$), chromium ($Cr^{+2}$ and $Cr^{+3}$), manganese ($Mr^{+2}$ and $Mn^{+3}$), iron ($Fe^{+2}$ and $Fe^{+3}$), cobalt ($Co^{+2}$ and $Co^{+3}$), nickel ($Ni^{+2}$ and $Ni^{+3}$), copper ($Cu^{+2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W^{+4}$), osmium ($Os^{+2}$, $Os^{+3}$ and $Os^{+4}$), iridium $W^{+2}$, $Ir^{+3}$ and $Ir^{+4}$), mercury ($Hg^{+2}$), and bismuth ($Bi^{+3}$); and rare earth lanthanides, such as lanthanum ($La^{+3}$), and gadolinium ($Gd^{+3}$). It is contemplated that cations in all of their ordinary valence states will be suitable for forming aggregates and cross-linked lipids. Preferred cations include calcium ($Ca^{+2}$), magnesium ($Mg^{+2}$), and zinc ($Zn^{+2}$) and paramagnetic cations such as manganese (preferably $Mn^{+2}$) and gadolinium ($Gd^{+3}$). Particularly preferred is calcium ($Ca^{+2}$). As will be apparent to one skilled in the art, some of the above ions (notably lead and nickel) may have associated toxicity and thus may be inappropriate for in vivo use.

When the charged lipid is cationic, an anionic material, for example, may be used to form aggregates. Preferably, the anionic material is multivalent, such as, for example, divalent. Examples of useful anionic materials include monatomic and polyatomic anions such as carboxylate ions, sulfide ion, sulfite ions, sulfate ions, oxide ions, nitride ions, carbonate ions, and phosphate ions. Anions of ethylene diamine tetraacetic acid (EDTA), diethylene triamine pentaacetic acid (DTPA), and 1,4,7, 10-tetraazocyclododecane-N',N',N",N"-tetraacetic acid (DOTA) may also be used. Further examples of useful anionic materials include anions of polymers and copolymers of acrylic acid, methacrylic acid, other polyacrylates and methacrylates, polymers with pendant $SO_3H$ groups, such as sulfonated polystyrene, and polystyrenes containing carboxylic acid groups.

Examples of cationic lipids include those listed hereinabove. A preferred cationic lipid for formation of aggregates is N-[1-(2,3-dioleoyloxy)propyl]-N,N,N-trimethylammonium chloride ("DOTMA"). Synthetic cationic lipids may also be used. These include common natural lipids derivatized to contain one or more basic functional groups. Examples of lipids which can be so modified include dimethyldioctadecyl-ammonium bromide, sphinolipids, sphingomyelin, lysolipids, glycolipids such as ganglioside GM1, sulfatides, glycosphingolipids, cholesterol and cholesterol esters and salts, N-succinyldioleoylphosphatidylethanolamine, 1,2, -dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoylhomocystiene.

Specially synthesized cationic lipids also function in the embodiments of the invention. Among these are those disclosed in pending U.S. patent application Ser. No. 08/391, 938, filed Feb. 21, 1995, the disclosure of which is hereby incorporated herein by reference in its entirety, and include, for example, N,N'-bis (dodecyaminocarbonyl-methylene)-N,N'-bis (β-N,N,N-trimethylammoniumethylaminocarbonylmethylene-ethylene-diamine tetraiodide; N,N"-bis hexadecylaminocarbonylmethylene)-N,N',N"-tris hexaiodide; N,N'-Bis(dodecylaminocarbonylmethylene)-N,N"-bis (β-N,N,N-trimethyl-ammoniumethylaminocarbonylmethylene)cyclohexylene-1, 4-diamine tetraiodide; 1,1,7,7-tetra-(β-N,N,N,N-tetramethylammoniumethylaminocarbonylmethylene)-3-hexadecyl-aminocarbonylmethylene-1,3,7-triaazaheptane heptaiodide; and N,N,N'N'-tetraphospho-ethanolaminocarbonylmethylene)diethylenetriamine tetraiodide.

In the case of stabilizing materials which contain both cationic and non-cationic lipids, a wide variety of lipids, as described above, may be employed as the non-cationic lipid. Preferably, the non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates, and alkyl phosphites, may also be used in the stabilizing materials. Those of skill in the art will recognize, in view of the present disclosure, that other natural and synthetic variants carrying positive charged moieties will also function in the invention.

Saturated and unsaturated fatty acids which may be employed in the present stabilizing materials include molecules that preferably contain from about 12 carbon atoms to about 22 carbon atoms, in linear or branched form. Hydrocarbon groups consisting of isoprenoid units and/or prenyl groups can be used. Examples of suitable saturated fatty acids include, for example, lauric, myristic, palmitic, and stearic acids. Examples of suitable unsaturated fatty acids include, for example, lauroleic, physeteric, myristoleic, palmitoleic, petroselinic, and oleic acids. Examples of suitable branched fatty acids include, for example, isolauric, isomyristic, isopalmitic, and isostearic acids.

Other useful lipids or combinations thereof apparent to those skilled in the art which are in keeping with the spirit of the present invention are also encompassed by the present invention. For example, carbohydrate-bearing lipids may be employed, as described in U.S. Pat. No. 4,310,505, the disclosure of which is hereby incorporated herein by reference in its entirety.

In addition to stabilizing materials and/or vesicles formulated from lipids, embodiments of the present invention may involve vesicles formulated, in whole or in part, from proteins or derivatives thereof. Suitable proteins for use in the present invention include, for example, albumin, hemoglobin, α-1-antitrypsin, α-fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, α-1-serum protein fraction, α-2-serum protein fraction, β-protein fraction, γ-protein fraction and γ-glutamyl transferase. Other stabilizing materials and vesicles formulated from proteins that may be used in the present invention are described, for example, in U.S. Pat. Nos. 4,572,203, 4,718,433, 4,774,958, and 4,957,656, the disclosures of which are hereby incorporated herein by reference in their entirety. Other protein-based stabilizing materials and vesicles, in addition to those described above and in the aforementioned patents, would be apparent to one of ordinary skill in the art, in view of the present disclosure.

In addition to stabilizing materials and/or vesicles formulated from lipids and/or proteins, embodiments of the present invention may also involve stabilizing materials or vesicles formulated from polymers which may be of natural, semi-synthetic (modified natural) or synthetic origin. Polymer denotes a compound comprised of two or more repeating monomeric units, and preferably 10 or more repeating monomeric units. Semi-synthetic polymer (or modified natural polymer) denotes a natural polymer that has been chemically modified in some fashion. Examples of suitable natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dennatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethyl-cellulose, hydroxypropylmethylcellulose, methylcellulose, and methoxycellulose. Exemplary synthetic polymers suitable for use in the present invention include polyphosphazenes, polyethylenes (such as, for example, polyethylene glycol (including, for example, the class of compounds referred to as PLURONICS®, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Preferred are biocompatible synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkyl-acrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl-methacrylate, vinyl pyridine, aminoethyl methacrylates, 2-methacryloyloxy-trimethylammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenylisocyanate), including combinations thereof. Preferable polymers include polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), and polyamide (nylon) polymers. Preferable copolymers include the following: polyvinylidene-polyacrylonitrile, polyvinylidene-polyacrylonitrile-polymethylmethacrylate, polystyrene-polyacrylonitrile and poly d-1, lactide co-glycolide polymers. A preferred copolymer is polyvinylidene-polyacrylonitrile. Other suitable biocompatible monomers and polymers will be apparent to those skilled in the art, in view of the present disclosure.

Stabilizing materials and vesicles may be prepared from other materials, provided that they meet the stability and other criteria set forth herein. Materials for preparing the vesicles may be basic and fundamental, and may form the primary basis for creating or establishing the stabilized materials, such as gas and gaseous precursor filled vesicles. For example, surfactants and fluorosurfactants may be basic and fundamental materials for preparing stabilizing materials and vesicles. On the other hand, the materials may be auxiliary, and act as subsidiary or supplementary agents which may enhance the functioning of the basic stabilizing material(s), or contribute some desired property in addition to that afforded by the basic stabilizing material(s).

It is not always possible to determine whether a given material is a basic or an auxiliary agent, since the functioning of the material is determined empirically, for example, by the results produced with respect to producing stabilized materials or vesicles. As an example of how the basic and auxiliary materials may function, it has been observed that the simple combination of a biocompatible lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may also be undesirable where the undissolved particulate matter has a diameter of greater than about 7 μm, and especially greater than about 10 μm. Manufacturing steps, such as sterile filtration, may also be problematic with solutions which contain undissolved particulate matter. Thus, propylene glycol may be added to remove this cloudiness by facilitating dispersion or dissolution of the lipid particles. Propylene glycol may also function as a wetting agent which can improve vesicle formation and stabilization by increasing the surface tension on the vesicle membrane or skin. It is possible that propylene glycol can also function as an additional layer that may coat the membrane or skin of the vesicle, thus providing additional stabilization. The conventional surfactants-set forth in D'Arrigo, U.S. Pat. Nos. 4,684,479 and 5,215,680, the disclosures of each of which are hereby incorporated by reference herein in their entirety, may be used as basic or auxiliary stabilizing materials in the present invention.

Additional auxiliary and basic stabilizing materials include, for example, soybean oil, peanut oil, canola oil, olive oil, safflower oil, corn oil, or any other oil commonly known to be ingestible which is suitable for use as a stabilizing compound in accordance with the teachings herein. Other auxiliary and basic stabilizing materials are disclosed, for example, in U.S. application Ser. No. 08/444,754, filed May 15, 1995, the disclosure of which is hereby incorporated herein by reference in its entirety.

Compounds used to make mixed micelle systems may be used as basic or auxiliary stabilizing materials, and include, for example, lauryltrimethylammonium bromide (dodecyl-), cetyltrimethylammonium bromide (hexadecyl-), myristyltrimethyl-ammonium bromide (tetradecyl-), alkyldimethylbenzylammonium chloride (where alkyl is $C_{12}$, $C_{14}$ or $C_{16}$,), benzyldimethyldodecylammonium bromide/chloride, benzyldimethyl hexadecyl-ammonium bromide/chloride, benzyldimethyl tetradecylammonium bromide/chloride, cetyldimethylethylammonium bromide/chloride, or cetylpyridinium bromide/chloride.

It may be possible to enhance the stability of stabilizing materials or vesicles by incorporating in the stabilizing materials and/or vesicles at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which are proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles.

The lipids used, especially in connection with vesicles, are preferably flexible. This means, in the context of the present invention, that the vesicles can alter their shape, for example, to pass through an opening having a diameter that is smaller than the diameter of the vesicle.

In certain embodiments, the vesicle composition may contain, in whole or in part, a fluorinated (including perfluorinated) compound. Suitable fluorinated compounds include, for example, fluorinated surfactants, including alkyl surfactants, and amphiphilic compounds. A wide variety of such compounds may be employed, including, for example, the class of compounds which are commercially available as ZONYL® fluorosurfactants (the DuPont Company, Wilmington, Del.), including the ZONYL® phosphate salts (e.g., $[F(CF_2CF_2)_{3-8}CH_2CH_2O]_{1,2}P(O)(O^-NH_4^+)_{2,1}$) which have term phosphate groups and ZONYL® sulfate salts which have terminal sulfate groups (e.g., $F(CF_2CF_2)_{3-8}CH_2CH_2SCH_2CH_2N^+(CH_3)_3{}^-OSO_2OCH_3$). Suitable ZONYL® surfactants also include, for example, ZONYL® surfactants identified as Telomer B, including Telomer B surfactants which are pegylated (i.e., have at least one polyethylene glycol group attached thereto), also known as PEG-Telomer B, available from the DuPont Company.

Alternatively, it may be desirable to use a fluorinated compound, especially a perfluorocarbon compound, which may be in the liquid state at the temperature of use, including, for example, the in vivo temperature of the human body, to assist or enhance the stability of the lipid and/or vesicle compositions, and especially, gas filled vesicles. Suitable liquid perfluorocarbons which may be used include, for example, perfluorodecalin, perfluorododecalin, perfluorooctyliodide, perfluorooctylbromide, perfluorotripropylamine, and perfluorotributylamine. In general, perfluorocarbons comprising about six or more carbon atoms will be liquids at normal human body temperature. Among these perfluorocarbons, perfluorooctylbromide and perfluorohexane, which are liquids at room temperature, are preferred. The gas which is present may be, for example, nitrogen or perfluoropropane, or may be derived from a gaseous precursor, which may also be a perfluorocarbon, for example, perfluoropentane. In the latter case, the lipid stabilizing materials and/or vesicle compositions may be prepared from a mixture of perfluorocarbons, which for the examples given, would be perfluoropropane (gas) or perfluoropentane (gaseous precursor) and perfluorooctylbromide (liquid). Although not intending to be bound by any theory or theories of operation, it is believed that, in the case of vesicle compositions, the liquid fluorinated compound may be situated at the interface between the gas and the membrane or wall surface of the vesicle. There may be thus formed a further stabilizing layer of liquid fluorinated compound on the internal surface of the stabilizing compound, for example, a biocompatible lipid used to form the vesicle, and this perfluorocarbon layer may also prevent the gas from difflusing through the vesicle membrane. A gaseous precursor, within the context of the present invention, is a liquid at the temperature of manufacture and/or storage, but becomes a gas at least at or during the time of use.

A liquid fluorinated compound, such as a perfluorocarbon, when combined with a gas and/or gaseous precursor ordinarily used to make the lipid and/or vesicles described herein, may confer an added degree of stability not otherwise obtainable with the gas and/or gaseous precursor alone. Thus, it is within the scope of the present invention to utilize a gas and/or gaseous precursor, such as a perfluorocarbon gaseous precursor, for example, perfluoropentane, together with a perfluorocarbon which remains liquid after administration to a patient, that is, whose liquid to gas phase transition temperature is above the body temperature of the patient, for example, perfluorooctylbromide. Perfluorinated surfactants, such as the DuPont Company's ZONYL® fluorinated surfactants, ZONYL® phosphate salts, ZONYL® sulfate salts, and ZONYL® surfactants identified as Telomer B, including Telomer B surfactants which are pegylated (i.e., have at least one polyethylene glycol group attached thereto), also known as PEG-Telomer B, may be used to stabilize the lipid and/or vesicle compositions, and to act, for example, as a coating for vesicles. Preferred perfluorinated surfactants are the partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the stabilizing materials and/or vesicles of the present invention.

Other suitable fluorinated compounds for use as the stabilizing materials and/or vesicles of the present invention are set forth in U.S. Pat. No. 5,562,893, the disclosure of which is hereby incorporated herein by reference in its entirety. For example, synthetic organic monomeric repeating units may be used to form polymers suitable as stabilizing materials in the present invention, including hydroxyacids, lactones, lactides, glycolides, acryl containing compounds, aminotriazol, orthoesters, anyhdrides, ester imides, imides, acetals, urethanes, vinyl alcohols, enolketones, and organosiloxanes.

The method of introducing fluorine into any of these materials is well known in the art. For example, the introduction of perfluoro-t-butyl moieties is described in U.S. Pat. No. 5,234,680, the disclosure of which is hereby incorporated by reference herein in its entirety. These methods generally involve the reaction of perfluoroalkyl carbanions with host molecules as follows: $(CF_3)_3C^-+R—X \rightarrow (CF_3)_3C—R$, where R is a host molecule and X is a good leaving group, such as bromine, chlorine, iodine or a sulfonato group. After adding a leaving group to the foregoing stabilizing material using methods well known in the art, perfluoro-t-butyl moieties can then be easily introduced to these derivatized stabilizing materials as described above.

Additional methods are known for the introduction of trifluoromethyl groups into various organic compounds are well known in the art. For example, trifluoromethyl groups may be introduced by nucleophilic perfluoroalkylation using perfluoroalkyl-trialkylsilanes.

Fluorine can be introduced into any of the aforementioned stabilizing materials or vesicles either in their monomeric or polymeric form. Preferably, fluorine moieties are introduced into monomers, such as fatty acids, amino acids or polymerizable synthetic organic compounds, which are then polymerized for subsequent use as stabilizing materials and/or vesicles.

The introduction of fluorine into stabilizing materials and/or vesicles may also be accomplished by forming vesicles in the presence of a perfluorocarbon gas. For example, when vesicles are formed from proteins, such as human serum albumin in the presence of a perfluorocarbon gas, such as perfluoropropane, using mechanical cavitation, fluorine from the gas phase becomes bound to the protein vesicles during formation. The presence of fluorine in the vesicles and/or stabilizing materials can be detected by NMR of vesicle debris which has been purified from disrupted vesicles. Fluorine can also be introduced into stabilizing materials and/or vesicles using other methods, such as sonication, spray-drying or emulsification techniques.

Another way in which fluorine can be introduced into the stabilizing materials is by using a fluorine-containing reactive compound. The term "reactive compound" refers to compounds which are capable of interacting with the stabilizing material and/or vesicle in such a manner that fluorine moieties become covalently attached to the stabilizing material and/or vesicle. When the stabilizing material is a protein, preferred reactive compounds are either alkyl esters or acyl halides which are capable of reacting with the protein's amino groups to form an amide linkage via an acylation reaction. The reactive compound can be introduced at any stage during vesicle formation, but is preferably added to the gas phase prior to vesicle formation. For example, when vesicles are to be made using mechanical or ultrasound cavitation techniques, the reactive compound can be added to the gas phase by bubbling the gas to be used in the formation of the vesicles (starting gas) through a solution of the reactive compound into the gas phase. The resultant gas mixture, which now contains the starting gas and the reactive compound, is then used to form vesicles. The vesicles are preferably formed by sonication of human serum albumin in the presence of a gas mixture, as described in U.S. Pat. No. 4,957,656, the disclosure of which is hereby incorporated herein by reference in its entirety.

Suitable fluorine containing alkyl esters and acyl halides for use as stabilizing materials and/or vesicle forming materials in the present invention include, for example, diethyl hexafluoroglutarate, diethyl tetrafluorosuccinate, methyl heptafluorobutyrate, ethyl heptafluorobutyrate, ethyl pentafluoropropionate, methyl pentafluoropropionate, ethyl perfluorooctanoate, methyl perfluorooctanoate, nonafluoropentanoyl chloride, perfluoropropionyl chloride, hexafluoroglutaryl chloride and heptafluorobutyryl chloride.

Other fluorine containing reactive compound can also be synthesized and used as the stabilizing materials and/or vesicle forming materials in the present invention, including, for example, aldehydes, isocyanates, isothiocyanates, epoxides, sulfonyl halides, anhydrides, acid halides and alkyl sulfonates, which contain perfluorocarbon moieties, including $—CF_3$, $—C_2F_5$, $—C_3F_4$ and $—C(CF_3)_3$. These reactive compounds can be used to introduce fluorine moieties into any of the aforementioned stabilizing materials by choosing a combination which is appropriate to achieve covalent attachment of the fluorine moiety.

Sufficient fluorine should be introduced to decrease the permeability of the vesicle to the aqueous environment. This will result in a slower rate of gas exchange with the aqueous environment which is evidenced by enhanced pressure resistance. Although the specific amount of fluorine necessary to stabilize the vesicle will depend on the components of the vesicle and the gas contained therein, after introduction of fluorine the vesicle will preferably contain 0.5 to 20% by weight, and more preferably about 1 to 10% by weight fluorine.

The materials from which the vesicles are constructed are preferably biocompatible lipid, protein, polymer or surfactant materials, and of these, the biocompatible lipids are preferred. In addition, because of the ease of formulation, including the capability of preparing vesicles immediately prior to administration, these vesicles may be conveniently made on site.

The stability of vesicles may be attributable, at least in part, to the materials from which the vesicles are made, including, for example, the lipids, polymers, proteins and/or surfactants described above, and it is often not necessary to employ additional stabilizing materials, although it is optional and may be preferred to do so. In addition to, or instead of, the lipid, protein and/or polymer compounds discussed above, the compositions described herein may comprise one or more other stabilizing materials. Exemplary stabilizing materials include, for example, surfactants and biocompatible polymers. The stabilizing materials may be employed to desirably assist in the formation of vesicles and/or to assure substantial encapsulation of the gases, gaseous precursors and/or bioactive agents. Even for relatively insoluble, non-diffuisible gases, such as perfluoropropane or sulfur hexafluoride, improved vesicle compositions may be obtained when one or more stabilizing materials are utilized in the formation of the gas and/or gaseous precursor filled vesicles. These compounds may help improve the stability and the integrity of the vesicles with regard to their size, shape and/or other attributes.

Like the polymers discussed above, the biocompatible polymers useful as stabilizing materials for preparing the gas and/or gaseous precursor filled vesicles may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, algiriic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethyl-cellulose, hydroxymethylcellulose, hydroxypropylmethylcellulose, methylcellulose, and methoxycellulose. Exemplary synthetic polymers include polyphosphazenes, polyethylenes (such as, for example, polyethylene glycol (including the class of compounds referred to as PLURONICS®, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of vesicles which employ polymers as stabilizing compounds will be readily apparent to those skilled in the art, in view of the present disclosure, when coupled with information known in the art, such as that described and referred to in Unger, U.S. Pat. No. 5,205,290, the disclosure of which is hereby incorporated herein by reference in its entirety.

Particularly preferred embodiments of the present invention involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinylalcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanol-amine-polyethylene glycol 5000 (DSPE-PEG5000).

In certain preferred embodiments of the present invention, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEG5000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

The terms "stable" or "stabilized" mean that the vesicles may be substantially resistant to degradation, including, for example, loss of vesicle structure or encapsulated gas, gaseous precursor and/or bioactive agent, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and/or gaseous precursor filled vesicles, may also be stable even under adverse conditions, such as temperatures and pressures which are above or below those experienced under normal ambient conditions.

The gas and/or gaseous precursor filled vesicles used in the present invention may be controlled according to size, solubility and heat stability by choosing from among the various additional or auxiliary stabilizing materials described herein. These materials can affect the parameters of the vesicles, especially vesicles formulated from lipids, not only by their physical interaction with the membranes, but also by their ability to modify the viscosity and surface tension of the surface of the gas and/or gaseous precursor filled vesicle. Accordingly, the gas and/or gaseous precursor filled vesicles used in the present invention may be favorably modified and further stabilized, for example, by the addition of one or more of a wide variety of (i) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (ii) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, poloxamer 181, PLURONICS® (BASF, Parsippany, N.J.), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (iii) suspending and/or viscosity-increasing agents, including, for example, acacia, agar, alginic acid, aluminum mono-stearate, bentonite, magma, carbomer 934P, carboxymethyl-cellulose, calcium and sodium and sodium 12, carrageenan, cellulose, dextran, gelatin, guar gum, locust bean gum, veegum, hydroxyethyl cellulose, hydroxypropyl methyl-cellulose, magnesium-aluminum-silicate, ZEOLITES®, methylcellulose, pectin, polyethylene oxide, povidone, propylene glycol alginate, silicon dioxide, sodium alginate, tragacanth, xanthan gum, α-d-gluconolactone, glycerol and mannitol; (iv) synthetic suspending agents, such as polyethylene glycol (PEG), polyvinylpyrrolidone (PVP), polyvinylalcohol (PVA), polypropylene glycol (PPG), and polysorbate; and (v) tonicity raising agents which stabilize and add tonicity, including, for example, sorbitol, mannitol, trehalose, sucrose, propylene glycol and glycerol.

The present lipid and/or vesicles are desirably formulated in an aqueous environment which can induce the lipid, because of its hydrophobic-hydrophilic nature, to form vesicles, which may be the most stable configuration which can be achieved in such an environment. The diluents which can be employed to create such an aqueous environment include, for example, water, including deionized water or water containing one or more dissolved solutes, such as salts or sugars, which preferably do not interfere with the formation and/or stability of the vesicles or their use as diagnostic agents, such as ultrasound contrast agents, MRI contrast agents, CT contrast agents and optical imaging contrast agents; and normal saline and physiological saline.

Gases and Gaseous Precursors

The present stabilizing materials or vesicles preferably comprise a gas, such as an inert gas. The gas provides the stabilizing materials or vesicles with enhanced reflectivity, particularly in connection with stabilizing materials or vesicles in which the gas is entrapped within the stabilizing materials or vesicles. This may increase their effectiveness as contrast agents or delivery vehicles.

Preferred gases are inert and biocompatible, and include, for example, air, noble gases, such as helium, rubidium, hyperpolarized xenon, hyperpolarized argon, hyperpolarized helium, neon, argon, xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases, and mixtures thereof. Exemplary fluorinated gases include fluorocarbon gases, such as perfluorocarbon gases and mixtures thereof. Paramagnetic gases, such as $^{17}O_2$ may also be used in the stabilizing materials and vesicles.

In certain preferred embodiments, a gas, for example, air or a perfluorocarbon gas, is combined with a liquid perfluorocarbon, such as perfluoropentane, perfluorohexane, perfluoroheptane, perfluorodecalin, perfluorododecalin, perfluorooctyliodide, perfluorooctylbromide, perfluorotripropylamine and perfluorotributylamine.

It may also be desirable to incorporate a precursor to a gaseous substance in the stabilizing materials or vesicles. Such precursors include materials that are capable of being converted to a gas in vivo, preferably where the gaseous precursor and gas produced are biocompatible.

In some embodiments the stabilizing materials may be formulated as emulsions or particles entrapping a central droplet of liquid perfluorocarbons, such as perfluorohexane or perfluorodecalin. Although a gas is preferred, liquid perfluorocarbons and liquid perfluoroethers add desirable properties such as fusogenicity (e.g., ability to fuse or tendency to bind to a membrane) and effectiveness of the resultant therapeutic delivery vehicles.

Among the gaseous precursors which are suitable for use in stabilizing materials and compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art in view of the present disclosure.

Gaseous precursors derived from salts are preferably selected from the group consisting of alkali metal salts, ammonium salts and mixtures thereof. More preferably, the salt is selected from the group consisting of carbonate, bicarbonate, sesquecarbonate, aminomalonate and mixtures thereof. Examples of suitable gaseous precursor materials which are derived from salts include, for example, lithium carbonate. sodium carbonate, potassium carbonate, lithium bicarbonate, sodium bicarbonate, potassium bicarbonate, magnesium carbonate, calcium carbonate, magnesium bicarbonate. ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, 9(3):525–532 (1970); Fitzpatrick et al., *Inorganic Chemistry*, 13(3):568–574 (1974); and Stelmashok et al., *Koordinatsionnaya Khimiya*, 3(4):524–527 (1977), the disclosures of which are hereby incorporated herein by reference in their entirety.

In addition to, or instead of, being sensitive to changes in pH, the gaseous precursor materials may also comprise compounds which are sensitive to changes in temperature. Exemplary of suitable gaseous precursors which are sensitive to changes in temperature are the perfluorocarbons. As the artisan will appreciate, a particular perfluorocarbon may exist in the liquid state when the lipid compositions are first made, and are thus used as a gaseous precursor. Alternatively, the perfluorocarbon may exist in the gaseous state when the lipid compositions are made, and are thus used directly as a gas. Whether the perfluorocarbon is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane can be useful as a gaseous precursor, although more likely as a gas, whereas perfluorohexane can be useful as a gaseous precursor because of its relatively high boiling point. As known to one of ordinary skill in the art, the effective boiling point of a substance may be related to the pressure to which that substance is exposed. This relationship is exemplified by the ideal gas law: $PV=nRT$, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

A wide variety of materials can be used as liquids, gases and gaseous precursors for entrapping within stabilizing materials and vesicles. For gaseous precursors, it is only required that the material be capable of undergoing a phase transition to the gas phase upon passing through the appropriate temperature. Exemplary gases and gaseous precursors for use in the present invention include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiene, 1-fluorobutane, 2-methylbutane, perfluorobutane, decafluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1, 1,1,4,4,4-hexafluorobutyne, 3-methyl-1-butyne, perfluoro-2-butyne, 2-bromobutyraldehyde, carbonyl sulfide, crotononitrile, cyclobutane, methylcyclobutane, octafluorocyclobutane, perfluorocyclobutene, 3-chlorocyclopentene, perfluorocyclopentane, octafluorocyclopentene, cyclopropane, perfluorocyclopropane, 1,2-dimethylcyclopropane, 1,1-dimethylcyclopropane, 1,2-dimethylcyclopropane, ethylcyclo-propane, methylcyclopropane, diacetylene, 3-ethyl-3-methyl diaziridine, 1,1,1-trifluorodiazoethane, dimethylamine, hexafluorodimethylamine, dimethylethylamine, bis(dimethyl-phosphine)amine, perfluoroethane, perfluoropropane, perfluoropentane, perfluorohexane, perfluoroheptane, perfluorooctane, perfluorononane, perfluorodecane, hexafluoroethane, hexafluoropropylene, octafluoropropane, octafluorocyclopentene, 1,1-dichlorofluoroethane, hexafluoro-2-butyne, octafluoro-2-butene, hexafluorobuta-1,3-diene, 2,3-dimethyl-2-norbomane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1, 2,2-trifluoroethane, 1,1-dichloroethane, 1,1-dichloroethylene, 1,1-dichloro-1,2-difluoroethylene, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2, 2-tetrafluoroethane, 2-chloro-1,1-difluoroethane, chloroethane, chloropentafluoroethane, dichlorotrifluoroethane, fluoroethane, nitropentaflouroethane, nitrosopentafluoroethane, perfluoroethylamine, ethyl vinyl ether, 1,1-dichloroethane, 1,1-dichloro-1,2-difluoroethane, 1,2-difluoroethane, 1,2-difluoroethylene, methane, trifluoromethanesulfonylchloride, trifluoromethanesulfenylchloride, (pentafluorothio)-trifluoromethane, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, perfluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neon, neopentane, nitrogen, nitrous oxide, 1,2,3-nonadecanetricarboxylic acid 2-hydroxytrimethyl ester, 1-nonene-3-yne, oxygen, 1,4-pentadiene, n-pentane, perfluoropentane, 4-amino-4-methylpentan-2-one, 1-pentene, 2-pentene (cis and trans), 3-bromopent-1-ene, perfluoropent-1-ene, tetrachlorophthalic acid, 2,3,6-trimethyl-piperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, 1-chloropropylene, chloropropylene-(trans), chloropropane-(trans), 2-chloropropane, 2-chloropropylene, 3-fluoropropane, 3-fluoropropylene, perfluoropropylene, perfluorotetrahydropyran, perfluoromethyl-tetrahydrofuran, perfluorobutylmethylether, perfluoromethylpentylether, propyne, 3,3,3-trifluoropropyne, 3-fluorostyrene, sulfur (di)-decafluoride ($S_2F_{10}$), sulfur hexafluoride, 2,4-diaminotoluene, trifluoroacetonitrile, trifluoromethyl peroxide, trifluoromethyl sulfide, tungsten hexafluoride, vinyl acetylene, vinyl ether and xenon.

Preferred gases and gaseous precursors are compounds which are sparingly soluble in water but which may, in some cases, be liposoluble, such as low molecular weight alkanes and their fluorinated analogs. Preferred gases and gaseous precursors include, for example, nitrogen, perfluorocarbons, sulfur hexafluoride, perfluoroether compounds and combinations thereof. The perfluorocarbons and perfluoroethers preferably have from 1 to 4 carbon atoms and from 4 to 10 fluorine atoms, most preferably perfluorobutane ($C_4F_{10}$). Preferred gaseous precursors generally have from about 4 to 8 carbon atoms, more preferably 5 or 6 carbon atoms, and from about 12 to 15 fluorine atoms. Perfluoroethers generally contain one or two oxygen atoms, preferably one oxygen atom. Preferred gaseous precursors include perfluoropentane, perfluorohexane, perfluorodecalin, perfluorotripropylamine, perfluorooctylbromide, perfluorobutylmethylether, perfluorotetrahydropyran, perfluoromethyltetrahydrofuran, perfluoromethylpentylether and other perfluoroether analogues containing between 4 and 6 carbon atoms, and optionally containing one halide ion, preferably Br$_1$-. For example, compounds having the structure $C_nF_yH_xOBr$, wherein n is an integer from 1 to 6, y is an integer from 0 to 13, and x is an integer from 0 to 13, are useful as gaseous precursors. Examples of useful gaseous precursors having this formula include perfluoropropyloxyl-bromide and 2-bromooxyperfluoropropane.

Also useful as gaseous precursors in the present invention are partially or fully fluorinated ethers, preferably having a boiling point of from about 36° C. to about 60° C. Fluorinated ethers are ethers in which one or more hydrogen atoms is replaced by a fluorine atom. For purposes of this invention, fluorinated ethers have the general formula $CX_3(CX_2)_n$—O—$(CX_2)_nCX_3$, wherein X is H, F or another halogen provided that at least one of X is fluorine. Generally, fluorinated ethers containing about 4 to about 6 carbon atoms will have a boiling point within the preferred range for the invention, although smaller or larger chain fluorinated ethers may also be employed in appropriate circumstances. Exemplary fluorinated ethers include compounds having the formulae $CF_3CF_2OCF_2CF_3$, $CF_3O(CF_2)_2CF_3$ and $CF_3OCF(CF_3)_2$.

In preferred embodiments, the gas comprises a fluorinated gas, which includes gases containing one or more than one fluorine atom. Preferred are gases which contain more than one fluorine atom, with perfluorocarbons (fully fluorinated fluorocarbons) being more preferred. The perfluorocarbon gas may be saturated, unsaturated or cyclic, including, for example, perfluoromethane, perfluoroethane, perfluoropropane, perfluorocyclopropane, perfluorobutane, perfluorocyclobutane, perfluoropentane, perfluorocylcopentane, perfluorohexane, perfluoroheptane, perfluorooctane, perfluorononane, and mixtures thereof. More preferably, the perfluorocarbon gas is perfluoropropane or perfluorobutane, with perfluoropropane being particularly preferred. Another preferable gas is sulfur hexafluoride. Yet another preferable gas is heptafluoropropane, including 1,1,1,2,3,3,3-heptafluoropropane and its isomer, 1,1,2,2,3,3,3-heptafluoropropane. Mixtures of different types of gases, such as mixtures of a perfluorocarbon gas and another type of gas, such as, for example, air or nitrogen, can also be used in the compositions of the present invention. Other gases, including the gases exemplified above, would be apparent to one skilled in the art in view of the present disclosure.

The gaseous precursor materials may be also photoactivated materials, such as a diazonium ion and aminomalonate. As discussed more fully hereinafter, certain stabilizing materials and/or vesicles, particularly vesicles, may be formulated so that gas is formed at the target tissue or by the action of sound on the stabilizing materials. Examples of gaseous precursors are described, for example, in U.S. Pat. Nos. 5,088,499 and 5,149,319, the disclosures of each of which are hereby incorporated herein by reference in their entirety. Other gaseous precursors, in addition to those exemplified above, will be apparent to one skilled in the art in view of the present disclosure.

The gases and/or gaseous precursors are preferably incorporated in the stabilizing materials and/or vesicles irrespective of the physical nature of the composition. Thus, it is contemplated that the gases and/or gaseous precursors may be incorporated, for example, in stabilizing materials in which the stabilizing materials are aggregated randomly, such as emulsions, dispersions or suspensions, as well as in vesicles, including vesicles which are formulated from lipids, such as micelles and liposomes. Incorporation of the gases and/or gaseous precursors in the stabilizing materials and/or vesicles may be achieved by using any of a number of methods. For example, in the case of vesicles based on lipids, the formation of gas filled vesicles can be achieved by shaking or otherwise agitating an aqueous mixture which comprises a gas and/or gaseous precursor and one or more lipids. This promotes the formation of stabilized vesicles within which the gas and/or gaseous precursor is encapsulated.

In addition, a gas may be bubbled directly into an aqueous mixture of stabilizing materials and/or vesicle-forming compounds. Alternatively, a gas instillation method can be used as disclosed, for example, in U.S. Pat. Nos. 5,352,435 and 5,228,446, the disclosures of each of which are hereby incorporated herein by reference in their entirety. Suitable methods for incorporating the gas and/or gaseous precursor in cationic lipid compositions are disclosed also in U.S. Pat. No. 4,865,836, the disclosure of which is hereby incorporated herein by reference in its entirety. Other methods would be apparent to one skilled in the art based on the present disclosure. Preferably, the gas may be instilled in the stabilizing materials and/or vesicles after or during the addition of the stabilizing material and/or during formation of vesicles.

In preferred embodiments, the gases and/or gaseous precursors are incorporated in vesicle compositions, with micelles and liposomes being preferred. Vesicles in which a gas or gaseous precursor or both are encapsulated are advantageous in that they provide improved reflectivity in vivo.

It is preferred that the stabilizing materials, and especially the vesicles, be formulated from lipids and optional stabilizing compounds to promote the formation of stable vesicles, as discussed in detail above. Additionally, it is preferred that the stabilizing materials and/or vesicles comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

Compositions employed herein may also include, with respect to their preparation, formation and use, gaseous precursors that can be activated to change from a liquid or solid state into a gas by temperature, pH, light, and energy (such as ultrasound). The gaseous precursors may be made into gas by storing the precursors at reduced pressure. For example, a vial stored under reduced pressure may create a headspace of perfluoropentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified droplets that would be required to form a vesicle of a maximum size of 10 μm.

TABLE 1

Physical Characteristics of Gaseous Precursors and
Diameter of Emulsified Droplet to Form a 10 μm Vesicle*

| Compound | Molecular Weight | Boiling Point (° C.) | Density | Diameter (μm) of emulsified droplet to make 10 micron vesicle |
|---|---|---|---|---|
| perfluoro pentane | 288.04 | 28.5 | 1.7326 | 2.9 |
| 1-fluorobutane | 76.11 | 32.5 | 0.67789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics, Robert C. Weast and David R. Lide, eds., CRC Press, Inc. Boca Raton, Florida (1989–1990).

As noted above, it is preferred to optimize the utility of the stabilizing materials and/or vesicles, especially vesicles formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book*, 1966, Matheson Company Inc. More preferably, the gas entrapped in the vesicle possesses a solubility in water less than that of air; and even more preferably, the gas entrapped in the vesicle possesses a solubility in water less than that of nitrogen.

It may be desirable, in certain embodiments, to formulate vesicles from substantially impermeable polymeric materials. In these embodiments, it is generally unnecessary to employ a gas which is highly insoluble. For example, stable vesicles which comprise substantially impermeable polymeric materials may be formulated with gases having higher solubilities, for example, air or nitrogen.

Targeting Ligands

The compounds, compositions and stabilizing materials of the present invention may also comprise a targeting ligand. Targeting ligands are preferably associated with the prodrug and/or stabilizing materials and/or vesicles covalently or non-covalently. In the case of stabilizing materials, the targeting ligand may be bound, for example, via a covalent or non-covalent bond, to at least one of the lipids, proteins, polymers or surfactants incorporated in the stabilizing materials. In the case of the steroid prodrugs, the targeting ligand may be covalently bound to a reactive moiety on the steroid prodrug or may be bound by a spacer or linker molecule with a reactive end such as an amine, hydroxyl, or carboxylic acid functional group.

Preferably, the targeting ligand is bound to the prodrug, stabilizing materials and/or vesicles covalently. In the case of lipid compositions which comprise cholesterol, the targeting ligand is preferably bound to the cholesterol substantially only non-covalently, and/or the targeting ligand is bound covalently to a component of the composition, for example, another lipid, such as a phospholipid, other than the cholesterol.

If desired, the targeting ligands may also be bound to other stabilizing materials, for example, biocompatible polymers or surfactants, which may be present in the compositions. The targeting ligands which are incorporated in the compositions of the present invention are preferably substances which are capable of targeting receptors and/or tissues in vivo or in vitro. With respect to the targeting of tissue, the targeting ligands are desirably capable of targeting heart tissue and membranous tissues, including endothelial and epithelial cells. In the case of receptors, the targeting ligands are desirably capable of targeting lymphocyte receptors, such as T-cells, B-cells or interleukin-2 receptors. It is contemplated that preferred targeting ligands for use in targeting tissues and/or receptors, including the tissues and receptors exemplified above, are selected from the group consisting of proteins, including antibodies, antibody fragments, hormones, hormone analogues, glycoproteins and lectins, peptides, polypeptides, amino acids, sugars, such as saccharides, including monosaccharides and polysaccharides, and carbohydrates, vitamins, steroids, steroid analogs, hormones, cofactors, bioactive agents, and genetic material, including nucleosides, nucleotides, nucleotide acid constructs and polynucleotides, with peptides being particularly preferred.

Generally speaking, peptides which are particularly useful as targeting ligands include natural, modified natural, or synthetic peptides that incorporate additional modes of resistance to degradation by vascularly circulating esterases, amidases, or peptidases. One very useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization is also particularly useful in inducing stability. In addition, an end-to-side chain cyclization may be a useful modification as well. In addition, the substitution of an L-amino acid for a D-amino acid in a strategic region of the peptide may offer resistance to biological degradation. Suitable targeting ligands, and methods for their preparation, will be readily apparent to one skilled in the art, in view of the disclosure herein.

Preferred targeting ligands in the present invention include cell adhesion molecules (CAM), among which are, for example, cytokines, integrins, cadherins, immunoglobulins and selectins, all of which are discussed in detail below.

In connection with the targeting of endothelial cells, suitable targeting ligands include, for example, one or more of the following: growth factors, including, for example, basic fibroblast growth factor (bFGF), acidic fibroblast growth factor (aFGF), transforming growth factor-alpha (TGF-α), transforming growth factor-beta (TGF-β), platelet-derived endothelial cell growth factor (PD-ECGF) vascular endothelial growth factor (VEGF) and human growth factor (HGF); angiogenin; tumor necrosis factors, including tumor necrosis factor-alpha (TNF-α) and tumor necrosis factor-beta (TNF-β), and receptor antibodies and fragments thereof to tumor necrosis factor (TNF) receptor 1 or 2 family, including, for example, TNF-R1, TNF-R2, FAS, TNFR-RP, NGF-R, CD30, CD40, CD27, OX40 and 4-1BB; copper-containing polyribonucleotide angiotropin with a molecular weight of about 4,500, as well as low molecular weight non-peptide angiogenic factors, such as 1-butyryl glycerol; the prostaglandins, including, for example, prostaglandin $E_1$ ($PGE_1$) and prostaglandin $E_2$ ($PGE_2$); nicotinamide; adenosine; dipyridamole; dobutamine; hyaluronic acid degradation products, such as, for example, degradation products resulting from hydrolysis of β linkages, including hyalobiuronic acid; angiogenesis inhibitors, including, for example, collagenase inhibitors; minocycline; medroxyprogesterone; chitin chemically modified with 6-O-sulfate and 6-O-carboxymethyl groups; angiostatic steroids, such as tetrahydrocortisol; and heparin, including fragments of heparin, such as, for example, fragments having a molecular weight of about 6,000, admixed with steroids, such as, for example, cortisone or hydrocortisone; angiogenesis inhibitors, including angioinhibin (AGM-1470- an angiostatic antibiotic); platelet factor 4; protamine; sulfated polysaccharide peptidoglycan complexes derived from the bacterial wall of an Arthobacter species; fungal-derived angiogenesis inhibitors, such as fumagillin derived from *Aspergillus fumigatus*; D-penicillamine; gold thiomalate; thrombospondin; vitamin $D_3$ analogues, including, for example, 1-α, 25-dihydroxyvitamin $D_3$ and a synthetic analogue 22-oxa-1-α, 25-dihydroxyvitamin $D_3$; interferons, including, for example, α-interferon, β-interferon and γ-interferon; cytokines and cytokine fragments, such as the interleukins, including, for example, interleukin-1 (IL-1), interleukin-2 (IL-2), interleukin-3 (IL-3), interleukin-5 (IL-5) and interleukin-8 (IL-8); erythropoietin; a 20-mer peptide or smaller for binding to receptor or antagonists to native cytokines; granulocyte macrophage colony stimulating factor (GMCSF); $LTB_4$ leukocyte receptor antagonists; heparin, including low molecular weight fragments of heparin or analogues of heparin; simple sulfated polysaccharides, such as cyclodextrins, including α-, β- and γ-cyclodextrin; tetradecasulfate; transferrin; ferritin; platelet factor 4; protamine; Gly-His-Lys complexed to copper; ceruloplasmin; (12R)-hydroxyeicosatrienoic acid; okadaic acid; lectins; antibodies; CD11a/CD18; and Very Late Activation Integrin-4 (VLA-4).

In another embodiment, small peptides which bind the interluekin-1 (IL-1) receptor may be used. For example, peptides generated by phage display core sequences of QPY have been shown to be essential for peptide binding, including, for example, AF12198, a 15-mer with a core sequence of WYQJY SEQ ID NO: 15, where J is azetidine; and IL-1 antagonists with $K_d 10^{-10}$ to 10–12M, such as AcPhe-Glu, Trp-Pro-Gly-Trp- Tyr-Gln-Aze-Tyr-Ala-Leu-Pro-Leu-$CONH_2$ SEQ ID NO: 16 or Ac-Phe-Glu-Trp-Pro-Gly- Trp-Tyr-Gln-Aze-Tyr-Ala-Leu-Pro-Leu-Endothelial-leukocyte SEQ ID NO: 17 adhesion molecules (ELAM's) are antigens which are expressed by endothelial cells under conditions of stress which then facilitate the migration of the leukocytes across the endothelium lining the vasculature into the surrounding tissues. It is also the surprising discovery that these same endothelial-leukocyte adhesion molecules may be advantageously exploited as receptors for targeting of vesicles. These endothelial cell adhesion molecules belong to a family known as selectins in which the known members, such as GMP-140, all participate in endothelial-leukocyte adhesion and include ELAM-1, LAM-1 and the granule membrane protein 140 (GMP-140) also known as platelet activation-dependent granule-external membrane protein (PADGEM), VCAM-1/INCAM-110 (Vascular Adhesion Molecule/Inducible Adhesion Molecule) and ICAM-1 (Intercellular Adhesion Molecule).

The cadherin family of cell adhesion molecules may also be used as targeting ligands, including for example, the E-, N-, and P-cadherins, cadherin-4, cadherin-5, cadherin-6, cadherin-7, cadherin-8, cadherin-9, cadherin-10, and cadherin-11; and most preferably cadherin C-5. Further, antibodies directed to cadherins, such as, for example, the monoclonal antibody Ec6C10, may be used to recognize cadherins expressed locally by specific endothelial cells.

A wide variety of different targeting ligands can be selected to bind to the cytoplasmic domains of the ELAM molecules. Targeting ligands in this regard may include lectins, a wide variety of carbohydrate or sugar moieties, antibodies, antibody fragments, Fab fragments, such as, for example, Fab'2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of different combinatorial chemistry techniques as are now known in the art. Targeting ligands derived or modified from human leukocyte origin, such as CD11a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting ligand. VLA-4, derived from human monocytes, may be used to target VCAM-1. Antibodies and other targeting ligands may be employed to target endoglin, which is an endothelial cell proliferation marker. Endoglin is upregulated on endothelial cells in miscellaneous solid tumors. A targeting ligand which may be used to target endoglin is the antibody TEC-11. R. E. Thorpe and F. J. Burrows, *Breast Cancer Research and Treatment*, 36:237–51 (1995).

As with the endothelial cells discussed above, a wide variety of peptides, proteins and antibodies may be employed as targeting ligands for targeting epithelial cells. Preferably, a peptide, including synthetic, semi-synthetic or naturally-occurring peptides, with high affinity to the epithelial cell target receptor may be selected, with synthetic peptides being more preferred. In connection with these preferred embodiments, peptides having from about 5 to about 15 amino acid residues are preferred. Antibodies may be used as whole antibody or antibody fragments, for example, Fab or Fab'2, either of natural or recombinant origin. The antibodies of natural origin may be of animal or human origin, or may be chimeric (mouse/human). Human recombinant or chimeric antibodies are preferred and fragments are preferred to whole antibody.

Examples of monoclonal antibodies which may be employed as targeting ligands in the present compositions include CALAM 27, which is formed by immunizing BALB/c mice with whole human squamous cell carcinoma of the tongue and forming hybridomas by crossing extracted spleen cells with those of an NS1 syngeneic myeloma cell line. Gioanni, J. et al., *Cancer Research*, 47: 4417–4424 (1987). CALAM 27 is directed to surface epitopes of both normal and malignant epithelial cells. Normal lymph nodes generally do not contain cells expressing these epitopes. See *Cancer Research*, 47:4417–4424 (1987). Accordingly, lipid and/or vesicle compositions comprising this antibody can be used to target metastases in the lymph nodes. The monoclonal antibody 3C2 may be employed as a targeting ligand for targeting malignant epithelial cells of serious ovarian carcinoma and endometrioid carcinoma. Another exemplary targeting ligand is Mab 4C7 (see *Cancer Research*, 45:2358–2362 (1985)), which may be used to target mucinous carcinoma, endometriod carcinoma and mesonephroid carcinoma. For targeting squamous cell carcinoma in head and neck cancer, Mab E48 (*Biological Abstract*, Vol. 099 Issue. 066 Ref. 082748) may be used as a targeting ligand. For targeting malignant melanoma, the monoclonal antibody 225.28s (*Pathol. Biol.*, 38 (8):866–869 (1990)) may be employed. The monoclonal antibody mAb2E$_1$, which is targeted to EPR-1 (effector cell protease 1), may also be used.

Targeting ligands may be selected for targeting antigens, including antigens associated with breast cancer, such as epidermal growth factor receptor (EGFR), fibroblast growth factor receptor, erbB2/HER-2 and tumor associated carbohydrate antigens (*Cancer*, 74 (3):1006–12 (1994)). CTA 16.88, homologous to cytokeratins 8, 18 and 19, is expressed by most epithelial-derived tumors, including carcinomas of the colon, pancreas, breast, ovary and lung. Thus, antibodies directed to these cytokeratins, such as 16.88 (IgM) and 88BV59 (IgG3k), which recognize different epitopes on CTA 16.88 (*Semin. Nucl. Med.*, 23 (2): 165–79 (1993)), may be employed as targeting ligands. For targeting colon cancer, anti-CEA IgG Fab' fragments may be employed as targeting ligands. Chemically conjugated bispecific anti-cell surface antigen, anti-hapten Fab'-Fab antibodies may also be used as targeting ligands. The MG series monoclonal antibodies may be selected for targeting, for example, gastric cancer (*Chin. Med. Sci. J.*, 6 (1):56–59 (1991).

There are a variety of cell surface epitopes on epithelial cells for which targeting ligands may be selected. For example, the protein human papilloma virus (HPV) has been associated with benign and malignant epithelial proliferations in skin and mucosa. Two HPV oncogenic proteins, E6 and E7, may be targeted as these may be expressed in certain epithelial derived cancers, such as cervical carcinoma. See *Curr. Opin. Immunol.*, 6 (5):746–54 (1994). Membrane receptors for peptide growth factors (PGF-R), which are involved in cancer cell proliferation, may also be selected as tumor antigens. *Anticancer Drugs*, 5(4):379–93 (1994). Also, epidermal growth factor (EGF) and interleukin-2 may be targeted with suitable targeting ligands, including peptides, which bind these receptors. Certain melanoma associated antigens (MAA), such as epidermal growth factor receptor (EGFR) and adhesion molecules (*Tumor Biol.*, 15 (4):188–202 (1994)), which are expressed by malignant melanoma cells, can be targeted with the compositions provided herein. The tumor associated antigen FAB-72 on the surface of carcinoma cells may also be selected as a target.

A wide variety of targeting ligands may be selected for targeting myocardial cells. Exemplary targeting ligands include, for example, anticardiomyosin antibody, which may comprise polyclonal antibody, Fab'2 fragments, or be of human origin, animal origin, for example, mouse origin, or of chimeric origin. Additional targeting ligands include dipyridamole; digitalis; nifedipine; apolipoprotein; low density lipoproteins (LDL), including α-LDL, vLDL and methyl LDL; ryanodine; endothelin; complement receptor type 1; IgG Fc; beta 1-adrenergic; dihydropyridine; adenosine; mineralocorticoid; nicotinic acetylcholine and muscarinic acetylcholine; antibodies to the human alpha 1A-adrenergic receptor; bioactive agents, such as drugs, including the alpha 1-antagonist prazosin; antibodies to the anti-beta-receptor; drugs which bind to the anti-beta-receptor; anti-cardiac RyR antibodies; endothelin-1, which is an endothelial cell-derived vasoconstrictor peptide that exerts a potent positive inotropic effect on cardiac tissue (endothelin-1 binds to cardiac sarcolemmal vesicles); monoclonal antibodies which may be generated to the T-cell receptor α -β receptor and thereby employed to generate targeting ligands; the complement inhibitor sCR1; drugs, peptides or antibodies which are generated to the dihydropyridine receptor; monoclonal antibodies directed towards the anti-interleukin-2 receptor may be used as targeting ligands to direct the present compositions to areas of myocardial tissue which express this receptor and which may be up-regulated in conditions of inflammation; cyclosporine for directing similarly the compositions to areas of inflamed myocardial tissue; methylisobutyl isonitrile; lectins which bind to specific sugars on membranes of cardiac myocytes and cardiac endothelial cells; adrenomedullin (ADM), which is an endogenous hypotensive and vasorelaxing peptide; atrial natriuretic peptide (ANP); C-type natriuretic peptide (CNP), which is a 22 amino acid peptide of endothelial cell origin and is structurally related to atrial natriuretic peptide but genetically distinct, and possesses vasoactive and antimitogenic activity; vasonatrin peptide (VNP) which is a chimera of atrial natriuretic peptide (ANP) and C-type natriuretic peptide (CNP) and comprises 27 amino acids; thrombin; endothelium-derived relaxing factor (EDRF); neutral endopeptidase 1 (NEP-1); competitive inhibitors to EDRF, including, for example, NG-monomethyl-L-arginine (L-NMMA); potassium channel antagonists, such as charybdotoxin and glibenclamide; antiheart antibodies, which may be identified in patients with idiopathic dilated cardiomyopathy but which preferably do not elicit cytolysis in the myocardium; antibodies directed against the adenine nucleotide translocator, the branched-chain keto acid dehydrogenase or cardiac myosin; specific antagonists for the endothelin-A receptor, which may be referred to as BQ-123; and antibodies to the angiotensin II receptor.

Two of the major antigens of heart sarcolemmal are calcium binding glycoproteins which copurify with the dihydropyridine receptor. Antisera may be raised, including polyclonal or monoclonal antibodies, against purified sarcolemma. These antibodies may also be employed as targeted ligands. Purified fractions of the calcium binding glycoproteins may be isolated from the plasma membranes of the sarcolemma and then used to generate antibodies. ANP, which, as noted above, may be used as a targeting ligand, can be obtained from cultures of human aortic endothelial cells. ANP is generally localized in endothelium, but also may localize to the endothelial or myocardial tissue. ANP may be prepared, for example, using recombinant techniques, as well as by synthesis of the peptide using peptide synthesis techniques well known to those skilled in the art. It is also possible to use an antibody, either polyclonal or monoclonal, directed towards ANP. Similarly, a peptide directed to ANP may be used for targeting endothelial and/or myocardial cells. Both the β and α forms of atrial natriuretic factor may be used as potential targeting ligands for directing the present compositions to myocardial tissue.

A preferred embodiment of the present invention involves the selective targeting of steroid prodrugs to lymphocytes. The steroid prodrug can be incorporated into a delivery vehicle or may be used by itself for targeting to lymphocytes. Preferably a delivery vehicle is used and the preferred delivery vehicle comprises a stabilizing material, such as an emulsion or a gas-filled vesicle, more preferably a gas-filled liposome. Additionally, a targeted ligand may be incorporated into the delivery vehicle.

The targeting ligand is preferably covalently bound to the surface of the delivery vehicle by a spacer including, for example, hydrophilic polymers, preferably polyethylene glycol. Preferred molecular weights of the polymers are from 1000 da to 10,000 da, with 500 da being most preferred. Preferably the polymer is bifunctional with the targeting ligand bound to a terminus of the polymer. Generally, the targeting ligand will range from 0.1 to 20 mole percent of the exterior components of the vesicle. In the case of gas-filled lipid vesicles, this amount is preferably between 0.5 and 10 mole percent with 1 to 10 percent most preferred. The exact ratio will depend upon the particular targeting ligand.

In one embodiment of the invention, the targeting ligands are directed toward lymphocytes which may be T-cells or B-cells, with T-cells being the preferred target. Depending on the targeting ligand, the steroid prodrug vehicle may be targeted to one or more classes or clones of T-cells.

To select a class of targeted lymphocytes, a targeting ligand having specific affinity for that class is employed. For example, an anti CD-4 antibody can be used for selecting the class of T-cells harboring CD-4 receptors, an anti CD-8 antibody can be used for selecting the class of T-cells harboring CD-8 receptors, an anti CD-34 antibody can be used for selecting the class of T-cells harboring CD-34 receptors, etc. A lower molecular weight ligand is preferably employed, e.g., Fab or a peptide fragment. For example, an OKT3 antibody or OKT3 antibody fragment may be used.

When a receptor for a class of T-cells or clones of T-cells is selected, the steroid prodrug will be delivered to that class of cells. Using HLA-derived peptides, for example, will allow selection of targeted clones of cells expressing reactivity to HLA proteins.

The ultimate purpose of the linkage between the targeting ligand and the target may be the delivery of the steroid prodrug to the cell for endocytosis or fusion. Although not intending to be bound by any particular theory of operation, once the delivery vehicle has linked to its target, the steroid prodrug may gain access to the interior of the target cell either through a fusion-initiated capping and patching mechanism, the intervention of clathrin-coated pits or through classical endocytosis, depending on the mechanisms for engulfment peculiar to the target cell, or by other natural or induced means. The steroid, such as dexamethasone, then stimulates programmed cell death (apoptosis) through its well-established cytotoxicity. Those skilled in the art will recognize the potential for other such targeted uses of steroids which gain access to the target cells or tissue via ligand-receptor binding.

The following tables illustrate ligands from the MHC (major histocompatability complex) and their receptors in the class of T-cells for which they have affinity. All the ligands, T-cell receptors and peptide sequences in the table below may be used in the present invention.

TABLE 2

MHC LIGANDS AND T-CELL RECEPTORS

| T-Cell Receptor | Ligand | Peptide Sequence |
|---|---|---|
| HTB157.7 | $K^b$(Q10b hybrid) | Heterogeneous |
| HTB157.7 | $pK^b$163–174 | NA |

TABLE 2-continued

MHC LIGANDS AND T-CELL RECEPTORS

| T-Cell Receptor | Ligand | Peptide Sequence |
|---|---|---|
| 2C | $L^d$/p2Ca | LSPFPFDL* |
|  |  | SEQ ID NO: 1 |
| 2C | $L^d$/p2Ca-A5 | LSPFAFDL |
|  |  | SEQ ID NO: 2 |
| 2C | $L^d$/p2Ca-A3 | LSAFPFDL |
|  |  | SEQ ID NO: 3 |
| 2C | $L^d$/p2Ca-A8 | LSPFPFDA |
|  |  | SEQ ID NO: 4 |
| 2C | $L^d$/SL9 | SPFPFDLLL |
|  |  | SEQ ID NO: 5 |
| 2C | $K^b$/p2Ca | LSPFPFDL |
|  |  | SEQ ID NO: 6 |
| 2C | $L^d$/QL9 | QLSPSPDL |
|  |  | SEQ ID NO: 7 |
| 4G3 | $K^b$/pOV8 | SIINFEKL |
|  |  | SEQ ID NO: 8 |
| 2C | $L^d$/p2Ca-Y4 | LSPYPFDL |
|  |  | SEQ ID NO: 9 |
| 2C | $L^d$/p2Ca-A1 | ASPFPFDL |
|  |  | SEQ ID NO: 10 |
| Clone 30 | $K^b$/IgG (bivalent) | Heterogeneous |
| 14.3d | 1-$E^d$/pHA | SSFGAFGIFPK |
|  |  | SEQ ID NO: 11 |
| 5C.C7 | 1-$E^k$/MCC | ANERADLIAYLKQATK |
|  |  | SEQ ID NO: 12 |
| 228.4 | 1-$E^k$/MCC-K99A | ANERADLIAYLKQATK |
|  |  | SEQ ID NO: 12 |
| 2B4 | 1-$E^k$/MCC | ANERADLIAYLKQATK |
|  |  | SEQ ID NO: 12 |
| 2B4 | 1-$E^k$/PCC | ANERADLIAYLKQATAK |
|  |  | SEQ ID NO: 13 |
| 2B4 | 1-$E^k$/MCC-T102S | ANERADLIAYLKQASK |
|  |  | SEQ ID NO: 14 |
| HA1.7 | SEB |  |
| 14.3d β | SEC1 |  |
| 14.3d β | SEC2 |  |
| 14.3d β | SEC3 |  |
| 14.3d β | SEB |  |
| 14.3d β | SPEA |  |

*Single-letter code for amino acids.
Summarized from Fremont et al, Current Opinion In Immunology, (1996) 8:93–100, page 96, Table 2, the disclosure of which is hereby incorporated herein by reference in its entirety.

Another major area for targeted prodrug delivery involves the interlekin-2 (IL-2) system. IL-2 is a t-cell growth factor produced following antigen or mitogen induced stimulation of lymphoid cells. Among the cell types which produce IL-2 are $CD4^+$ and $CD8^+$ t-cells and large granular lymphocytes, as well as certain t-cell tumors. IL-2 receptors are glycoproteins expressed on responsive cells. They are notable in connection with the present invention because they are readily endocytosed into lysosomal inclusions when bound to IL-2. The ultimate effect of this endocytosis depends on the target cell, but among the notable in vivo effects are regression of transplantable murine tumors, human melanoma or renal cell cancer. IL-2 has also been implicated in antibacterial and antiviral therapies and plays a role in allograft rejection. In addition to IL-2 receptors, preferred targets include the anti-IL-2 receptor antibody, natural IL-2 and an IL-2 fragment of a 20-mer peptide or smaller generated by phage display which binds to the IL-2 receptor.

Although not intending to be bound by any particular theory of operation, IL-2 can be conjugated to the steroid prodrugs and/or other delivery vehicles and thus mediate the targeting of cells bearing IL-2 receptors. Endocytosis of the ligand-receptor complex would then deliver the steroid to the targeted cell, thereby inducing its death through apoptosis—independent and superceding any proliferative or activating effect which IL-2 would promote alone.

Additionally, an IL-2 peptide fragment which has binding affinity for IL-2 receptors can be incorporated either by direct attachment to a reactive moiety on the steroid prodrug or via a spacer or linker molecule with a reactive end such as an amine, hydroxyl, or carboxylic acid functional group. Such linkers are well known in the art and may comprise from 3 to 20 amino acid residues. Alternatively, D-amino acids or derivatized amino acids may be used which avoid proteolysis in the target tissue.

Still other systems which can be used in the present invention include IgM-mediated endocytosis in B-cells or a variant of the ligand-receptor interactions described above wherein the T-cell receptor is CD2 and the ligand is lymphocyte function-associated antigen 3 (LFA-3), as described, for example, by Wallner et al, *J. Experimental Med.*, 166:923–932 (1987), the disclosure of which is hereby incorporated by reference herein in its entirety.

The targeting ligand may be incorporated in the present stabilizing materials in a variety of ways. Generally speaking, the targeting ligand may be incorporated in the present stabilizing materials by being associated covalently or non-covalently with one or more of the stabilizing materials which are included in the compositions including, for example, the prodrugs, lipids, proteins, polymers, surfactants, and/or auxiliary stabilizing materials. In preferred form, the targeting ligand may be associated covalently with one or more of the aforementioned materials contained in the present stabilizing materials. Preferred stabilizing materials of the present invention comprise prodrugs, lipid, protein, polymer or surfactant compounds. In these compositions, the targeting ligands are preferably associated covalently with the prodrug, lipid, protein, polymer or surfactant compounds.

Exemplary covalent bonds by which the targeting ligands are associated with the stabilizing materials, including prodrugs, lipids, proteins, polymers, surfactants and/or vesicles include, for example, amide (—CONH—); thioamide (—CSNH—); ether (ROR'), where R and R' may be the same or different and are other than hydrogen); ester (—COO—); thioester (—COS—); —O—; —S—; —S$_n$—, where n is greater than 1, preferably about 2 to about 8, and more preferably about 2; carbamates; —NH—; —NR—, where R is alkyl, for example, alkyl of from 1 to about 4 carbons; urethane; and substituted imidate; and combinations of two or more of these. Covalent bonds between targeting ligands and, for example, lipids, may be achieved through the use of molecules that may act as spacers to increase the conformational and topographical flexibility of the ligand. Examples of such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like. In addition, in the case of targeting ligands which comprise peptide moieties, sidechain-to-sidechain crosslinking may be complemented with sidechain-to-end crosslinking and/or end-to-end crosslinking. Also, small spacer molecules, such as dimethylsuberimidate, may be used to accomplish similar objectives. The use of agents, including those used in Schiff's base-type reactions, such as gluteraldehyde, may also be employed. The Schiff's base linkages, which may be reversible linkages, can be rendered more permanent covalent linkages via the use of reductive amination procedures. This may involve, for example, chemical reducing agents, such as lithium aluminum hydride reducing agents or their milder analogs, including lithium aluminum diisobutyl hydride (DIBAL), sodium borohydride (NaBH$_4$) or sodium cyanoborohydride (NaBH$_3$CN).

The covalent linking of the targeting ligands to the stabilizing materials in the present compositions, including the prodrugs, lipids, proteins, polymers and/or surfactants, may be accomplished using synthetic organic techniques which would be readily apparent to one of ordinary skill in the art in view of the present disclosure. For example, the targeting ligands may be linked to the materials, including the lipids, via the use of well known coupling or activation agents. As known to the skilled artisan, activating agents are generally electrophilic, which can be employed to elicit the formation of a covalent bond. Exemplary activating agents which may be used include, for example, carbonyldiimidazole (CDI), dicyclohexylcarbodiimide (DCC), diisopropylcarbodiimide (DIC), methyl sulfonyl chloride, Castro's Reagent, and diphenyl phosphoryl chloride.

The covalent bonds may involve crosslinking and/or polymerization. Crosslinking preferably refers to the attachment of two chains of polymer molecules by bridges, composed of either an element, a group, or a compound, which join certain carbon atoms of the chains by covalent chemical bonds. For example, crosslinking may occur in polypeptides which are joined by the disulfide bonds of the cystine residue. Crosslinking may be achieved, for example, by (1) adding a chemical substance (crosslinking agent) and exposing the mixture to heat, or (2) subjecting a polymer to high energy radiation. A variety of crosslinking agents, or "tethers", of different lengths and/or functionalities are described, for example, in R. L. Lunbland, *Techniques in Protein Modification*, CRC Press, Inc., Ann Arbor, Mich., pp. 249–68 (1995), the disclosures of which is hereby incorporated herein by reference in its entirety. Exemplary crosslinkers include, for example, 3,3'-dithiobis (succinimidylpropionate), dimethyl suberimidate, and its variations thereof, based on hydrocarbon length, and bis-N-maleimido-1,8-octane.

In accordance with preferred embodiments, the targeting ligands may be linked or attached to the prodrugs, lipids, proteins, polymers, or surfactants or other stabilizing materials via a linking group. A variety of linking groups are available and would be apparent to one skilled in the art in view of the present disclosure. Preferably, the linking group comprises a hydrophilic polymer. Suitable hydrophilic linker polymers include, for example, polyalkyleneoxides such as, for example, polyethylene glycol (PEG) and polypropylene glycol (PPG), polyvinylpyrrolidones, polyvinylmethylethers, polyacrylamides, such as, for example, polymethacrylamides, polydimethylacrylamides and polyhydroxypropylmethacrylamides, polyhydroxyethyl acrylates, polyhydroxypropyl methacrylates, polymethyloxazolines, polyethyloxazolines, polyhydroxyethyloxazolines, polyhyhydroxypropyloxazolines, polyvinyl alcohols, polyphosphazenes, poly(hydroxyalkylcarboxylic acids), polyoxazolidines, polyaspartamide, and polymers of sialic acid (polysialics). The hydrophilic polymers are preferably selected from the group consisting of PEG, PPG, polyvinylalcohol and polyvinylpyrrolidone and copolymers thereof, with PEG and PPG polymers being more preferred and PEG polymers being even more prefered. Thus, in embodiments involving lipid compositions which comprise lipids bearing polymers including, for example, DPPE-PEG, the targeting ligand may be linked directly to the polymer which is attached to the lipid to provide, for example, a conjugate of DPPE-PEG-TL, where TL is a targeting ligand. Thus, using the example DPPE-PEG, such as, for example, DPPE-PEG5000, the aforementioned conjugate may be represented as DPPE-PEG5000-TL. The hydrophilic polymer used as a linking group is preferably a bifunctional polymer, for example, bifunctional PEG, such as diamino-PEG. In this case, one end of the PEG group is linked, for example, to a lipid compound, and is bound at the free end to the targeting ligand via an amide linkage. A hydrophilic polymer, for example, PEG, substituted with a terminal carboxylate group on one end and a terminal amino group on the other end, may also be used. These latter bifunctional hydrophilic polymer may be preferred since they possess various similarities to amino acids.

Standard peptide methodology may be used to link the targeting ligand to the lipid when utilizing linker groups having two unique terminal functional groups. Bifunctional hydrophilic polymers, and especially bifunctional PEGs, may be synthesized using standard organic synthetic methodologies. In addition, many of these materials are available commercially, such as, for example, α-amino-ω-carboxy-PEG which is commercially available from Shearwater Polymers (Huntsville, Ala.). An advantage of using a PEG material as the linking group is that the size of the PEG can be varied such that the number of monomeric subunits of ethylene glycol may be as few as, for example, about 5, or as many as, for example, about 500 or even greater. Accordingly, the "tether" or length of the linkage may be varied, as desired. This may be important depending, for example, on the particular targeting ligand employed. For example, a targeting ligand which comprises a large protein molecule may require a short tether, such that it will simulate a membrane bound protein. A short tether would also allow for a vesicle to maintain a close proximity to the cell. This can be used advantageously in connection with vesicles which also comprise a bioactive agent, including a prodrug, in that the concentration of bioactive agent or prodrug which is delivered to the cell may be advantageously increased. Another suitable linking group which may provide a short tether is glyceraldehyde. Glyceraldehyde may be bound, for example, to DPPE via a Schiff's base reaction. Subsequent Amadori rearrangement can provide a substantially short linking group. The β carbonyl of the Schiff's base may then react with a lysine or arginine of the targeting protein or peptide to form the targeted lipid.

More specifically, the compounds employed in the present stabilizing materials, including prodrugs, lipids, proteins, polymers and/or surfactants, may contain various functional groups, such as, for example, hydroxy, thio and amine groups, which can react with a carboxylic acid or carboxylic acid derivative of the hydrophilic polymeric linker using suitable coupling conditions which would be apparent to one of ordinary skill in the art in view of the present disclosure. After the carboxylic acid group (or derivative thereof) reacts with the functional group, for example, hydroxy, thio or amine group to form an ester, thioester or amide group, any protected functional group may be deprotected utilizing procedures which would be well known to those skilled in the art. The term protecting group refers to any moiety which may be used to block the reaction of a functional group and which may be removed, as desired, to afford the unprotected functional group. Any of a variety of protecting groups may be employed and these will vary depending, for example, as to whether the group to be protected is an amine, hydroxyl or carboxyl moiety. If the functional group is a hydroxyl group, suitable protecting groups include, for example, certain ethers, esters and carbonates. Such protecting groups are described, for example, in Greene, T W and Wuts, PGM "Protective Groups in Organic Synthesis" John Wiley, New York, 2nd Edition (1991), the disclosure of which is hereby incorporated herein by reference in its entirety. Exemplary protecting groups for amine groups include, for example, t-butyloxycarbonyl (Boc), allyloxycarbonyl (Alloc), benzyloxycarbonyl(Cbz), o-nitrobenzyloxycarbonyl and and trifluoroacetate (TFA).

Amine groups which may be present, for example, on a backbone of a polymer which is included in the vesicles, may be coupled to amine groups on a hydrophilic linking polymer by forming a Schiff's base, for example, by using coupling agents, such as glutaraldehyde. An example of this coupling is described by Allcock et al., *Macromolecules*, 19(6):1502–1508 (1986), the disclosure of which is hereby incorporated herein by reference in its entirety. If, for example, vesicles are formulated from polylysine, free amino groups may be exposed on the surface of the vesicles, and these free amine groups may be activated as described above. The activated amine groups can be used, in turn, to couple to a functionalized hydrophilic polymer, such as, for example, α-amino-ω-hydroxy-PEG in which the ω-hydroxy group has been protected with a carbonate group. After the reaction is completed, the carbonate group can be cleaved, thereby enabling the terminal hydroxy group to be activated for reaction to a suitable targeting ligand. In certain embodiments, the surface of a vesicle may be activated, for example, by displacing chlorine atoms in chlorine-containing phosphazene residues, such as polydichlorophosphazene. Subsequent addition of a targeting ligand and quenching of the remaining chloride groups with water or aqueous methanol will yield the coupled product.

In addition, poly(diphenoxyphosphazene) can be synthesized (Allcock et al., *Macromolecules*, 19(6):1502–1508 (1986)) and immobilized, for example, on DPPE, followed by nitration of the phenoxy moieties by the addition of a mixture of nitric acid and acetic anhydride. The subsequent nitro groups may then be activated, for example, by (1) treatment with cyanogen bromide in 0.1 M phosphate buffer (pH 11), followed by addition of a targeting ligand containing a free amino moiety to generate a coupled urea analog, (2) formation of a diazonium salt using sodium nitrite/HCl, followed by addition of the targeting ligand to form a coupled ligand, and/or (3) the use of a dialdehyde, for example, glutaraldehyde as described above, to form a Schiff's base. After linking the DPPE to the hydrophilic polymer and the targeting ligand, the vesicles may be formulated utilizing the procedures described herein.

Aldehyde groups on polymers can be coupled with amines as described above by forming a Schiff's base. An example of this coupling procedure is described in Allcock and Austin, *Macromolecules*, 14:1616 (1981), the disclosure of which is hereby incorporated herein by reference in its entirety.

In the above procedures, the polymer or terminus of the lipid, for example, phosphatidylglycerol or phosphatidylethanolamine, is preferably activated and coupled to the hydrophilic polymeric linker, the terminus of which has been blocked in a suitable manner. As an example of this strategy, α-amino-ω-carboxy-PEG4000 having a t-Boc protected terminal amino group and a free carboxylate end, may be activated with 1,1'-carbonyldiimidazole in the presence of hydroxybenzotriazole in N-methylpyrollidone. After the addition of phosphatidylethanolamine, the t-Boc group may be removed by using trifluoroacetic acid (TFA), leaving the free amine. The amine may then be reacted with a targeting ligand which may comprise, for example, a peptide, protein, alkaloid, or other moiety, by similar activation of the ligand, to provide the lipid-linker-targeting ligand conjugate. Other strategies, in addition to those exemplified above, may be utilized to prepare the lipidlinker-targeting ligand conjugates. Generally speaking, these methods employ synthetic strategies which are generally known to those skilled in the art of synthetic organic chemistry.

As known to one of ordinary skill in the art, immunoglobulins typically comprise a flexible region which is identified as the "hinge" region. See, e.g., "Concise Encyclopedia of Biochemistry", Second Edition, Walter de Gruyter & Co., pp. 282–283 (1988). Fab' fragments can be linked to the lipids, polymers, proteins and/or vesicles using the well-defined sites of the thiols of the hinge region. This is a preferred region for coupling Fab' fragments as the potential binding site is remote from the antigen-recognition site. Generally speaking, it may be difficult to utilize the thiols of the hinge group unless they are adequately prepared. In particular, as outlined by Shahinian and Salvias (*Biochimica et Biophysica Acta*, 1239:157–167 (1995)) it may be important to reduce the thiol groups so that they are available for coupling, for example, to maleimide derivatized linking groups. Examples of reducing agents commonly used are ethanedithiol, mercaptoethanol, mercaptoethylamine or the more commonly used dithiothreitol, commonly referred to as Cleland's reagent. However, it should be noted that care should be exercised when utilizing certain reducing agents, such as dithiothreitol, as overreduction may result. Discriminating use of reducing agents may be necessary in connection with proteins whose activity or binding capacity may be compromised due to overreduction and subsequent denaturation or conformational change. See, e.g., Shahinian, et al, *Biochim. Biophys. Acta*, 1239:157–167 (1995), the disclosure of which is hereby incorporated herein by reference in its entirety.

F(ab')$_2$ antibody fragments may be prepared by incubating the antibodies with pepsin (60 μg/ml) in 0.1 M sodium acetate (pH 4.2) for 4 h at 37° C. Digestion may be terminated by adding 2 M Tris (pH 8.8) to a final concentration of 80 mM. The F(ab')$_2$ fragments may then be obtained by centrifugation (10,000×g. 30 min. 4° C.). The supernatant may then be dialyzed at 4° C. against 150 mM NaCl, 20 mM phosphate at pH 7.0. This then may be chromatographed on a column of Protein A-Sepharose CL-4B to remove any undigested IgG. The Fab' fragments may then be prepared by extensively degassing the solutions and purging with nitrogen prior to use. The Fab')$_2$ fragments may be provided at a concentration of 5 mg/ml and reduced under argon in 30 mM cysteine. Alternatively, cysteamine may be employed. 100 mM Tris, pH 7.6 may be used as a buffer for 15 min at 37° C. The solutions may then be diluted 2-fold with an equal volume of the appropriate experimental buffer and spun through a 0.4 ml spin column of Bio-Gel P-6DG. The resulting Fab' fragments may be more efficient in their coupling to maleimide linkers. Note also that the same procedure may be employed with other macromolecules containing cysteine residues for coupling, for example, to the maleimide spacers. Also, peptides may be utilized provided that they contain a cysteine residue. If the peptides have not been made fresh and there is a possibility of oxidation of cysteine residues within the peptide structure, it may be necessary to regenerate the thiol group using the approach outlined above.

Additional linkers would include other derivatives of lipids useful for coupling to a bifunctional spacer. For example, phosphatidylethanolamine (PE) may be coupled to a bifunctional agent. For example N-succinimidyl 4-(p-maleimido-phenyl)butyrate (SMPB) and N-succinimidyl 3-(2-pyridyldithiol) propionate (SPDP), N-succinimidyl trans-4-(N-maleimidylmethyl)cyclohexane-1-carboxylate (SMCC), and N-succinimidyl 3-maleimidylbenzoate (SMB) may be used among others, to produce, for example the functionalized lipids MPB-PE and PDP-PE.

The free end of the hydrophilic spacer, such as polyethylene glycol ethylamine, which contains a reactive group, such as an amine or hydroxyl group, could be used to bind a cofactor or other targeting ligand. For example, polyethylene glycol ethylamine may be reacted with N-succinimidylbiotin or p-nitrophenylbiotin to introduce onto the spacer a useful coupling group. For example, biotin may be coupled to the spacer and this will readily bind non-covalently proteins. As an example, MPB-PEG-DPPE may be synthesized as follows. DPPE-PEG with a free amino group at the terminus of the PEG will be provided as described previously. Synthesis of the SMPB:PEG-DPPE may then be carried out with 1 equivalent of triethylamine in chloroform at a molar ratio of 1:5 SMPB:DPPE-PEG. After 3 hours, the reaction mixture will be evaporated to dryness under argon. Excess unreacted SMPB and major by products will be removed by preparative thin layer chromatography (TLC, silica gel developed with 50% acetone in chloroform). The upper portion of the lipid band can be extracted from the silica with about 20–30% methanol in chloroform (V:V) resulting in the isolation of pure intact MPB-Peg-DPPE. Streptavidin may then be coupled to proteins so that the proteins in turn may then be coupled to the MPB-PEG-DPPE. Briefly SPDP would be incubated with streptavidin at room temperature for 30 minutes and chromatography employed to remove unreacted SPDP. Dithiothreitol (DTT) was added to the reaction mixture and 10 minutes later 2-thiopyridone at a concentration of 343 nM. The remainder of the reaction mixture is reduced with DTT (25 mM for 10 min.). The thiolated product is isolated by gel exclusion. The resulting streptavidin labeled proteins may then be used to bind to the biotinylated spacers affixed to the lipid moieties.

In preferred embodiments of the present invention, the targeted compounds, namely, targeted stabilizing materials, including prodrugs, lipids, proteins, polymers and surfactants, are incorporated in compositions which are used to form targeted emulsions and/or targeted vesicles, including, for example, targeted emulsions, targeted micelles, targeted liposomes, targeted albumin coated microspheres, and/or targeted polymer coated microspheres. The targeting ligand which is attached to the compounds from which the vesicles are prepared may be directed, for example, outwardly from the surface of the vesicle. Thus, there is provided a targeted vesicle which can be used to target receptors and tissues.

In certain embodiments, the targeting ligands may be incorporated in the present stabilizing materials via non-covalent associations. As known to those skilled in the art, non-covalent association is generally a function of a variety of factors, including, for example, the polarity of the involved molecules, the charge (positive or negative), if any, of the involved molecules, the extent of hydrogen bonding through the molecular network, and the like. Non-covalent bonds are preferably selected from the group consisting of ionic interaction, dipole-dipole interaction, hydrogen bonds, hydrophilic interactions, van der Waal's forces, and any combinations thereof. Non-covalent interactions may be employed to bind the targeting ligand to the lipid, or directly to the surface of a vesicle. For example, the amino acid sequence Gly-Gly-His may be bound to the surface of a vesicle, preferably by a linker, such as PEG, and copper, iron or vanadyl ion may then be added. Proteins, such as antibodies which contain histidine residues, may then bind to the vesicle via an ionic bridge with the copper ion, as described in U.S. Pat. No. 5,466,467, the disclosure of which is hereby incorporated herein by reference in its entirety. An example of hydrogen bonding involves cardiolipin lipids which can be incorporated into the lipid compositions.

In preferred embodiments of the present invention, which may involve vesicles, changes, for example, in pH and/or temperature in vivo, may be employed to promote a change in location in the targeting ligands, for example, from a location within the vesicle, to a location external to the outer wall of the vesicle. This may promote binding of the targeting ligands to targeting sites, for example, receptors, such as lymphocytes, and tissues, including myocardial, endothelial and epithelial cells, since the targeting ligand has a greater likelihood of exposure to such targeting sites. In addition, high energy ultrasound can be used to promote rupturing of the vesicles. This can also expose the targeting ligand to the desired binding site.

As an example, a targeting ligand incorporated into the compositions of the present invention may be of the formula:

wherein:

L is a lipid, protein, polymer, carbohydrate, surfactant or the like;

P is a hydrophilic polymer; and

T is a targeting ligand.

In a preferred embodiment, L is a lipid selected from the group consisting of lecithins, phosphatidylcholines, phosphatidylserines, phosphatidylinositols, cardiolipins, cholesterols, cholesterolamines, lysophosphatides, erythrosphingosines, sphingomyelins, ceramides, cerebrosides, saturated phospholipids, unsaturated phospholipids, and krill phospholipids. More preferably, L is a lipid is selected from the group consisting of lecithins, phosphatidylcholines, phosphatidylserines and phosphatidylinositols. In other preferred embodiments, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidyl-cholines, lysophosphatidylglycerols, 1,2-diacyl-sn-glycerols, 1,2-diacyl-ethylene glycols, N-(n-caproylamine)-1,2-diacyl-sn-glycero-3-phosphoethanolamines, N-dodecanylamine-1,2-diacyl-sn-glycero-3-phosphoethanol-amines, N-succinyl-1,2-diacyl-sn-glycero-3-phosphoethanolamines, N-glutaryl-1,2-diacyl-sn-glycero-3-phosphoethanolamines and N-dodecanyl-1,2-diacyl-sn-glycero-3-phosphoethanolamines. More preferably, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidylcholines, lysophosphatidyl-glycerols and 1,2-diacyl-sn-glycerols.

In other preferred embodiments, L is a protein which comprises albumin.

In still other preferred embodiments, L is a polymer which comprises synthetic polymers or copolymers prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, E-caprolactone, acrolein, cyanoacrylate, bisphenol A, epichlorhydrin, hydroxyalkylacrylates, siloxane, dimethylsiloxane, ethylene oxide, propylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-aminobenzylstyrene, sodium styrene sulfonate, sodium 2-sulfoxyethylmeth-acrylate, vinyl pyridine, aminoethyl methacrylates, 2-methacryloyloxy-trimethylammonium chloride and polyphosphazene. Also preferred are compounds where L is a polymer which comprises synthetic polymers or copolymers selected from the group consisting of polyacrylic acid, polyethyleneimine, polymethacrylic acid, polymethylmeth-acrylate, polysiloxane, polydimethylsiloxane, polylactic acid, poly(ε-caprolactone), epoxy resin, poly(ethylene oxide), poly(propylene oxide), poly(ethylene glycol), polyamide, polyvinylidene-polyacrylonitrile, polyvinylidene-polyacrylonitrile-polymethylmeth-acrylate and polystyrene-polyacrylonitrile. Preferred among these polymers is polyvinylidene-polyacrylonitrile copolymer.

In other preferred embodiments, L is a surfactant, preferably a fluorosurfactant, and more preferably a fluorosurfactant having polyethylene glycol attached thereto.

In the above compounds, P is a hydrophilic polymer. Preferably, P is a hydrophilic polymer selected from the group consisting of polyalkyleneoxides, polyvinyl alcohol, polyvinylpyrrolidones, polyacrylamides, polymethacrylamides, polyphosphazenes, phosphazene, poly(hydroxyalkylcarboxylic acids) and polyoxazolidines. More preferably, P is a polyalkyleneoxide polymer, with polyethylene glycol and polypropylene glycol being even more preferred and polyethylene glycol being particularly preferred.

In the above formula, T is a targeting ligand. Preferably, T is a targeting ligand which targets lymphocytes. Also in preferred embodiments, T is a targeting ligand selected from the group consisting of proteins, peptides, saccharides, steroids, steroid analogs, bioactive agents and genetic material, with proteins, peptides and saccharides being more preferred. Most preferred, T is a targeting ligand which targets T-cell receptors, B-cell receptors or IL-2 receptors.

In the case of targeting ligands which comprise saccharide groups, suitable saccharide moieties include, for example, monosaccharides, disaccharides and polysaccharides. Exemplary monosaccharides may have six carbon atoms and these saccharides include allose, altrose, glucose, dextrose, mannose, gulose, idose, galactose, talose, fructose, psicose, verbose and tagatose. Five carbon saccharides include ribose, arabinose, xylose, lyxose, ribulose and xylulose. Four carbon saccharides include erythrose, threose and erythrulose. Disaccharides include sucrose, lactose, maltose, isomaltose and cellobiose. Saccharide bearing targeting lipids may be synthesized through a multistep organic synthesis approach, as described more fully hereinafter. For example, lipids bearing targeting glucose moieties may be prepared by reacting, for example, α-glucopyranosyl bromide tetrabenzyl with ω-trifluoroacetylaminopoly-ethyleneglycol to obtain ω-glucopyranosyl tetrabenzyl-ω'-trifluoroacetylaminopoly-ethyleneglycol. This may then be hydrolyzed in a sodium carbonate or potassium carbonate solution and then hydrogenated to obtain ω-glucopyranpsyl-ω'amino-polyethyleneglycol. Aminoglyco-pyranosyl terminated polyethyleneglycol may then react with N-DPGS-succinimide to form the lipid bearing saccharide DPGS-NH-PEG-Glucose. In certain embodiments, the targeting ligands target cancer cells or tumor cells.

In another embodiment, the targeting ligand incorporated into the compositions of the present invention may be of the following formula, which falls within the scope of the formula L—P—T above:

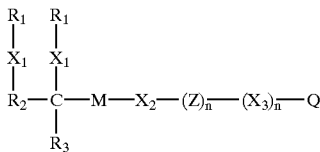

wherein:
each $X_1$ is independently —O—, —S—, —SO—, —SO2—, —NR$_4$—, —X$_4$—C(=X$_5$)—, —C(=X$_5$)—X$_4$— or —C(=X$_5$)—;
each of $X_2$ and $X_3$ is independently a direct bond, —R$_5$—$_4$—C(=X$_5$)—, —R$_5$—C(=X)—X$_4$—, —X$_4$—C(=X$_5$)—R$_5$—, —C(—X$_5$)—X$_4$—R$_5$—, —X$_4$—R$_5$—C(=X$_{R5}$)—X$_4$—C(=X$_5$)—R$_5$—C(=X$_5$)—X$_4$— or —R$_5$—C(=X$_5$)—X$_4$—R$_5$—X$_4$—C(=X$_5$)—;
each $X_4$ is independently —O—, —NR$_4$— or —S—;
each $X_5$ is independently 0 or S;
M is —R$_5$—X$_4$—C(=X$_5$)—, —R$_5$—C(=X$_5$)—X$_4$—, —R$_5$—X$_4$—(YX$_5$)P(=X$_5$)—X$_4$—X$_4$—(YX$_5$)P(=X$_5$)—X$_4$—R$_5$—;
each n is, independently, 0 or 1;
Y is hydrogen or a pharmaceutically acceptable counter ion;
Z is a hydrophilic polymer;
Q is a targeting ligand or a precursor to a targeting ligand;
each $R_1$ is independently an alkyl group of 1 to about 50 carbons that may optionally be substituted with one or more halogen atoms;
each $R_2$ is independently an alkylene group of 1 to about 30 carbons that may optionally be substituted with one or more halogen atoms;
each of $R_3$ and $R_4$ is independently hydrogen or alkyl of 1 to about 10 carbons; and
each $R_5$ is independently a direct bond or alkylene of 1 to about 30 carbons.

In the above formula, it is intended that when any symbol appears more than once in a particular formula or substituent, its meaning in each instance is independent of the other. Also in the above formula, it is intended that when each of two or more adjacent symbols is defined as being a "direct bond" to provide multiple, adjacent direct bonds, the multiple and adjacent direct bonds devolve into a single direct bond.

In preferred embodiments, each $X_1$ is independently —X$_4$—C(=X$_5$)—, —C(=X$_5$)—X$_4$— or —C(=X$_5$)—. More preferably, each $X_1$ is independently —X$_4$—C(=X$_5$)— or —C(—X$_5$)—X$_4$—. Even more preferably, $X_1$ is —C(=X$_5$)—X$_4$—, for example, —C(=O)—O—.

In preferred embodiments, each of $X_2$ and $X_3$ is independently a direct bond, —R$_5$—X$_4$—C(=X$_5$)—, —R$_5$—C(=X$_5$)—X$_4$, —X$_4$—C(=X$_5$)—R$_5$—, —C(=X$_5$)—X$_4$—$x_4$—R$_5$—C(=X$_5$)—X$_4$— or —R$_5$—X$_4$—C(=X$_5$)— R$_5$—C(=X$_5$)—X$_4$—. More preferably, $X_2$ is —CH$_2$X$_2$—C(=O)—NH— or —CH$_2$CH$_2$NH—C(=O)—CH$_2$CH$_2$—C(=O)—NH— and $X_3$ is a direct bond, —C(=O)—NH—, —NH—C(=O)—, —NH—C(=O)—CH$_2$, —NHCH$_2$—C(=O)—NH— or —NH—C(=O)—CH$_2$CH$_2$.

Preferably, each $X_4$ is independently —O— or —NR$_4$—. Preferably, $X_5$ is O.

In certain preferred embodiments, M is —R$_5$—X$_4$—C(=X$_5$)— or —R$_5$—X$_4$—(YX$_5$)P(=X$_5$)—X$_4$—, with M more preferably being —CH$_2$O—C(=O) or —CH$_2$O—(HO)P(=O)—O—. In certain other preferred embodiments, M is —R$_5$—X$_4$—C(=X$_5$)— or —R$_5$—C(=X$_5$)—X$_4$—. In yet other preferred embodiments, M is —R$_5$—X$_4$—(YX$_5$)P(=X$_5$)—X$_4$— or —X$_4$—(YX$_5$)P(=X$_5$)—X$_4$—R$_5$—. wherein at least one of $X_4$ or $X_5$ is S.

In the above formula, Z is a hydrophilic polymer. Preferably, Z is selected from the group consisting of polyalkyleneoxides, polyvinyl alcohol, polyvinylpyrrolidones, polyacrylamides, polymethacrylamides, polyphosphazenes, poly (hydroxyalkylcarboxylic acids) and polyoxazolidines. More preferably, Z comprises a polyalkyleneoxide. Even more preferably, Z is a polyalkyleneoxide selected from the group consisting of polyethylene glycol and polypropylene glycol, with polyethylene glycol being still more preferred. In certain other preferred embodiments, Z is a hydrophilic polymer other than polyalkyleneoxides, including polyethylene glycol and polypropylene glycol. The molecular weight of Z may vary, depending, for example, on the particular end-use of the compounds. Preferably, Z is a polymer having a molecular weight which ranges from about 100 to about 10,000, and all combinations and subcombinations of ranges therein. More preferably, Z is a polymer having a molecular weight of from about 1,000 to about 5,000. Also preferred are polymers which exhibit polydispersities ranging from greater than about 1 to about 3, and all combinations and subcombinations of ranges therein. More preferably, Z is a polymer having a polydispersity of from greater than about 1 to about 2, with polydispersities of from greater than about 1 to about 1.5 being even more preferred, and polydispersities of from greater than about 1 to about 1.2 being still more preferred.

In the above formula, Q is a targeting ligand or a precursor thereto. In embodiments where Q is a targeting ligand, Q preferably targets lymphocytes. In addition, in embodiments where Q is a targeting ligand, Q is preferably selected from the group consisting of proteins, peptides, saccharides, steroids, steroid analogs, bioactive agents, and genetic material. In these latter embodiments, Q is preferably selected from the group consisting of proteins, peptides and saccharides. Most preferred, Q targets T-cell receptors, B-cell receptors or IL-2 receptors.

In the above formula, each $R_1$ is independently alkyl which ranges from 1 to about 50 carbons, and all combinations and subcombinations of ranges therein, or alkenyl of from about 2 to about 50 carbons, and all combinations and subcombinations of ranges therein. Preferably, each $R_1$ is independently alkyl of greater than 1 to about 40 carbons. More preferably, each $R_1$ is independently alkyl of about 5 to about 30 carbons. Even more preferably, each $R_1$ is independently alkyl of about 10 to about 20 carbons, with alkyl of about 15 carbons being still more preferred. In certain preferred embodiments, $R_1$ is a shorter chain alkyl of from 1 to about 20 carbons. In certain other preferred embodiments, $R_1$ is a longer chain alkyl of from about 20 to about 50 carbons, or about 30 to about 50 carbons. In other preferred embodiments, the alkyl group in $R_1$ may be substituted with one or more fluorine atoms, and may be perfluorinated.

In the above formula, each $R_2$ is independently alkylene which ranges from 1 to about 30 carbons, and all combinations and subcombinations of ranges therein. Preferably, each $R_2$ is independently alkylene of 1 to about 20 carbons. More preferably, each $R_2$ is independently alkylene of 1 to about 10 carbons. Even more preferably, each $R_2$ is independently alkylene of 1 to about 5 carbons, with methylene being especially preferred. In other preferred embodiments, the alkylene group in $R_2$ may be substituted with one or more fluorine atoms, and may be perfluorinated.

In the above formula, each of $R_3$ and $R_4$ is independently hydrogen or alkyl which ranges from 1 to about 10 carbons, and all combinations and subcombinations of ranges therein. Preferably, each of $R_3$ and $R_4$ is hydrogen or alkyl of 1 to about 5 carbons. More preferably, each of $R_3$ and $R_4$ is hydrogen.

In the above formula, each $R_5$ is independently a direct bond or alkylene which ranges from 1 to about 30 carbons, and all combinations and subcombinations of ranges therein. Preferably, each $R_5$ is independently a direct bond or alkylene of 1 to about 20 carbons. More preferably, each $R_5$ is independently a direct bond or alkylene of 1 to about 10 carbons. Even more preferably, each $R_5$ is independently a direct bond or alkylene of 1 to about 5 carbons. Still more preferably, each $R_5$ is a direct bond or —$(CH_2)_x$—, where x is 1 or 2.

The foregoing preferred embodiments of the compounds of the present invention are preferred for various reasons, including ease of synthesis, diagnostic efficacy, enhanced biocompatibility, and/or improved targeting efficacy.

Contrast Agents

The stabilizing materials of the present invention are particularly useful in connection with ultrasound (US), including diagnostic and therapeutic ultrasound. The stabilizing materials and/or vesicles of the present invention may be used alone, or may be used in combination with various contrast agents, including conventional contrast agents, which may serve to increase their effectiveness as contrast agents for diagnostic imaging.

The present stabilizing materials may also be employed, if desired, in connection with computed tomography (CT) imaging, magnetic resonance imaging (MRI), optical imaging, or other of the various forms of diagnostic imaging that are well known to those skilled in the art. For optical imaging, gas bubbles improve visualization of, for example, blood vessels on the imaging data set. With CT, for example, if a high enough concentration of the present contrast media, and especially gas filled vesicles, is delivered to the region of interest, for example, a blood clot, the clot can be detected on the CT images by virtue of a decrease in the overall density of the clot. In general, a concentration of about 1/10 of 1% of gas filled vesicles or higher (on a volume basis), may be needed to delivered to the region of interest, including the aforementioned blood clot, to be detected by CT.

Examples of suitable contrast agents for use in combination with the present stabilizing materials include, for example, stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. Preferable transition, lanthanide and actinide elements include, for example, Gd(III), Mn(II), Cu(II), Cr(III), Fe(II), Fe(II), Co(II), Er(II), Ni(II), Eu(III) and Dy(III). More preferably, the elements may be Gd(III), Mn(II), Cu(II), Fe(II), Fe(III), Eu(III) and Dy(III), most preferably Mn(II) and Gd(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylene-diaminetetraacetic acid (EDTA), 1,4,7,10-tetraazacyclododecane-N,N',N',N'''-tetraacetic acid (DOTA), 1,4,7,10-tetraazacyclododecane-N,N',N''-triacetic acid (DOTA), 3,6,9-triaza-12-oxa-3,6,9-tricarboxymethylene-10-carboxy-13-phenyl-tridecanoic acid (B-19036), hydroxybenzyl-ethylenediamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,1-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)ethylenediamine-N,N'-diacetate (EDTA-DDP); N,N'-bis-(carboxy-octadecylamido-methyl-N-2,3-dihydroxypropyl)ethylenediamine-N,N'-diacetate (EDTA-ODP); and N,N'-Bis(carboxy-laurylamidomethyl-N-2,3-dihydroxypropyl)ethylenediamine-N,N'-diacetate (EDTA-LDP); including those described in U.S. Pat. No. 5,312,617, the disclosure of which is hereby incorporated herein by reference in its entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred. Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, more preferably Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular theory of operation, it is contemplated that since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

Exemplary superparamagnetic contrast agents suitable for use in the compositions of the present invention include metal oxides and sulfides which experience a magnetic domain, ferro- or ferrimagnetic compounds, such as pure iron. magnetic iron oxide, such as magnetite, $\gamma$—$Fe_2O_3$, $Fe_3O_4$, manganese ferrite, cobalt ferrite and nickel ferrite. Paramagnetic gases can also be employed in the present compositions, such as oxygen 17 gas ($^{17}O_2$). In addition, hyperpolarized xenon, neon, or helium gas may also be employed. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the lipid and/or vesicle compositions. In the case of vesicle compositions, the aforementioned contrast agents may be entrapped within the internal void thereof, administered as a solution with the vesicles, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

The stabilizing materials and/or vesicles of the present invention, and especially the vesicles, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, for example, particles having diameters of about 100 nm, have much higher R2 relaxivities as compared to R1 relaxivities. The smaller particles, for example, particles having diameters of about 10 to about 15 nm, have somewhat lower R2 relaxivities, but much more balanced R1 and R2 values. Much smaller particles, for example, monocrystalline iron oxide particles having diameters of about 3 to about 5 nm, have lower R2 relaxivities, but probably the most balanced R1 and R2 relaxation rates. Ferritin can also be formulated to encapsulate a core of very high relaxation rate superparamagnetic iron. It has been discovered that the lipid and/or vesicle compositions, especially vesicle compositions, including gas filled vesicles, can increase the efficacy and safety of these conventional iron oxide based MRI contrast agents.

The iron oxides may simply be incorporated into the stabilizing materials and/or vesicles. Preferably, in the case of vesicles formulated from lipids, the iron oxides may be incorporated into the walls of the vesicles, for example, by being adsorbed onto the surfaces of the vesicles, or entrapped within the interior of the vesicles as described in U.S. Pat. No. 5,088,499, the disclosure of which is hereby incorporated herein by reference in its entirety.

Without being bound to any particular theory or theories of operation, it is believed that the vesicles of the present invention increase the efficacy of the superparamagnetic contrast agents by several mechanisms. First, it is believed that the vesicles function to increase the apparent magnetic concentration of the iron oxide particles. Also, it is believed that the vesicles increase the apparent rotational correlation time of the MRI contrast agents, including paramagnetic and superparamagnetic agents, so that relaxation rates are increased. In addition, the vesicles appear to increase the apparent magnetic domain of the contrast medium according to the manner described hereinafter.

Certain of the vesicles of the present invention, and especially vesicles formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, it should be noted that the contrast provided by these agents is dependent on particle size. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion:

$$1/T_1M=(2/15)S(S+1)\gamma^2g^2\beta/r^6[3\tau_c/(1+\omega_1^2\tau_c^2)+7\tau_c/(1+\omega_s^2\tau_c^2)]+(2/3)S(S+1) A^2/h^2[\tau_e/(1+\omega_s2\tau_e^2)]$$

and $$1/T_2M=(1/15)S(S+1)\gamma^2g^2\beta^2/r^6[4\tau_c+3\tau c/(1+\omega_1^2\tau_c^2)+13\tau_c/(1+w_s^2\tau_c^2)]+(1/3)S(S+1)A^2/h^2[\tau_e/(1+\omega_s2\tau_e^2)]$$

where: S is the electron spin quantum number; g is the electronic g factor; $\beta$ is the Bohr magneton; $\omega_1$ and $\omega_s$ (657 $w_1$) is the Larmor angular precession frequencies for the nuclear spins and electron spins; r is the ion-nucleus distance; A is the hyperfine coupling constant; $\tau_c$ and $\tau_e$ are the correlation times for the dipolar and scalar interactions, respectively; and h is Planck's constant. See, e.g., Solomon, I., *Phys. Rev.* Vol. 99, p. 559 (1955) and Bloembergen, N. *J. Chem. Phys.* Vol. 27, pp. 572, 595 (1957), the disclosures of each of which are hereby incorporated herein by reference in their entirety.

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, it is believed that the total size of the particle is not as important as the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence for a paramagnetic dipole-dipole interaction. Interpreted literally, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. It has not been possible to achieve this heretofore and it is believed that the benefits have been unrecognized heretofore also. By coating the inner or outer surfaces of the vesicles with the contrast agents, even though the individual contrast agents, for example, iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible vesicles described above, it may be desirable, in certain circumstances, to formulate vesicles from substantially impermeable polymeric materials including, for example, polymethyl methacrylate. This would generally result in the formation of vesicles which may be substantially impermeable and relatively inelastic and brittle. In embodiments involving diagnostic imaging, for example, ultrasound, contrast media which comprise such brittle vesicles would generally not provide the desirable reflectivity that the flexible vesicles may provide. However, by increasing the power output on ultrasound, the brittle microspheres can be made to rupture, thereby causing acoustic emissions which can be detected by an ultrasound transducer.

Nuclear Medicine Imaging (NMI) may also be used in connection with the diagnostic and therapeutic method aspects of the present invention. For example, NMI may be used to detect radioactive gases, such as $Xe^{33}$, which may be incorporated in the present compositions in addition to, or instead of, the gases discussed above. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as technetium$^{99m}$ or indium$^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

For optical imaging, optically active gases, such as argon or neon, may be incorporated in the present compositions. In addition, optically active materials, for example, fluorescent materials, including porphyrin derivatives, may also be used. Elastography is an imaging technique which generally employs much lower frequency sound, for example, about 60 KHz, as compared to ultrasound which can involve frequencies of over 1 MHz. In elastography, the sound energy is generally applied to the tissue and the elasticity of the tissue may then be determined. In connection with preferred embodiments of the invention, which involve highly elastic vesicles, the deposition of such vesicles onto, for example, a clot, increases the local elasticity of the tissue and/or the space surrounding the clot. This increased elasticity may then be detected with elastography. If desired, elastography can be used in conjunction with other imaging techniques, such as MRI and ultrasound.

Methods of Preparation

The stabilizing materials and/or vesicles of the present invention may be prepared using any of a variety of suitable methods. These are described below separately for the embodiments involving stabilizing materials and a gas, including gas filled vesicles, and embodiments involving stabilizing materials and a gaseous precursor, including gaseous precursor filled vesicles, although stabilizing materials comprising both a gas and a gaseous precursor are a part of the present invention. A targeting ligand may be attached to the gas and/or gaseous precursor filled vesicle by bonding to one or more of the materials employed in the compositions from which they are made, including the steroid prodrugs, lipids, proteins, polymers, surfactants and/or auxiliary stabilizing materials, such as surfactants or polymers.

A wide variety of methods are available for the preparation of the stabilizing materials, including vesicles, such as micelles and/or liposomes. Included among these methods are, for example, shaking, drying, gas-installation, spray drying, and the like. Suitable methods for preparing vesicle compositions are described, for example, in U.S. Pat. No. 5,469,854, the disclosure of which is hereby incorporated herein by reference in its entirety. The vesicles are preferably prepared from lipids which remain in the gel state.

Micelles may be prepared using any one of a variety of conventional micellar preparatory methods which will be apparent to those skilled in the art. These methods typically involve suspension of the stabilizing material, such as a lipid compound, in an organic solvent, evaporation of the solvent, resuspension in an aqueous medium, sonication and centrifugation. The foregoing methods, as well as others, are discussed, for example, in Canfield et al., *Methods in Enzymology*, 189:418–422 (1990); El-Gorab et al, *Biochem. Biophys. Acta*, 306:58–66 (1973); *Colloidal Surfactant*, Shinoda, K., Nakagana, Tamamushi and Isejura, Academic Press, NY (1963) (especially "The Formation of Micelles", Shinoda, Chapter 1, pp. 1–88); *Catalysis in Micellar and Macromolecular Systems*, Fendler and Fendler, Academic Press, NY (1975). The disclosures of each of the foregoing publications are hereby incorporated herein by reference in their entirety.

In liposomes, the lipid compound(s) may be in the form of a monolayer or bilayer, and the monolayer or bilayer lipids may be used to form one or more monolayers or bilayers. In the case of more than one monolayer or bilayer, the monolayers or bilayers are generally concentric. Thus, lipids may be used to form unilamellar liposomes (comprised of one monolayer or bilayer), oligolamellar liposomes (comprised of two or three monolayers or bilayers) or multilamellar liposomes (comprised of more than three monolayers or bilayers).

A wide variety of methods are available in connection with the preparation of vesicles, including liposomes. Accordingly, liposomes may be prepared using any one of a variety of conventional liposomal preparatory techniques which will be apparent to those skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of lipids*, 53:37–46 (1990), the disclosure of which is hereby incorporated herein by reference in its entirety. Suitable freeze-thaw techniques are described, for example, in International Application Serial No. PCT/US89/05040, filed Nov. 8, 1989, the disclosure of which is hereby incorporated herein by reference in its entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug™ (Crescent Dental, Lyons, Ill.), a Mixomat, sold by Degussa A G, Frankfurt, Germany, a Capmix, sold by Espe Fabrik Pharmazeutischer Praeparate GMBH & Co., Seefeld, Oberay Germany, a Silamat Plus, sold by Vivadent, Lechtenstein, or a Vibros, sold by Quayle Dental, Sussex, England. Conventional microemulsification equipment, such as a Microfluidizer™ (Microfluidics, Woburn, Mass.) may also be used.

Spray drying may be employed to prepare gas filled vesicles. Utilizing this procedure, the stabilizing materials, such as lipids, may be pre-mixed in an aqueous environment and then spray dried to produce gas filled vesicles. The vesicles may be stored under a headspace of a desired gas.

Many liposomal preparatory techniques which may be adapted for use in the preparation of vesicle compositions are discussed, for example, in U.S. Pat. Nos. 4,728,578, 4,728,575, 4,737,323, 4,533,254, 4,162,282, 4,310,505, and 4,921,706; U.K. Patent Application GB 2193095 A; International Application Serial No. PCT/US85/01161; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); International Application Serial No. PCT/US89/05040; and *Liposome Technology*, Gregoriadis, ed., Vol. I, pp. 29–31, 51–67 and 79–108 (CRC Press Inc., Boca Raton, Fla. 1984), the disclosures of each of which are hereby incorporated by reference herein in their entirety.

In connection with stabilizing materials, and especially lipid compositions in the form of vesicles, it may be advantageous to prepare the lipid compositions at a temperature below the gel to liquid crystalline phase transition temperature of the lipids. This phase transition temperature is the temperature at which a lipid bilayer will convert from a gel state to a liquid crystalline state. See, for example, Chapman et al., *J. Biol. Chem.*, 249:2512–2521 (1974), the disclosure of which is hereby incorporated by reference herein in its entirety. It is generally believed that vesicles which are prepared from lipids that possess higher gel state to liquid crystalline state phase transition temperatures tend to have enhanced impermeability at any given temperature. See Derek Marsh, *CRC Handbook of lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984). The following table lists some of the representative lipids and their phase transition temperatures.

TABLE 3

Saturated Diacyl-sn-Glycero-3-Phosphocholines:
Main Chain Melting Transition Temperatures

| Number of Carbons in Acyl Chains | Main Phase Transition Temperature (° C.) |
| --- | --- |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, CRC Handbook of Lipid Bilayers, p. 139 (CRC Press, Boca Raton, FL 1990).

Stabilizing materials, such as lipids, comprising a gas can be prepared by agitating an aqueous solution containing, if desired, a stabilizing material, in the presence of a gas. The term "agitating" means any shaking motion of an aqueous solution such that gas is introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay, Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicles. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations is from about 1000 to about 20,000 per minute. More preferably, the number of reciprocations or oscillations is from about 2500 to about 8000, with reciprocations or oscillations of from about 3300 to about 5000 being even more preferred. Of course, the number of oscillations can be dependent upon the mass of the contents being agitated. Generally speaking, a larger mass requires fewer oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in U.S. Pat. Nos. 5,469,854, 5,580,575, 5,585,112, and 5,542,935, and U.S. application Ser. No. 08/307,305, filed Sep. 16, 1994, the disclosures of each of which are incorporated herein by reference in their entirety. Emulsion processes may also be employed in the preparation of compositions in accordance with the present invention. Such emulsification processes are described, for example, in Quay, U.S. Pat. Nos. 5,558,094, 5,558,853, 5,558,854, and 5,573,751, the disclosures of each of which are hereby incorporated herein by reference in their entirety. Spray drying may be also employed to prepare the gaseous precursor filled vesicles. Utilizing this procedure, the lipids may be pre-mixed in an aqueous environment and then spray dried to produce gaseous precursor filled vesicles. The vesicles may be stored under a headspace of a desired gas. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay, Germany), using, for example, the techniques disclosed in U.S. application Ser. No. 160,232, filed Nov. 30, 1993, the disclosures of which are hereby incorporated herein by reference in its entirety. In addition, after extrusion and sterilization procedures, which are discussed in detail below, agitation or shaking may provide vesicle compositions which can contain substantially no or minimal residual anhydrous lipid phase in the remainder of the solution. (Bangham, et al, *J. Mol. Biol.* 13:238–252 (1965)). Other preparatory techniques include those described in Unger, U.S. Pat. No. 5,205,290, the disclosure of which is hereby incorporated herein by reference in its entirety.

Foams comprise an additional embodiment of the invention. Foams find biomedical application in implants for local delivery of drugs, tissue augmentation, wound healing, and prevention of peritoneal adhesions. Phospholipid foams can be created by increasing the concentration of the phospholipids as well as by mixing with materials such as cetyl alcohol, surfactants, simethicone or polymers, such as methylcellulose. Fluorinated phospholipids may also be used to create stable, long-lasting foams. The most stable foams are generally prepared from materials which are polymerized or cross-linked, such as polymerizable phospholipids. Since foaming is also a function of surface tension reduction, detergents are generally useful foaming agents.

Foams can also be produced by shaking gas filled vesicles, wherein the foam appears on the top of the aqueous solution, and is coupled with a decrease in the volume of the aqueous solution upon the formation of foam. Preferably, the final volume of the foam is at least about two times the initial volume of the aqueous stabilizing material solution; more preferably, the final volume of the foam is at least about three times the initial volume of the aqueous solution; even more preferably, the final volume of the foam is at least about four times the initial volume of the aqueous solution; and most preferably, all of the aqueous stabilizing material solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gas filled liposomes becomes sufficiently thick so that it no longer clings to the side walls as it is swirled. At this time, the foam may cause the solution containing the gas filled liposomes to raise to a level of 30 to 35 ml.

The concentration of lipid required to form a preferred foam level will vary depending upon the type of lipid used, and may be readily determined by one skilled in the art, in view of the present disclosure. For example, in preferred embodiments, the concentration of 1,2-dipalmitoylphosphatidylcholine (DPPC) used to form gas filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

Microemulsification is a common method of preparing an emulsion of a foam precursor. Temperature increases and/or lowered pressures will cause foaming as gas bubbles form in the liquid. As discussed above, the foam may be stabilized by, for example, surfactants, detergents or polymers.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 $\mu$m to greater than about 100 $\mu$m. In addition, after extrusion and sterilization procedures, which are discussed in detail below, agitation or shaking provides vesicle compositions which provide substantially no or minimal residual anhydrous lipid phase in the remainder of the solution. (Bangham, et al, *J. Mol. Biol.*, 13:238–252 (1965)). If desired, the vesicles of the present invention may be used as they are formed, without any attempt at further modification of the size thereof. For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 $\mu$m to about 100 $\mu$m.

The gas filled vesicles may be sized by a simple process of extrusion through filters wherein the filter pore sizes control the size distribution of the resulting gas filled vesicles. By using two or more cascaded or stacked set of filters, for example, a 10 μm filter followed by an 8 μm filter, the gas filled vesicles can be selected to have a very narrow size distribution around 7 to 9 μm. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by an extraction step which comprises extruding the vesicles from the barrel through the filter fitted to the syringe between the barrel and the needle, thereby sizing the vesicles before they are administered to a patient. The extraction step may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

In certain preferred embodiments, the vesicle compositions may be heat sterilized or filter sterilized and extruded through a filter prior to shaking. Generally speaking, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and/or gaseous precursor filled vesicles provide sterile gas and/or gaseous precursor filled vesicles ready for administration to a patient. For example, a mixing vessel such as a vial or syringe may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 μm, more preferably, about 0.1 to about 4 μm, even more preferably, about 0.1 to about 2 μm, and still more preferably, about 1 μm. Unhydrated compound, which is generally undesirable, appears as amorphous clumps of non-uniform size.

The sterilization step provides a composition that may be readily administered to a patient for diagnostic imaging including, for example, ultrasound or CT. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, the extrusion and heating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, upon activation, for example, by exposure to elevated temperature, varying pH, or light, undergo a phase transition from, for example, a liquid, including a liquid entrapped in a vesicle, to a gas, expanding to create the gas filled vesicles described herein. This technique is described in detail in U.S. patent application Ser. No. 08/159,687, filed Nov. 30, 1993, and U.S. Pat. No. 5,542,935, the disclosures of which are hereby incorporated herein by reference in their entirety.

The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about −100° C. to about 70° C. The activation temperature is particular to each gaseous precursor. An activation temperature of about 37° C., or about human body temperature, is preferred for gaseous precursors in the context of the present invention. Thus, in preferred form, a liquid gaseous precursor is activated to become a gas at about 37° C. or below. The gaseous precursor may be in liquid or gaseous phase for use in the methods of the present invention.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are preformed prior to use. In this embodiment, the gaseous precursor is added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane (4° C.), perfluorobutane gas is entrapped in the vesicles.

Accordingly, the gaseous precursors may be selected to form gas filled vesicles in vivo or may be designed to produce the gas filled vesicles in situ, during the manufacturing process, on storage, or at some time prior to use. A water bath, sonicator or hydrodynamic activation by pulling back the plunger of a syringe against a closed stopcock may be used to activate targeted gas filled vesicles from temperature-sensitive gaseous precursors prior to intravenous injection.

As a further embodiment of this invention, by preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, one would be able to predict an upper limit to the size of the gas filled vesicle.

In embodiments of the present invention, a mixture of a lipid compound and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is as follows:

$$PV=nRT$$

where: P is pressure in atmospheres (atm); V is volume in liters (L); n is moles of gas; T is temperature in degrees Kelvin (K); and R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation: Volume (spherical vesicle)=$4/3\pi r^3$, where r is the radius of the sphere.

Once the volume is predicted, and knowing the density of the liquid at the desired temperature, the amount of liquid gaseous precursor in the droplet may be determined. In more descriptive terms, the following can be applied:

$$V_{gas}=4/3\pi(r_{gas})^3$$

by the ideal gas law, $$PV=nRT$$

substituting reveals, $$V_{gas}=nRT/P_{gas}$$

or, $$n=4/3[\pi r_{gas}^3]P/RT \quad (A)$$

amount $n=4/3[\pi r_{gas}^3 P/RT]\cdot MW_n$
Converting back to a liquid volume $$V_{liq}=[4/3[\pi r_{gas}^3]P/RT]\cdot MW_n/D] \quad (B)$$

where D is the density of the precursor.
Solving for the diameter of the liquid droplet, $$\text{diameter}/2=[3/4\pi[4/3\cdot[\pi r_{gas}^3]P/RT]Mw_n/D]]^{1/3} \quad (C)$$

which reduces to Diameter=$2[[r_{gas}^3]P/RT[MW_n/D]]^{1/3}$.

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 μm diameter. In this example, the vesicle is formed in the bloodstream of a human being, thus the typical temperature would be 37° C. or 310 K. At a pressure of 1 atmosphere and using the equation in (A), $7.54 \times 10^{-17}$ moles of gaseous precursor would be required to fill the volume of a 10 μm diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor would be required for a 10 μm vesicle. Extrapolating further, and with the knowledge of the density, equation (B) further predicts that $8.47 \times 10^{-16}$ mL of liquid precursor is necessary to form a vesicle with an upper limit of 10 μm.

Finally, using equation (C), a mixture, for example, an emulsion containing droplets with a radius of 0.0272 μm or a corresponding diameter of 0.0544 μm, is formed to make a gaseous precursor filled vesicle with an upper limit of a 10 μm vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation:

$$\ln x_a = \ln(1-x_b) = \Delta H_{fus}/R(1/T_o - 1T)$$

where $x_a$ is the mole fraction of the solvent; $x_b$ is the mole fraction of the solute; $\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as:

$$x^b = \Delta H_{fus}/R[T-T_o/T_oT] = \Delta H_{fus}\Delta T/RT_o^2$$

The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows.

$$X_b = m/[m+1000/m_a] = mMa/1000$$

where Ma is the molecular weight of the solvent.

Thus, substituting for the fraction $x_b$:

$$\Delta T = [M_a RT_o^2/1000\Delta H_{fus}]m$$

or $$\Delta T = K_f m, \text{ where } K_f = M_a RT_o^2/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 µm. Alternatively, filtering may be performed during in vivo administration of the vesicles such that a filter of about 0.22 µm is employed;

(b) microemulsification whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool.

Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* (1978) 75:4194–4198. In contrast, the vesicles made according to certain preferred embodiments described herein are gaseous precursor filled, which imparts greater flexibility, since gaseous precursors after gas formation are more compressible and compliant than an aqueous solution.

The methods contemplated by the present invention provide for shaking an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, a gas, such as air, may also be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

Hence, the gaseous precursor filled vesicles can be used in substantially the same manner as the gas filled vesicles described herein, once activated by application to the tissues of a host, where such factors as temperature or pH may be used to cause generation of the gas. It is preferred that the gaseous precursors undergo phase transitions from liquid to gaseous states at or near the normal body temperature of the host, and are thereby activated, for example, by the in vivo temperature of the host so as to undergo transition to the gaseous phase therein. Alternatively, activation prior to intravenous injection may be used, for example, by thermal, mechanical or optical means. This activation can occur where, for example, the host tissue is human tissue having a normal temperature of about 37° C. and the gaseous precursors undergo phase transitions from liquid to gaseous states near 37° C.

In any of the techniques described above for the preparation of lipid-based vesicles, the steroid prodrugs and/or the targeting ligands may be incorporated with the lipids before, during or after formation of the vesicles, as would be apparent to one of ordinary skill in the art, in view of the present disclosure.

Conjugates of steroids and fluorinated surfactants or conjugates of targeting ligands and fluorinated surfactants can be synthesized by variations on a theme suggested by the reaction sequence set forth in the present disclosure and according to methods known to those skilled in the art, as disclosed, for example, by Quay, et al, European Patent Publication EP 0 727 225 A2, the disclosure of which is hereby incorporated herein by reference in its entirety. If the prodrug of choice contains a fluorinated surfactant, such as ZONYL® FSN-100, the ZONYL® can be heated at reduced pressure to drive off volatile components, then the oily residue is reacted with a conjugation linker, the choice of which will ultimately depend on the chemistry of the functional groups on the steroid to be formulated into a prodrug. Alternatively, the steroid could be activated by methods well-known in the art. For example, targeting ligand and fluorinated surfactant conjugates can be prepared by the reaction schemes below, where "LIG" refers to a targeting ligand of the present invention and "$R_f$" refers to a fluorinated surfactant of the present invention.

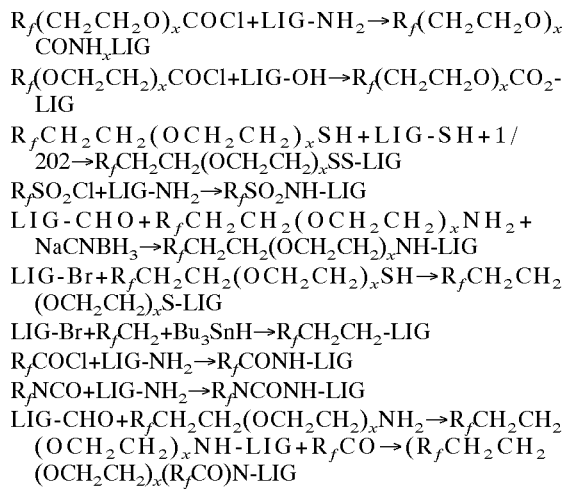

With respect to polyethylene glycol containing fragments, the following can be used, for example, PEG2-NHS ester, NHS-PEG-VS, NHS-PEG-MAL, methoxy-PEG-vinylsulfone, PEG-(VS)$_2$, methoxy-PEG-ald$_2$, PEG-(ald)$_2$, methoxy-PEG-epx, PEG-(epx)$_2$, methoxy-PEG-Tres, PEG-(Tres)$_2$, methoxy-PEG-NPC, PEG-(NPC)$_2$, methoxy-PEG-CDI, PEG-(CDI)$_2$, mPEG-Gly-OSu, mPEG-NLe-OSu, methoxy-SPA-PEG, (SPA)$_2$-PEG, methoxy-SS-PEG, (SS)$_2$-PEG all of which are available from Shearwater Polymers, Inc. (Huntsville, Ala.). Where these types of fragments are used, i.e., where the fragments may not themselves have surfactant properties adequate for a given ultrasound contrast formulation, or act only weakly as surfactants, the conjugate formed can be used in conjunction with other surfactants in the final formulation.

Vesicle compositions which comprise vesicles formulated from proteins, such as albumin vesicles, may be prepared by various processes, as will be readily apparent to those skilled in the art in view of the present disclosure. Suitable methods include those described, for example, in U.S. Pat. Nos. 4,572,203, 4,718,433, 4,774,958, and 4,957,656, the disclosures of each of which are hereby incorporated herein by reference in their entirety. Included among the methods are those which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, and collagen, preferably, the protein is a human protein, with human serum albumin (HSA) being more preferred. HSA is available commercially as a sterile 5% aqueous solution, which is suitable for use in the preparation of protein-based vesicles. As would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

Protein-based vesicles may be prepared using equipment which is commercially available. For example, in connection with a feed perparation operation as disclosed, for example, in U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonicating vessel, in series. Heat exchanger equipment of this type may be obtained from ITT Standard (Buffalo, N.Y.). The heat exchanger maintains operating temperature for the sonciation process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commercially available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficient to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally speaking, intense foaming and aerosolating are important for obtaining a contrast agent having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteradehyde per gram of protein at pH 4.5 for 6 hours. The unreacted gluteraldehyde may then be washed away from the protein.

In any of the techniques described above for the preparation of protein-based stabilizing materials and/or vesicles, the steroid prodrugs and/or targeting ligands may be incorporated with the proteins before, during or after formation of the vesicles, as would be apparent to one of ordinary skill in the art, based on the present disclosure.

Vesicle compositions which comprise vesicles formulated from polymers may be prepared by various processes, as will be readily apparent to those skilled in the art in view of the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures disclosed in U.S. Pat. Nos. 4,179,546, 3,945,956, 4,108,806, 3,293,114, 3,401,475, 3,479,811, 3,488,714, 3,615,972, 4,549,892, 4,540,629, 4,421,562, 4,420,442, 4,898,734, 4,822,534, 3,732,172, 3,594,326, and 3,015,128; Japan Kokai Tokkyo Koho 62 286534, British Patent No. 1,044,680, Deasy, *Microencapsulation and Related Drug Processes*, Vol. 20, Chs. 9 and 10, pp. 195–240 (Marcel Dekker, Inc., N.Y., 1984), Chang et al., *Canadian J. of Physiology and Pharmacology*, 44:115–129 (1966), and Chang, *Science*, 146:524–525 (1964), the disclosures of each of which are hereby incorporated herein by reference in their entirety.

In accordance with a preferred synthesis protocol, the vesicles may be prepared using a heat expansion process, such as, for example, the process described in U.S. Pat. Nos. 4,179,546, 3,945,956, and 4,108,806, British Patent No. 1,044,680, and Japan Kokai Tokkyo Koho 62 286534. In general terms, the heat expansion process may be carried out by preparing vesicles of an expandable polymer or copolymer which may contain in their void (cavity) a volatile liquid (gaseous precursor). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles.

Polymers useful in the heat expansion process will be readily apparent to those skilled in the art and include thermoplastic polymers or copolymers, including polymers or copolymers of many of the monomers described above. Preferable of the polymers and copolymers described above include the following copolymers: polyvinylidene-polyacrylo-nitrile, polyvinylidene-polyacrylonitrile-polymethylmethacrylate, and polystyrene-polyacrylonitrile. A most preferred copolymer is polyvinylidene-polyacrylonitrile.

Volatile liquids useful in the heat expansion process will also be well known to those skilled in the art and include: aliphatic hydrocarbons such as ethane, ethylene, propane, propene, butane, isobutane, neopentane, acetylene, hexane, heptane; chlorofluorocarbons such as $CCl_3F$, $CCl_2F_3$, $CClF_3$, $CClF_2-CCl_2F_2$, chloroheptafluoro-cyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. In general, it is important that the volatile liquid not be a solvent for the polymer or copolymer being utilized. It is also preferred that the volatile liquid have a boiling point that is below the softening point of the involved polymer or copolymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles. After heat is removed, the expanded polyvinylidene and acrylonitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

In any of the techniques described above for the preparation of polymer-based stabilizing materials and/or vesicles, the steroid prodrugs and/or targeting ligands may be incorporated with the polymers before, during or after formation of the vesicles, as would be apparent to one of ordinary skill in the art, based on the present disclosure.

As with the preparation of stabilizing materials and/or vesicles, a wide variety of techniques are available for the preparation of stabilizing materials comprising bioactive agents (which includes steroid prodrugs and targeting ligands). For example, the stabilizing materials and/or vesicle compositions may be prepared from a mixture of lipid compounds, bioactive agents and gases and/or gaseous precursors. In this case, lipid compositions are prepared as described above in which the compositions also comprise bioactive agents. Thus, for example, micelles can be prepared in the presence of a bioactive agent. In connection with lipid compositions which comprise a gas, the preparation can involve, for example, bubbling a gas directly into a mixture of the lipid compounds and one or more additional materials. Alternatively, the lipid compositions may be preformed from lipid compounds and gas and/or gaseous precursor. In the latter case, the bioactive agent is then added to the lipid composition prior to use. For example, an aqueous mixture of liposomes and gas may be prepared to which the bioactive agent is added and which is agitated to provide the liposome composition. The liposome composition can be readily isolated since the gas and/or bioactive agent filled liposome vesicles generally float to the top of the aqueous solution. Excess bioactive agent can be recovered from the remaining aqueous solution.

As those skilled in the art will recognize, any of the stabilizing materials and/or vesicle compositions may be lyophilized for storage, and reconstituted or rehydrated, for example, with an aqueous medium (such as sterile water, phosphate buffered solution, or aqueous saline solution), with the aid of vigorous agitation. Lyophilized preparations generally have the advantage of greater shelf life. To prevent agglutination or fusion of the lipids and/or vesicles as a result of lyophilization, it may be useful to include additives which prevent such fusion or agglutination from occurring. Additives which may be useful include sorbitol, mannitol, sodium chloride, glucose, dextrose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosure of which is hereby incorporated herein by reference in its entirety.

The concentration of lipid required to form a desired stabilized vesicle level will vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The amount of composition which is administered to a patient can vary. Typically, the intravenous dose may be less than about 10 mL for a 70 Kg patient, with lower doses being preferred.

Another embodiment of preparing a targeted therapeutic steroid prodrug composition comprises combining at least one biocompatible lipid and a gaseous precursor; agitating until gas filled vesicles are formed; adding a steroid prodrug and/or targeting ligand to said gas filled vesicles such that the steroid prodrug and/or targeting ligand binds to said gas filled vesicle by a covalent bond or non-covalent bond; and agitating until a delivery vehicle comprising gas filled vesicles and a steroid prodrug and/or targeting ligand result. Rather than agitating until gas filled vesicles are formed before adding the steroid prodrug and/or targeting ligand, the gaseous precursor may remain a gaseous precursor until the time of use. That is, the gaseous precursor is used to prepare the delivery vehicle and the precursor is activated in vivo, by temperature for example.

Alternatively, a method of preparing targeted therapeutic steroid prodrug compositions may comprise combining at least one biocompatible lipid and a steroid prodrug and/or targeting ligand such that the steroid prodrug and/or targeting ligand binds to said lipid by a covalent bond or non-covalent bond, adding a gaseous precursor and agitating until a delivery vehicle comprising gas-filled vesicles and a steroid prodrug and/or targeting ligand result. In addition, the gaseous precursor may be added and remain a gaseous precursor until the time of use. That is, the gaseous precursor is used to prepare the delivery vehicle having gaseous precursor filled vesicles and a steroid prodrug and/or targeting ligand which result for use in vivo.

Alternatively, the gaseous precursors may be utilized to create stable gas filled vesicles with steroid prodrugs and/or targeting ligands which are pre-formed prior to use. In this embodiment, the gaseous precursor and steroid prodrug and/or targeting ligand are added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas for example, air, or coentrap gas state gaseous precursor and ambient air. This phase transition can be used for optimal mixing and stabilization of the delivery vehicle. For example, the gaseous precursor, perfluorobutane, can be entrapped in the biocompatible lipid or other stabilizing compound, and as the temperature is raised, beyond 4° C. (boiling point of perfluorobutane) stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles and steroid prodrugs and/or targeting ligand result.

Accordingly, the gaseous precursors may be selected to form a gas filled vesicle in vivo or may be designed to produce the gas filled vesicle in situ, during the manufacturing process, on storage, or at some time prior to use.

According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

Hence, the stabilized vesicle precursors described above, can be used in the same manner as the other stabilized vesicles used in the present invention, once activated by application to the tissues of a host, where such factors as temperature or pH may be used to cause generation of the gas. It is preferred that this embodiment is one wherein the gaseous precursors undergo phase transitions from liquid to gaseous states at or near the normal body temperature of said host, and are thereby activated by the temperature of said host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the compositions including, for example, sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The compositions are generally stored as an aqueous suspension but in the case of dried or lyophilized vesicles or dried or lyophilized lipidic spheres the compositions may be stored as a dried or lyophilized powder ready to be reconstituted or rehydrated prior to use.

Applications

The stabilizing materials of the present invention are useful as contrast media in diagnostic imaging, and for use in all areas where diagnostic imaging is employed. Diagnostic imaging is a means to visualize internal body regions of a patient, and includes, for example, ultrasound (US), magnetic resonance imaging (MRI), nuclear magnetic resonance (NMR), computed tomography (CT), electron spin resonance (ESR); nuclear medicine when the contrast medium includes radioactive material; and optical imaging, particularly with a fluorescent contrast medium. Diagnostic imaging also includes promoting the rupture of vesicles via the methods of the present invention. For example, ultrasound may be used to visualize the vesicles and verify the localization of the vesicles in certain tissue. In addition, ultrasound may be used to promote rupture of the vesicles once the vesicles reach the intended target, including tissue and/or receptor destinations, thus releasing a bioactive agent, such as a steroid prodrug.

In accordance with the present invention, there are provided methods of imaging a patient generally, diagnosing the presence of diseased tissue in a patient and/or delivering a bioactive agent to a patient. The imaging process of the present invention may be carried out by administering a composition of the invention to a patient, and then scanning the patient using, for example, ultrasound, computed tomography, and/or magnetic resonance imaging, to obtain visible images of an internal region of a patient and/or of any diseased tissue in that region. The contrast medium may be particularly useful in providing images of tissue, such as myocardial, endothelial, and/or epithelial tissue, as well as the gastrointestinal and cardiovascular regions, but can also be employed more broadly, such as in imaging the vasculature, or in other ways as will be readily apparent to those skilled in the art. Cardiovascular region denotes the region of the patient defined by the heart and the vasculature leading directly to and from the heart. The phrase vasculature denotes the blood vessels (arteries, veins, etc.) in the body or in an organ or part of the body. The patient can be any type of mammal, but most preferably is a human.

The present invention also provides a method of diagnosing the presence of diseased tissue. Diseased tissue includes, for example, endothelial tissue which results from vasculature that supports diseased tissue. As a result, the localization and visualization of endothelial tissue to a region of a patient which under normal circumstances is not associated with endothelial tissue provides an indication of diseased tissue in the region. The present methods can also be used in connection with delivery of a bioactive agent, such as a steroid prodrug, to an internal region of a patient.

The compositions of the invention, including the steroid prodrugs, may be administered to the patient by a variety of different means. The means of administration will vary depending upon the intended application. As one skilled in the art would recognize, administration of the steroid prodrug or the steroid prodrug in combination with the stabilizing materials and/or vesicles of the present invention can be carried out in various fashions, for example, topically, including ophthalmic, dermal, ocular and rectal, intrarectally, transdermally, orally, intraperitoneally, parenterally, intravenously, intralymphatically, intratumorly, intramuscularly, interstitially, intra-arterially, subcutaneously, intraocularly, intrasynovially, transepithelially, pulmonarily via inhalation, ophthalmically, sublingually, buccally, or via nasal inhalation via insufflation or nebulization. Preferably, the steroid prodrugs and/or stabilizing materials of the present invention are administered intravenously or topically/transdermally.

Ultrasound mediated targeting and drug release and activation using the steroid prodrugs of the present invention is advantageous for treating a variety of different diseases and medical conditions, such as autoimmune diseases, organ transplants, arthritis, and myasthenia gravis. Following the systemic administration of the steroid prodrug delivery vehicles to a patient, ultrasound may then be applied to the affected tissue. For arthritis, including synovial-based inflammation arthritis, such as rheumatoid arthritis, ultrasound may be applied to the joints affected by the disease. For myasthenia gravis, ultrasound may be applied to the thymus. For transplant rejection, ultrasound may be applied to the organ transplant, such as in a kidney transplant.

For topical applications, the steroid prodrugs may be used alone, may be mixed with one or more solubilizing agents or may be used with a delivery vehicle, and applied to the skin or mucosal membranes. Other penetrating and/or solubilizing agents useful for the topical application of the steroid prodrug include, for example, pyrrolidones such as 2-pyrrolidone, N-methyl-2-pyrrolidone, 1-methyl-2-pyrrolidone, 5-methyl-2-pyrrolidone, 1-ethyl-2-pyrrolidone, 2-pyrrolidone-5-carboxylic acid, N-hydroxyethylpyrrolidone, N-cyclohexylpyrrolidone, N-dimethylaminopropylpyrrolidone, N-cocalyklpyrrolidone, N-tallowalkylpyrrolidone, 1-lauryl-2-pyrrolidone, and 1-hyxyl-2-pyrrolidone; fatty acids such as oleic acid, linoleic acid, heptanoic acid, caproic acid, lauric acid, stearic acid, octadecenoic acid, palmitoleic acid, myristic acid and palmitelaidic acid; sulfoxides such as dimethylsulfoxide, dimethylacetamide, dimethylformamide, N-methylformamide and decylmethylsulfoxide; amines and derivatives such as N,N-diethyl-m-toluamide, dodecylamine, ethoxylated amine, N,N-bis(2-hydroxyethyl)oleylamine, dodecyl-N,N-dimethylamino acetate, sodium pryoglutaminate and N-hydroxylethalacetamide; terpenes and terpenoids such as a-pinenes, d-limonene, 3-carene, a-terpineol, terpinen-4-ol, careol, abisabolol, carvone, pulegone, piperitone, menthone, fenchone, cyclohexene oxide, limonene oxide, pinene oxide, cyclopentene oxide, ascaridol, 7-oxabicyclo(2.2.1)heptane, 1,8-cineole, safrole, 1-carvone, terpenoid cyclohexanone derivatives, acyclic terpenehydrocarbon chains, hydrocarbon terpenes, cyclic ether terpenes, cardamon seed extract, monoterpene terpineol and acetyl terpineol; essential oils of eucalyptus, chenopodium and yang ylang; surfactants such as anionic-sodiumlaurylsulfate, phenylsulfurate CA, calciumdodecylbenzene sulfonate, empicol ML26/F and magnesiumlaurylsulfate; cationic-cetyltrimethyl-ammonium bromide; nonionic-synperonic NP series and PE series and the polysorbates; zwiterionic-N-dodecyl-N,N-dimethylbetaine; alcohols such as ethanol, lauryl alcohol, linolenyl alcohol, 1-octanol, 1-propanol and 1-butanol; urea, cyclic unsaturated urea analogs, glycols, azone, n-alkanols, n-alkanes, orgelase, alphaderm cream and water. The penetrating/solubilizing agents may or may not be in a base which can be composed of various substances known to those skilled in the art, including, for example, glycerol, propylene glycol; isopropyl myristate; urea in propylene glycol, ethanol and water; and polyethylene glycol (PEG).

The steroid prodrugs formulated with penetration enhancing agents, known to those skilled in the art and described above, may be administered transdermally in a patch or reservoir with a permeable membrane applied to the skin. The use of rupturing ultrasound may increase transdermal delivery of therapeutic compounds, including the steroid prodrugs of the present invention. Further, an imaging mechanism may be used to monitor and modulate delivery of the steroid prodrugs. For example, diagnostic ultrasound may be used to visually monitor the bursting of the gas filled vesicles and modulate drug delivery and/or a hydrophone may be used to detect the sound of the bursting of the gas filled vesicles and modulate drug delivery.

The delivery of bioactive agents from the stabilizing materials of the present invention using ultrasound is best accomplished for tissues which have a good acoustic window for the transmission of ultrasonic energy. This is the case for most tissues in the body such as muscle, the heart, the liver and most other vital structures. In the brain, in order to direct the ultrasonic energy past the skull a surgical window may be necessary.

The gas filled vesicles of the invention are especially useful for bioactive agents that may be degraded in aqueous media or upon exposure to oxygen and/or atmospheric air. For example, the vesicles may be filled with an inert gas such as nitrogen or argon, for use with labile bioactive agents. Additionally, the gas filled vesicles may be filled with an inert gas and used to encapsulate a labile bioactive agents for use in a region of a patient that would normally cause the therapeutic to be exposed to atmospheric air, such as cutaneous and ophthalmic applications.

The invention is useful in delivering bioactive agents to a patient's lungs. For pulmonary applications of the steroid prodrugs, dried or lyophilized powdered liposomes may be administered via inhaler. Aqueous suspensions of liposomes or micelles, preferably gas/gaseous precursor filled, may be administered via nebulization. Gas filled liposomes of the present invention are lighter than, for example, conventional liquid filled liposomes which generally deposit in the central proximal airway rather than reaching the periphery of the lungs. It is therefore believed that the gas filled liposomes of the present invention may improve delivery of a bioactive agent to the periphery of the lungs, including the terminal airways and the alveoli. For application to the lungs, the gas filled liposomes may be applied through nebulization.

In applications such as the targeting of the lungs, which are lined with lipids, the bioactive agent may be released upon aggregation of the gas filled liposomes with the lipids lining the targeted tissue. Additionally, the gas filled liposomes may burst after administration without the use of ultrasound. Thus, ultrasound need not be applied to release the drug in the above type of administration.

For vascular administration the steroid prodrugs are generally injected into the venous system as a formulation vehicle, e.g. preferably gas or gaseous precursor containing liposomes.

It is a further embodiment of this invention in which ultrasound activation affords site specific delivery of the steroid prodrugs. Generally, the gas and/or gaseous precursor containing vehicles are echogenic and visible on ultrasound. Ultrasound can be used to image the target tissue and to monitor the drug carrying vehicles as they pass through the treatment region. As increasing levels of ultrasound are applied to the treatment region, this breaks apart the delivery vehicles and/or releases the drug within the treatment region. "Release of the drug" or "release of the steroid" includes: (1) the release of the steroid prodrug from the delivery vehicle but not the release of the steroid from the linking group and lipid moiety; (2) the release of the steroid from the covalently bonded lipid moiety and/or the linking group, but not from the delivery vehicle; and (3) the release of the steroid from both the delivery vehicle and from the covalently bonded lipid moiety and/or the linking group. Preferably, "release of the drug/steroid" is (1) the release of the steroid prodrug from the delivery vehicle but not the release of the steroid from the linking group and lipid moiety or (3) the release of the steroid from both the delivery vehicle and from the covalently bonded lipid moiety and linking group.

Drug release and/or vesicle rupture can be monitored ultrasonically by several different mechanisms. Bubble or vesicle destruction results in the eventual dissolution of the ultrasound signal. However, prior to signal dissolution, the delivery vehicles/vesicles provide an initial burst of signal. In other words, as increasing levels of ultrasound energy are applied to the treatment zone containing the delivery vehicles/vesicles, there is a transient increase in signal. This transient increase in signal may be recorded at the fundamental frequency, the harmonic, odd harmonic or ultraharmonic frequency.

The useful dosage to be administered and the particular mode of administration will vary depending upon the age, weight and the particular mammal and region thereof to be scanned, and the particular contrast agent employed. Typically, dosage is initiated at lower levels and increased until the desired contrast enhancement is achieved. Various combinations of the lipid compositions may be used to alter properties as desired, including viscosity, osmolarity or palatability.

Generally, the steroid prodrugs, stabilizing materials and/or vesicles of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may be buffered, if desired, to provide a pH range of about 5 to about 7.4. Preferably, dextrose or glucose is included in the media. Other solutions that may be used for administration of gas filled liposomes include, for example, almond oil, corn oil, cottonseed oil, ethyl oleate, isopropyl myristate, isopropyl palmitate, mineral oil, myristyl alcohol, octyldodecanol, olive oil, peanut oil, persic oil, sesame oil, soybean oil, and squalene.

The size of the stabilizing materials and/or vesicles of the present invention will depend upon the intended use. With smaller liposomes, resonant frequency ultrasound will generally be higher than for the larger liposomes. Sizing also serves to modulate resultant liposomal biodistribution and clearance. In addition to filtration, the size of the liposomes can be adjusted, if desired, by procedures known to one skilled in the art, such as shaking, microemulsification, vortexing, filtration, repeated freezing and thawing cycles, extrusion, extrusion under pressure through pores of a defined size, sonication, homogenization, the use of a laminar stream of a core of liquid introduced into an immiscible sheath of liquid. See, for example, U.S. Pat. Nos. 4,728,578, 4,728,575, 4,737,323, 4,533,254, 4,162,282, 4,310,505 and 4,921,706; U.K. Patent Application GB 2193095 A; International Applications PCT/US85/01161 and PCT/US89/05040; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); and *Liposomes Technology*, Gregoriadis, G., ed., Vol. I, pp. 29–37, 51–67 and 79–108 (CRC Press Inc, Boca Raton, Fla., 1984). The disclosures of each of the foregoing patents, publications and patent applications are hereby incorporated by reference herein in their entirety. Extrusion under pressure through pores of defined size is a preferred method of adjusting the size of the liposomes.

Since vesicle size influences biodistribution, different size vesicles may be selected for various purposes. For example, for intravascular application, the preferred size range is a mean outside diameter between about 30 nm and about 10 $\mu$m, with the preferable mean outside diameter being about 5 $\mu$m. More specifically, for intravascular application, the size of the vesicles is preferably about 10 $\mu$m or less in mean outside diameter, and preferably less than about 7 $\mu$m, and more preferably less than about 5 $\mu$m in mean outside diameter. Preferably, the vesicles are no smaller than about 30 nm in mean outside diameter. To provide therapeutic delivery to organs such as the liver and to allow differentiation of tumor from normal tissue, smaller vesicles, between about 30 nm and about 100 $\mu$m in mean outside diameter, are preferred. For embolization of a tissue such as the kidney or the lung, the vesicles are preferably less than about 200 $\mu$m in mean outside diameter. For intranasal, intrarectal or topical administration, the vesicles are preferably less than about 100 $\mu$m in mean outside diameter. Large vesicles, between 1 and about 10 $\mu$m in size, will generally be confined to the intravascular space until they are cleared by phagocytic elements lining the vessels, such as the macrophages and Kupffer cells lining capillary sinusoids. For passage to the cells beyond the sinusoids, smaller vesicles, for example, less than about 1 $\mu$m in mean outside diameter, e.g., less than about 300 nm in size, may be utilized. In preferred embodiments, the vesicles are administered individually, rather than embedded in a matrix, for example.

For in vitro use, such as cell culture applications, the gas filled vesicles may be added to the cells in cultures and then incubated. Subsequently sonic energy can be applied to the culture media containing the cells and liposomes.

In carrying out the imaging methods of the present invention, the stabilizing materials and vesicle compositions can be used alone, or in combination with diagnostic agents, bioactive agents or other agents. Such other agents include excipients such as flavoring or coloring materials.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained. With respect to ultrasound, ultrasonic imaging techniques, including second harmonic imaging, and gated imaging, are well known in the art, and are described, for example, in Uhlendorf, *IEEE Transactions on Ultrasonics, Ferroelectrics, and Frequency Control*, 14(1):70–79 (1994) and Sutherland, et al., *Journal of the American Society of Echocardiography*, 7(5):441–458 (1994), the disclosures of each of which are hereby incorporated herein by reference in their entirety. CT imaging techniques which are employed are conventional and are described, for example, in *Computed Body Tomography*, Lee, Sagel, and Stanley, eds., 1983, Ravens Press, New York, N.Y., especially the first two chapters entitled "*Physical Principles and Instrumentation*", Ter-Pogossian, and "*Techniques*", Aronberg, the disclosures of each of which are hereby incorporated by reference herein in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the targeted contrast media of the present invention which may be targeted to the desired site, for example, blood clots. Other harmonic signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of For sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle composition. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may also be pulsed. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition energy levels may vary from about 0.5 Watt (W) per square centimeter ($cm^2$) to about 5.0 $W/cm^2$, with energy levels of from about 0.5 to about 2.5 $W/cm^2$ being preferred. Energy levels for therapeutic ultrasound involving hyperthermia are generally from about 5 $W/cm^2$ to about 50 $W/cm^2$. For very small vesicles, for example, vesicles having a diameter of less than about 0.5 $\mu$m, higher frequencies of sound are generally preferred because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosure of which is hereby incorporated by reference herein in its entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, et al., *Ultrasonics Sonochemistry*, 3:1–5 (1996), the disclosure of which is hereby incorporated by reference herein in its entirety.

For use in ultrasonic imaging, preferably, the vesicles of the invention possess a reflectivity of greater than 2 dB, more preferably between about 4 dB and about 20 dB. Within these ranges, the highest reflectivity for the vesicles of the invention is exhibited by the larger vesicles, by higher concentrations of vesicles, and/or when higher ultrasound frequencies are employed.

For therapeutic drug delivery, the rupturing of the bioactive agent containing vesicle compositions and/or liposomes of the invention is surprisingly easily carried out by applying ultrasound of a certain frequency to the region of the patient where therapy is desired, after the liposomes have been administered to or have otherwise reached that region, e.g., via delivery with targeting ligands. Specifically, it has been unexpectedly found that when ultrasound is applied at a frequency corresponding to the peak resonant frequency of the bioactive agent containing gas filled vesicles, the vesicles will rupture and release their contents. The peak resonant frequency can be determined either in vivo or in vitro, but preferably in vivo, by exposing the stabilizing materials or vesicles, including liposomes, to ultrasound, receiving the reflected resonant frequency signals and analyzing the spectrum of signals received to determine the peak, using conventional means. The peak, as so determined, corresponds to the peak resonant frequency, or second harmonic, as it is sometimes termed.

Preferably, the stabilizing materials and/or vesicle compositions of the invention have a peak resonant frequency of between about 0.5 and about 10 MHz. Of course, the peak resonant frequency of the gas filled vesicles of the invention will vary depending on the outside diameter and, to some extent, the elasticity or flexibility of the liposomes, with the larger and more elastic or flexible liposomes having a lower resonant frequency than the smaller and less elastic or flexible vesicles.

The bioactive agent containing gas filled vesicles will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and release is improved, appreciable tissue heating does not generally occur (frequently no increase in temperature above about 2° C.), and less overall energy is required. Thus, application of ultrasound at the peak resonant frequency, while not required, is most preferred.

For diagnostic or therapeutic ultrasound, any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the vesicle is visualized on ultrasound (for diagnostic ultrasound applications) or ruptures (for therapeutic ultrasound applications).

Although application of the various principles will be readily apparent to one skilled in the art, in view of the present disclosure, by way of general guidance, for gas filled vesicles of about 1.5 to about 10 $\mu$m in mean outside diameter, the resonant frequency will generally be in the range of about 1 to about 10 MHz. By adjusting the focal zone to the center of the target tissue (e.g., the tumor) the gas filled vesicles can be visualized under real time ultrasound as they accumulate within the target tissue. Using the 7.5 MHz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of bioactive agents from the gas filled vesicles, but much greater release can be accomplished by using a higher power.

By switching the transducer to the doppler mode, higher power outputs are available, up to 2.5 W/cm$^2$ from the same transducer. With the machine operating in doppler mode, the power can be delivered to a selected focal zone within the target tissue and the gas filled vesicles can be made to release their contents, including bioactive agents. Selecting the transducer to match the resonant frequency of the gas filled vesicles will make this process of release even more efficient.

For larger diameter gas filled vesicles, e.g., greater than 3 $\mu$m in mean outside diameter, a lower frequency transducer may be more effective in accomplishing therapeutic release. For example, a lower frequency transducer of 3.5 MHz (20 mm curved array model) may be selected to correspond to the resonant frequency of the gas-filled vesicles. Using this transducer, 101.6 mW/cm$^2$ may be delivered to the focal spot, and switching to doppler mode will increase the power output (SPTA) to 1.02 W/cm$^2$.

To use the phenomenon of cavitation to release and/or activate the prodrugs within the gas filled stabilizing materials and/or vesicles, lower frequency energies may be used, as cavitation occurs more effectively at lower frequencies. Using a 0.757 MHz transducer driven with higher voltages (as high as 300 volts) cavitation of solutions of gas-filled liposomes will occur at thresholds of about 5.2 atmospheres.

The table below shows the ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Cleveland, Ohio Echoview 8L Scanner including 80C System or the Medisonics (Mountain View, Calif.) Model D-9 Versatone Bidirectional Doppler. In general, these ranges of energies employed in pulse repetition are useful for diagnosis and monitoring gas-filled liposomes but are insufficient to rupture the gas-filled liposomes of the present invention.

TABLE 4

Power and Intensities Produced by Diagnostic Equipment*

| Pulse repetition rate (Hz) | Total ultrasonic power output P (mW) | Average Intensity at transducer face I$_{TD}$ (W/m$^2$) |
| --- | --- | --- |
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med. & Biol., 3:341–350 (1978), the disclosure of which is hereby incorporated herein by reference in its entirety.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the liposomes and rupturing to provide local delivery of therapeutics.

Where the gas filled stabilizing materials and/or vesicles are used for drug delivery (including steroid prodrugs and/or targeting ligands), the bioactive agent to be delivered may be embedded within the wall of the vesicle, encapsulated in the vesicle and/or attached to the surface of the vesicle. The phrase "attached to" or variations thereof, as used herein in connection with the location of the bioactive agent, means that the bioactive agent is linked in some manner to the inside and/or the outside wall of the microsphere, such as through a covalent or ionic bond or other means of chemical or electrochemical linkage or interaction. The phrase "encapsulated in variations thereof" as used in connection with the location of the bioactive agent denotes that the bioactive agent is located in the internal microsphere void. The phrase "embedded within" or variations thereof as used in connection with the location of the bioactive agent, signifies the positioning of the bioactive agent within the vesicle wall(s) or layer(s). The phrase "comprising a bioactive agent" denotes all of the varying types of positioning in connection with the vesicle. Thus, the bioactive agent can be positioned variably, such as, for example, entrapped within the internal void of the gas filled vesicle, situated between the gas and the internal wall of the gas filled vesicle, incorporated onto the external surface of the gas filled vesicle, enmeshed within the vesicle structure itself and/or any combination thereof. The delivery vehicles may also be designed so that there is a symmetric or an asymmetric distribution of the drug both inside and outside of the stabilizing material and/or vesicle.

Any of a variety of bioactive agents may be encapsulated in the vesicles. If desired, more than one bioactive agent may be applied using the vesicles. For example, a single vesicle may contain more than one bioactive agent or vesicles containing different bioactive agents may be co-administered. By way of example, a monoclonal antibody capable of binding to melanoma antigen and an oligonucleotide encoding at least a portion of IL-2 may be administered at the same time. The phrase "at least a portion of" means that the entire gene need not be represented by the oligonucleotide, so long as the portion of the gene represented provides an effective block to gene expression. Preferably, at least one of the bioactive agents is a steroid prodrug. More preferably, one of the bioactive agents is a steroid prodrug and another bioactive agent is a targeting ligand.

Genetic and bioactive materials may be incorporated into the internal gas filled space of these vesicles during the gas installation process or into or onto the vesicle membranes of these particles. Incorporation onto the surface of these particles is preferred. Genetic materials and bioactive products with a high octanol/water partition coefficient may be incorporated directly into the layer or wall surrounding the gas but incorporation onto the surface of the gas filled vesicles is more preferred. To accomplish this, groups capable of binding genetic materials or bioactive materials are generally incorporated into the stabilizing material layers which will then bind these materials. In the case of genetic materials, this is readily accomplished through the use of cationic lipids or cationic polymers which may be incorporated into the dried lipid starting materials.

Other suitable bioactive agents include, for example, antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, and arabinosyl; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopoly-saccharide, macrophage activation factor), subunits of bacteria (such as Mycobacteria and Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, and β-lactam antibiotics (e.g., sulfazecin); hormones and steroids such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocopherol; peptides, such as manganese super oxide dimutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin, amantadine, vidarabine, and vidarabine monohydrate (adenine arabinoside, ara-A); antianginals such as diltiazem, nifedipine, verapamil, erythrityl tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as diffinisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium. In certain preferred embodiments, the bioactive agent is a monoclonal antibody, such as a monoclonal antibody capable of binding to melanoma antigen.

Other preferred bioactive agents include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers. Examples of genetic material that may be applied using the liposomes of the present invention include, for example, DNA encoding at least a portion of LFA-3, DNA encoding at least a portion of an HLA gene, DNA encoding at least a portion of dystrophin, DNA encoding at least a portion of CFTR, DNA encoding at least a portion of IL-2, DNA encoding at least a portion of TNF, and an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, *Science* 258:744–746.

A gas filled vesicle filled with oxygen gas should create extensive free radicals with cavitation. Also, metal ions from the transition series, especially manganese, iron and copper can increase the rate of formation of reactive oxygen intermediates from oxygen. By encapsulating metal ions within the vesicles, the formation of free radicals in vivo can be increased. These metal ions may be incorporated into the liposomes as free salts, as complexes, e.g., with EDTA, DTPA, DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gas filled vesicles to create free radicals on thermal stimulation.

Although not intending to be bound by any particular theory of operation, an example of the use of the steroid prodrugs of the present invention includes attaching an acylated chemical group to the steroid via an ester linkage which would readily cleave in vivo by enzymatic action in serum. The acylated steroid prodrug may then be incorporated into the gas filled vesicle or stabilizing material. Thereafter, the steroid prodrug may be delivered to the appropriate tissue or receptor via a targeting ligand. Upon reaching the desired tissue or receptor, the gas filled vesicle may be ruptured or popped by the sonic pulse from the ultrasound, and the steroid prodrug encapsulated by the vesicle may then be exposed to the serum. The ester linkage may then be cleaved by esterases in the serum, thereby generating the steroid. However, it is not necessary for the steroid to be cleaved from the acylated chemical group and ester linkage in order for the steroid to be therapeutically effective. In other words, the steroid prodrug may retain the bioactivity of the steroid.

Similarly, ultrasound may be utilized not only to rupture the gas filled vesicle, but also to cause thermal effects which may increase the rate of the chemical cleavage and the release of the active drug from the prodrug (e.g., release of the steroid from the linking group and lipid moiety). The particular chemical structure of the bioactive agents may be selected or modified to achieve desired solubility such that the bioactive agent may either be encapsulated within the internal gas filled space of the vesicle, attached to the surface of the vesicle, embedded within the vesicle and/or any combination thereof. The surface-bound bioactive agent may bear one or more acyl chains such that, when the vesicle is ruptured or heated or ruptured via cavitation, the acylated bioactive agent may then leave the surface and/or the bioactive agent may be cleaved from the acyl chain chemical group. Similarly, other bioactive agents may be formulated with a hydrophobic group which is aromatic or sterol in structure to incorporate into the surface of the vesicle.

Elevated temperature, such as in inflamed joints caused by rheumatoid arthritis, can be used as a complimentary mechanism for delivering entrapped steroid prodrugs from the walls of a vesicle containing a temperature sensitive precursor matrix. "Region of elevated temperature" as used herein in connection with a patient, refers to a region exhibiting a condition of elevated temperature above that of the normal bodily temperature of the region. Elevated temperature conditions can result, for example, from disease, infection, injury, etc., and include fever and inflammation states. By way of example, bacterial, viral, fungal, parasitic or other microorganismal invasion may result in an increased temperature, particularly at the site of infection. Arthritis, cancer and the presence of cardiovascular plaques may also result in increased temperature conditions. Exposure to heat, radiation, fire, etc. resulting, for example, in a burn condition, may also cause elevated temperature regions. Localized physical injuries such as tissue trauma, tears, breaks, etc., may also result in regionalized conditions of increased temperature.

While not intending to be bound by any particular theory of operation, the elevated temperature method relies, in part, on the phenomenon of elevated local temperature typically associated with disease, inflammation, infection, etc. Such conditions, which may also be referred to as physiological stress states, may elevate the temperature in a region of the patient, by a fraction of a degree or as much as 1, 2, 3, 4, 5, 6, 7, 8, 9, 10, or more degrees. For example, although normal human body temperature is about 37° C., tissue affected by disease, inflammation, infection, etc. can have temperatures greater than about 37° C., such as, for example, about 40° C. By incorporating materials which are liquid at normal physiological temperatures (i.e. the temperature of a particular mammal under normal circumstances) and which undergo a phase transition to form a gas at the elevated temperature, the methods of the present invention allow steroid prodrugs to be effectively delivered to the affected tissue and advantageously released at that site. When the gaseous precursor, for example, undergoes a phase transition from a liquid or solid to a gas, steroid prodrugs carried within the gaseous precursor may be released into the region of the tissue thereby effecting delivery of the steroid prodrug to the region of need. Thus, in accordance with the present method, other regions of the patient not affected by the regionalized condition of increased temperature are bypassed, and the steroid prodrug is selectively delivered to the region in need.

The delivery of the steroid prodrug to a desired tissue or region of the body is activated when the local temperature is at or above the phase transition temperature of the gaseous precursor. As the vesicle or non-vesicular composition or vesicles containing the gaseous precursor circulates through the patient's body, it will pass through tissues via the vasculature. As the gaseous precursor passes through a tissue or region which is at the phase transition temperature of the gaseous precursor, it will undergo transition to a gaseous state. While not intending to be bound by any particular theory of operation, it is believed that the expansion of the gaseous precursor during the phase transition forces the steroid prodrug from the vesicle or non-vesicular composition allowing it to settle in the desired region of the patient. In a preferred embodiment of the invention, the delivery of a steroid prodrug is accomplished simply due to the increase in temperature in a tissue or region associated with disease, infection, inflammation, etc. within the tissue or region.

Preferably, the gaseous precursor forms a gas at the desired tissue or region of the body, which may be at an elevated temperature as compared to the normal body temperature, due to disease, infection, inflammation, etc.

However, external heat (i.e., heat from a source other than the elevated physiological temperatures of the region) also may be applied to increase the temperature within a region or tissue of a patient, if desired. External heat may be applied by any means known in the art, such as, for example, microwave, radiofrequency, ultrasound, and other local application of heat. Local application of heat may be accomplished, for example, by a water bath or blankets. A temperature increase in a desired tissue or region of the body may be achieved by implantation of interstitial probes or insertion of a catheter, in combination with the application of an oscillating magnetic field or ultrasound energy. If ultrasound energy is used, the ultrasound energy may also interact with the gaseous precursor and/or stabilizing material, and may facilitate conversion of the gaseous precursor to a gas and/or release of a bioactive agent. As will be apparent to those skilled in the art, applied ultrasound energy may be pulsed, swept, or varied to facilitate interaction with the gaseous precursor and stabilizing material. Diagnostic ultrasound may be used in order to visualize the gaseous precursors as the gas is formed, and to visualize the tissue or region of interest.

EXAMPLES

The invention is further demonstrated in the following examples. Examples 1–6, 11, 12 and 14–17 are actual examples; Examples 7 and 8 are both actual examples (in part) and prophetic examples (in part); and Examples 9, 10, 13, 18 and 19 are prophetic examples. The examples are for purposes of illustration and are not intended to limit the scope of the present invention.

Example 1

1,2-Dipalmitoyl-sn-glycerol-3-succinate (DPGS) 0.32 g, dexamethasone 0.2 g and dimethylaminopyridine (DMAP) 10 mg were dissolved in chloroform 30 ml, and added with a solution of dicyclohexyl carbodiimide (DCC) 0.11 g in chloroform 10 ml at 0 to 5° C. for 2 hours, then stirred at room temperature over night. 2% acetic acid was then added and stirred for 2 hours, then the water phase was isolated. The organic phase was washed with 20 ml water, and then was dried over anhydrous sodium sulfate. The organic solution was evaporated on a rotaevaporator, whereby a white residue resulted. The residue was redissolved in acetonitrile, the small amount of precipitate was filtered out, and the solution was evaporated to dry, whereby a 0.5 g white solid was obtained. The crude product was recrystallized from 10 ml methanol to produce a white crystal (m.p. 37° C. to 40° C.) of 1,2-dipalmitoyl-sn-glycerol-3-succinate-dexamethasone (DPGS-Dexamethasone) of the formula:

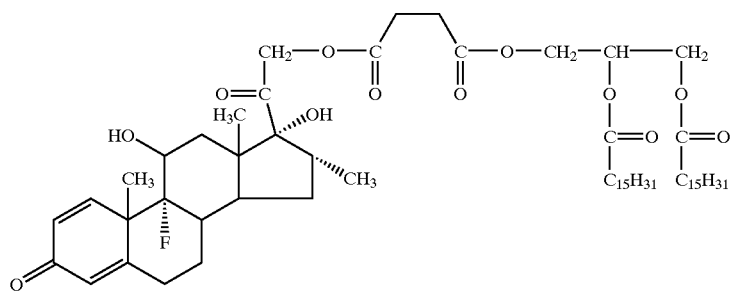

Example 2

15 weight % or 30 weight % of DPGS-dexamethasone from Example 1 was added to and incubated with a lipid mixture comprising 82 mol % dipalmitoylphosphatidylcholine (DPPC), 10 mol % dipalmitoylphosphatidic acid (DPPA), and 8 mol % dipalmitoylphosphatidylethanolamine-PEG 5000 (DPPE-PEG 5000), and was then suspended in deionized water, such that stable drug-entrapped vesicles were formed in which no dexamethasone was detected in washes or supernatants. The mixture was shell frozen in liquid nitrogen and lyophilized for 72 hours.

The mixtures comprising either 15 or 30 weight % DPGS-dexamethasone were resuspended at 1 mg/ml in a mixture of normal saline, propylene glycol and glycerol, which were in a 8:1:1 ratio. The solution was aliquotted into 2 ml Wheaton vials with a fill volume of 1.5 ml/vial. The headspace was replaced with perfluorobutane and the vials were shaken for 60 seconds on an ESPE Capmix at 4500 rpm.

The pressure stability of the vesicles comprising 15 weight % or 30 weight % DPGS-dexamethasone was compared to the pressure stability of similar vesicles that did not contain DPGS-dexamethasone. Observations at cyclic and increasing pressures indicated that at pressures over 100 to 150 mm Hg, vesicles comprising 15 weight % or 30 weight % DPGS-dexamethasone had less pressure stability than comparable vesicles that did not contain DPGS-dexamethasone. Thus, the application of pressure may theoretically be sufficient to rupture vesicles comprising DPGS-dexamethasone.

Example 3

Lipid vesicles incorporating DPGS-dexamethasone were prepared as described in Example 2. Samples of vesicles were either treated with (i) 30 seconds of therapeutic ultrasound ranging form 0.5 watts/cm$^2$ to 2.0 watts/cm$^2$ or (ii) 30 seconds with a horn sonicator. In each case the sample size was 10 $\lambda$, and the approximate DPGS-dexamethasone concentration was 10 $\mu$g/ml. In both sets of samples the vesicles were induced to burst, as was detected by the decrease in particles to zero when observed microscopically. The suspensions following sonication were dried and resuspended in acetonitrile for analysis by HPLC. The free dexamethasone and DPGS-dexamethasone peaks in the chromatogram for each fraction mirrored those seen prior to incorporation in the microspheres. From these observations, it was concluded that (1) the presence of DPGS-dexamethasone in the vesicles did not alter the ability of ultrasound to induce rupture, and (2) ultrasound at these levels does not effectuate the release of free dexamethasone.

Example 4

Lipid vesicles which are designed to evade the reticuloendothelial system were made by incubating a lipid mixture comprising 1.0 millimole dipalmitoylphosphatidylcholine (DPPC), 0.3 millimoles dipalmitoylphosphatidic acid (DPPA), and 0.05 millimole of dipalmitoylphosphatidylethanolamine-PEG5000 (DPPE-PEG 5000) and varying amounts of the DPGS-dexamethasone from Examples 1 and 2. The range of amounts of DPGS-dexamethasone were from 0.01 mM (initial concentration in the incubation mix) through 1.0 mM. Stable lipid vesicles formed with up to 0.5 mM DPGS-dexamethasone. The extrusion mixture was optimally incubated in ethylene glycol, dried under vacuum, resuspended in normal saline, lyophilized, and resuspended in dH$_2$O at a lipid concentration of 50 mg/ml. This suspension was heated to 50° C., agitated in an ESPE Capmix, then extruded at 50° C. with an Extruder Device (Lipex Biomembranes, Vancouver, BC, CANADA). Initially, two passes were made across a polycarbonate filter at 10,000 psi. An aliquot of this filtrate was passed two times across a 1.0 $\mu$m filter. A subaliquot of this filtrate was then passed two times through a 1.0 $\mu$m filter and a further subaliquot was passed through a 0.5 $\mu$m filter. This filtrate was passed through a 0.1 $\mu$m filter, and finally a portion was passed twice through 0.03 $\mu$m filter. The resulting DPGS-dexamethasone lipid containing vesicles contained fractional peak distributions sized at 2.0, 1.0, 0.5, 0.1 and 0.3 $\mu$m in diameter.

Example 5

Eight replicates each of cell lines A226 (Human Myeloma) and L1210 (Mouse Leukemia) were exposed to lipid vesicles made in Example 2 containing either free dexamethasone or DPGS-dexamethasone in amounts ranging from 0.1 $\mu$g/ml to 100 $\mu$g/ml of dexamethasone per vesicle. Cell viability was determined with an MTT cell viability assay. For the human cell line, apoptosis occurred only at the higher doses above 50 $\mu$g/ml, but there was no difference in response between the vesicles containing free dexamethasone and those containing DPGS-dexamethasone. Similarly, while the murine leukemia line was sensitive to the drug at lower levels (less than 10 $\mu$g/ml), there was no difference in response between the vesicles containing free dexamethasone and those containing DPGS-dexamethasone. The results support the hypothesis that the dexamethasone prodrug retains the bioactivity of free dexamethasone in stimulating apoptosis.

Example 6

A partially fluorinated carboxylic acid, of the formula HOOC—(CH$_2$)$_4$—(CF$_2$)$_8$—CF$_3$ was prepared by hydrolzyzation and oxidation of PEG-Telomer B (the Dupont Company). Thereafter, the compound of the formula HOOC—(CH$_2$)$_4$—(CF$_2$)$_8$—CF$_3$ 0.7 g, dexamethasone 0.4 g, and N,N-dimethylaminopyridine 50 mg were dissolved in 30 ml chloroform, and added to a solution of dicyclohexylcarbodiimide 0.21 g in chloroform 10 ml while stirring at 0–5° C. for 8 hours. 5 ml of 1% acetic acid was added and stirred for one hour, then the water layer was separated out, and washed with water again. The organic layer was dried over anhydrous sodium sulfate, and then the organic solvent was evaporated on a rotaevaporator. The residue was redissolved in acetonitrile, the precipitate was filtered out, and the solution was evaporated on an evaporator to dryness. A white solid was obtained and was recrystallized from methanol, resulting in a fluorinated prodrug of dexamethasone of the formula:

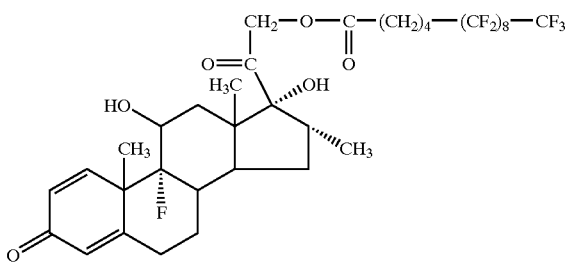

Example 7

Example 4 was duplicated except that the vesicles were prepared from a mixture of 6% soybean oil, 5% sorbitol, 0.02M NaCl, 0.5% Tween 20 (e.g., polyoxyethylenesorbitan monooleate) and 1% v/v perfluoropentane in an aqueous suspension.

Incremental amounts of DPGS-dexamethasone from Example 1 may be added to the above mixture until saturation is achieved at about 2.0 mM. In a similar manner, incremental amounts of uncomplexed dexamethasone may be added to the above mixture until saturation is achieved at about 0.2 mM. Thus, the DPGS-dexamethasone may be ten times more soluble in the emulsion when compared to free dexamethasone, indicating the material may be suitable for local and intravenous targeted administration at drug concentrations ten-fold enhanced over lipophilic suspensions of free steroid.

Example 8

The procedure of Example 7 was repeated with lipid coated vesicles formulated from a 10 ml mixture of 3.6 w/v m-HES hydroxyethylstarch (Ajinimoto, Tokyo, Japan), 3.0% w/v sodium chloride, 2.99% phosphate buffer (titrated to pH 7.0 with conc. NaOH), 0.45% dipalmitoylphosphatidylcholine, (Avanti, Alabaster, Ala.), 0.15% polxamer 188 (PLURONICS®, BASF, Parsippany, N.J.) and 3.0% perfluoropentane.

Incremental amounts of DPGS-dexamethasone from Example 1 may be added to the above mixture until saturation is achieved at about 2.0 mM. In a similar manner, incremental amounts of uncomplexed dexamethasone may be added to the above mixture until saturation is achieved at about 2 mM. Thus, the DPGS-dexamethasone may be ten times more soluble in the emulsion when compared to free dexamethasone, indicating the material may be suitable for local and intravenous targeted administration at drug concentrations ten-fold enhanced over lipophilic suspensions of free steroid.

Example 9

DPGS-dexamethasone from Example 1 may be mixed with dipalmitoyl-phosphatidylcholine (DPPC) and cholesterol at a 2:6:2 molar ratio (total lipid concentration is 50 mg/ml, volume 50 ml) in ethanol and swirled by hand in a round bottom flask. The resulting lipid/prodrug suspension may then be dried to a fine glaze by rotary evaporator. The resulting dried lipid film may then be hydrated in normal saline and stirred with a stir bar while the material is heated to 50° C. for 30 minutes. The resulting multilamellar vesicles may then be subjected to extrusion using an Extruder Device (Lipex Biomembranes, Vancouver, B.C., Canada) at 8,000 psi using pressurized nitrogen gas. The Extruder device may be equipped with a thermal barrel to maintain the temperature at 55° C. Two passes may be made through an 8 micron filter, 2 passes through a 2 micron filter, 5 passes through a 400 μm filter and 10 passes through a 100 μm filter. The resulting product may consist chiefly of unilamellar DPGS-dexamethasone-laden liposomes with a mean diameter of about 100 μm.

Example 10

The procedure in Example 9 may be substantially repeated except that a Microfluidizer (Microfluidics, Newton, Mass.) may be used to homogenize the multilamellar vesicles instead of the Extruder Device. Ten passes may be made through the Microfluidizer at a pressure of 14,000 psi while the temperature of the suspension is maintained at about 55° C. Small unilamellar vesicles may result with diameters ranging from about 100 nm to about 30 nm.

The above may be substantially repeated except that 5 mole % dipalmitoyl-phosphatidylethanolamine-PEG5000 (DPPE-PEG5000) may be incorporated into the lipids at the step of suspending the lipids in the ethanol. The result will be DPGS-dexamethasone prodrug liposomes.

Example 11

To a cooled (0 to 5° C.) solution of 1,2-dipalmitoyl-sn-glycero-3-succinate 66.8 mg, N-hydroxy-succinimide 11.5 mg, dimethylaminopyridine (DMAP) 2 mg and acetonitrile 40 mL in a 100 mL round bottom flask was added dropwise to a solution of dicyclohexyl carbodiimide (DCC) 20.6 mg in acetonitrile 10 mL. The resulting mixture was stirred for 5 hours. The solid material which formed during the reaction (dicyclohexylurea) was removed by filtration, and the filtrate was concentrated in vacuo to yield 78 mg of a white product of N-DPGS-succinimide of the following formula:

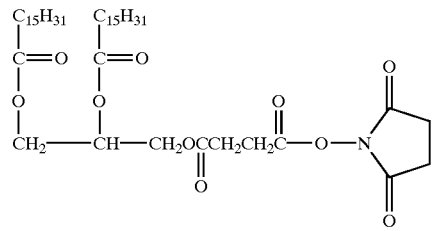

To a cooled (0 to 5° C.) solution of the above N-DPGS-succinimide (78 mg) and CHCl₃ (10 mL) (Mallinckrodt, St. Louis, Mo.) in a 100 mL round bottom flask was added dropwise a solution of ω-amino-ω'-carboxy-polyethyleneglycol (0.3 g) and triethylamine (40 mg) in CHCl₃ (20 mL). The resulting mixture was stirred for 5 hours at 10° C. After stirring overnight, the reaction mixture was poured into ice water and neutralized with 10% HCl to a pH of about 3 or less. The lower organic layer was removed using a separatory funnel and washed three times with water. The organic layer was collected and dried (NaSO₄). Filtration and concentration in vacuo yielded 0.34 g of a white solid of 3-ω-carboxy-polyethyleneglycol-imino-succinat-1,2-dipalmitoyl-sn-glycerol (DPGS-ω-carboxy-PEG), of the formula:

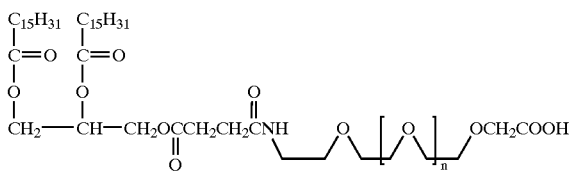

where n is 8 (it is noted that n may be an integer of from about 3 to about 20).

To a cooled (0 to 5° C.) solution of DPGS-ω-carboxy-PEG (200 mg) from Step B, N-hydroxysuccinimide (6 mg), dimethylaminopyridine (DMAP) (2 mg) and acetonitrile (40 mL) in a 250 mL round bottom flask was added dropwise a solution of dicyclohexyl carbodiimide (DCC) (12 mg) in acetonitrile (10 mL). The resulting mixture was stirred for 5 hours and the white solid which formed (dicyclohexylurea) was removed by filtration. The filtrate was concentrated in vacuo to yield 200 mg of a white solid of 3-succinamoyl-oxy-carbonyl-polyethyleneglycol-imino-succinate-1,2-dipalmitoyl-sn-glycerol (DPGS-ω-carboxy-PEG-succinimide), of the formula:

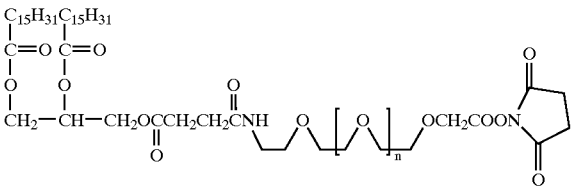

where n is 8 (it is noted that n may be an integer of from about 3 to about 20).

To a cooled (5 to 10° C.), stirred solution of human IL-2 (20 mg) (Sigma Chemical Co., St. Louis, Mo.) in an aqueous buffer (20 mL) at a pH of 8.5 was added dropwise a solution of DPGS-(ω-carboxy-PEG-succinimide from Step C (4 mg) and acetonitrile (10 mL). The temperature of the resulting mixture was equilibrated to room temperature and the reaction mixture was stirred for about 48 hours. The mixture was concentrated in vacuo and the residual salts were dialyzed away using a dialysis bag having a molecular weight cutoff of about 3500, equilibrated against water. The resulting dialyzed solution was frozen and lyophilized to yield 12 mg of a white solid of a N-(1,2-dipalmitoyl-sn-glycero-3-succinyl)-PEG-Interleukin-2 (DPGS-PEG-IL-2) conjugate targeting moiety, of the formula:

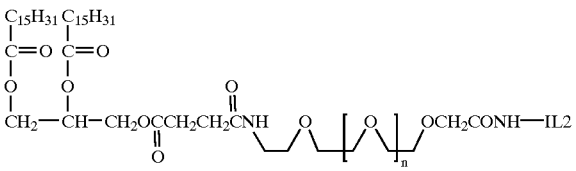

where n is 8 (it is noted that n may be an integer of from about 3 to about 20).

Example 12

A bifunctional delivery vehicle containing the DPGS-dexamethasone of Example 1 and the N-(1,2-dipalmitoyl-sn-glycero-3-succinyl)-PEG-Interleukin-2 conjugate targeting moiety of Example 11 was prepared as follows.

60 mol % dipalmitoylphosphatidylcholine (DPPC), 10 mol % dipalmitoyl-phosphatidic acid (DPPA), 8 mol % dipalmitoylphosphatidylethanolamine-PEG5000 (DPPE-PEG 5000), and 18 mol % DPGS-dexamethasone from Example 1, and 4 mol % N-(1,2-dipalmitoyl-sn-glycero-3-succinyl)-PE Interleukin-2 from Example 11 were suspended in ddH$_2$O and mixed together with swirling. The lipids were lyophilized and resuspended in 8:1:1 molar ratio of saline/propylene glycol/glycerol at a lipid concentration of 3 mg/ml. The resulting suspension was transferred to 1.5 ml vials and the headspace was evacuated under vacuum. Perfluoropentane gas was used to fill the headspace and the vials were stoppered and sealed. Perfluoropentane gas filled bifunctional delivery vehicles were readily prepared by agitation, e.g., on a Wig-L-Bug at 2800 rpm for 60 seconds.

Example 13

This example is based on the extrapolation and interpretation of experiments described, for example, by Cesano et al, *Cancer Research*, 55(1):96–101 (1995) and O'Connor et al, *Blood*, 77(7):1534–45 (1991), the disclosures of which are hereby incorporated herein by reference in their entirety.

The cell line TALL-104 (ATCC CRL-11386), a cytotoxic human t-cell acute lymphoblastic leukemia which expresses CD8 and CD2 receptors, is employed for IL-2 activation. The control cell line is INT407, which is a human intestinal cell line. The cells will be plated in flat sided tissue culture tubes (Nunc, Roskilde, Denmark) in EMEM media (Cellgro, Washington, D.C.). The cells will be grown overnight and aliquots of vesicle compositions will be added to each tube.

Vesicles from Example 2 and vesicles from Example 12 will be used. Three experimental cell types will be used, INT 407, Hela and TALL-104, that will be exposed to 10% glucose for 10 minutes to shock the cells and open pores to allow binding of the antimyosin to the cytoplasmic myosin. Light microscopy will be performed with a Nikon Diaphot 300 at 400× magnification to determine whether the vesicles are able to bind to the surface of the t-cells. Standard assays will be used to qualitatively measure binding of the vesicles and the cell types.

No binding will be observed with vesicle compositions from Examples 2 or 12 in any of the INT 407 cell types. No binding will be observed with vesicle compositions from Example 2 in the Hela cell types or the Tall-104 cell types. Some binding of vesicle compositions from Example 12 to Hela cell types will be observed. Substantial binding of vesicle compositions from Example 12 to Tall-104 cell types will be observed.

Example 14

Example 11 was repeated except that an Interleukin-2 hexapeptide fragment (i.e., Leu-Glu-His-Leu-Leu-Leu) having affinity for the IL-2 receptor on CD8-bearing t-cells was substituted for whole IL-2. The fragment was located at residues 34–39 of native human IL-2. See, e.g., Wiegent, et al., *Biochem. Biophys. Res. Comm.*, 139:367–374 (1986).

Example 15

Example 14 was repeated except that a spacer comprising a hexapeptide of mixed D and L amino acids (i.e., $NH_2$-D-ala-leu-D-val-phe-D-ile-gly-COOH) was added on the amino terminal of the IL-2 receptor recognition fragment.

Example 16

The procedure described in Example 11 was followed except that, instead of conjugating IL-2, the ligand for human lymphocyte function-associated antigen 3 (LFA-3)

was attached to the DPGS-PEG moiety. LFA-3 is a ligand with affinity for the CD2 receptor, and the cDNA of LFA-3 defines a mature protein of 222 amino acids that structurally resemble typical membrane-anchored proteins, as described, for example, by Wallner et al, *Journal of Experimental Medicine*, 166:923–932 (1987), the disclosure of which is hereby incorporated by reference herein in its entirety.

Example 17

30% (w/w) of DPGS-dexamethasone and 70% of a lipid mixture comprising 53.3 mol % DPPC, 40.5 mol % DPPE-PEG500, 6 mol % DPPA were mixed together. The mixture was made in water shell frozen with liquid nitrogen and lyophilized. After lyophilization, the material was resuspended in 8:1:1 at a concentration of 1 mg/ml. The mixture was aliquotted into 2 ml Wheaton vials and the headspace was replaced with perfluorobutane. The vials were shaken for 60 seconds on an ESPE Capmix.

12 mice were implanted with tumors, of which 4 were placed in a no treatment group; 4 received the above mixture, and 4 received the above mixture and ultrasound. Of the 10 mice that eventually received the drug, 6 mice died immediately with spasming.

Thereafter, the above mixture was reformulated to reduce toxicity by adding 7.5 μl of Pluronic® L61 (poloxamer 181, a liquid block copolymer of ethylene oxide, propylene oxide and propylene glycol, BASF, Parsippany, N.J.) to a 1.5 ml sample of the above mixture (30% DPGS-dexamethasone and 70% lipid mixture) to reduce the particles above 10 μm. Of the 21 mice that were administered the reformulated mixture, only 1 died.

Example 18

20 milliliters of the reformulated mixture from Example 17, having a lipid concentration of 1 mg/ml and containing 30% (w/w) DPGS-dexamethasone, will be intraveously injected into a patient with rheumatoid arthritis. A 1.0 MHz Piclarner continuous wave transducer will be placed onto the patient's affected joint. Silicon gel will be applied to the patient's skin as a couplant to improve sound transmission. Power will be applied at 1.0 watt/$cm^2$, 100% duty cycle. Each affected joint will be sonicated separately for 2–5 minutes following intravenous injection of the steroid pro-drug vesicles described above. As the acoustically active vesicles pass through the vessels of the inflamed synovial tissues in the joints, the vesicles will burst and release dexamethasone in the target tissue and inflammation will decrease. Because of improved target tissue uptake, systemic toxicity will be reduced, greater amounts of dexamethasone will reach the affected tissue, and less dexamethasone will accumulate at unwanted sites in the patient's body.

Example 19

Atlantic salmon (*Salmo salar*) form sunburn cells when they are reared in cage cultures near the surface of the water. DPGS-dexamethasone will be administered to the salmon via the caudal vein. Low power ultrasound emitters will be attached to the cage stanchions. The low power ultrasound will only be sufficient to penetrate the sacles and get to the skin below. This deposition of DPGS-dexamethasone will act to reduce the inflammation due to sunburn cell formation.

The disclosures of each patent, patent application and publication cited or described in this document are hereby incorporated by reference herein in their entirety.

Various modifications of the invention, in addition to those described herein, will be apparent to those skilled in the art from the foregoing description. Such modifications are also intended to fall within the scope of the appended claims.

What is claimed is:

1. A method of delivering a steroid to a patient in need thereof comprising administering to a patient a composition comprising a gas, a gaseous precursor, or a gas and a gaseous precursor, and a compound of formula (I):

$$D-X-L \qquad (I)$$

wherein:

D is dexamethasone;

X is a linking group comprising a carboxylic acid ester group; and

L is selected from the group consisting of dipalmitoylglyceryl, dimyristoylglyceryl, distearoylglyceryl and dioleoylglyceryl.

2. A method of claim 1, wherein said administration is intravenous.

3. A method of claim 1, wherein said administration is topical.

4. A method of claim 1, wherein said lipid moiety forms a vesicle.

5. A method of claim 1, wherein said lipid moiety is non-vesicular.

6. A method of claim 1, wherein said composition further comprises a fluorinated liquid.

7. A method of claim 6, wherein said fluorinated liquid is selected from the group consisting of perfluorooctylbromide, perfluorooctyliodide, perfluorotripropylamine, perfluorotributylamine, perfluorodecalin and perfluorododecalin.

8. A method of claim 1, wherein the gas or gaseous precursor is selected from the group consisting of nitrogen, sulfur hexafluoride, a perfluorocarbon and a perfluoroether.

9. A method of claim 8, wherein the perfluorocarbon is selected from the group consisting of perfluoromethane, perfluoroethane, perfluoropropane, perfluorobutane, perfluoropentane, perfluorohexane, perfluoroheptane, perfluorooctane, perfluorononane, perfluorocyclobutane, perfluorocyclopropane and perfluorocyclopentane.

10. A method of claim 8, wherein the pertluoroether is selected from the group consisting of perfluorobutylmethylether, perfluoromethylpentylether, perfluorotetrahydropyran and pertluoromethyltetrahydrofuiran.

11. A method of claim 1, wherein X is succinate.

12. A method of claim 1, where L is dipalmitoylglyceryl.

13. A method of claim 1, wherein said compound of formula (I) is:

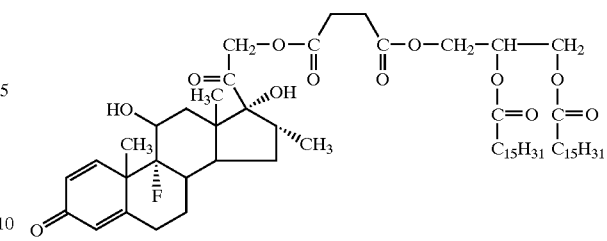

* * * * *